US012257295B2

(12) United States Patent
Forrest et al.

(10) Patent No.: US 12,257,295 B2
(45) Date of Patent: Mar. 25, 2025

(54) SACCHARIDE-POLYPEPTIDE CONJUGATE COMPOSITIONS AND METHODS OF USE THEREOF

(71) Applicant: Pogona, LLC, South Nyack, NY (US)

(72) Inventors: Bruce D. Forrest, South Nyack, NY (US); Jack D. Love, Tampa, FL (US)

(73) Assignee: Pogona, LLC, South Nyack, NY (US)

( * ) Notice: Subject to any disclaimer, the term of this patent is extended or adjusted under 35 U.S.C. 154(b) by 0 days.

(21) Appl. No.: 16/753,597

(22) PCT Filed: Oct. 4, 2018

(86) PCT No.: PCT/US2018/054391
§ 371 (c)(1),
(2) Date: Apr. 3, 2020

(87) PCT Pub. No.: WO2019/070994
PCT Pub. Date: Apr. 11, 2019

(65) Prior Publication Data
US 2020/0330579 A1   Oct. 22, 2020

Related U.S. Application Data

(60) Provisional application No. 62/732,260, filed on Sep. 17, 2018, provisional application No. 62/568,164, filed on Oct. 4, 2017.

(51) Int. Cl.
| | | |
|---|---|---|
| A61K 39/09 | (2006.01) | |
| A61K 9/08 | (2006.01) | |
| A61K 39/00 | (2006.01) | |
| A61K 39/39 | (2006.01) | |
| A61K 45/06 | (2006.01) | |
| A61K 47/10 | (2017.01) | |
| A61K 47/18 | (2017.01) | |
| A61K 47/26 | (2006.01) | |

(52) U.S. Cl.
CPC .............. *A61K 39/092* (2013.01); *A61K 9/08* (2013.01); *A61K 39/39* (2013.01); *A61K 47/10* (2013.01); *A61K 47/183* (2013.01); *A61K 47/26* (2013.01); *A61K 2039/54* (2013.01); *A61K 2039/545* (2013.01); *A61K 2039/55505* (2013.01); *A61K 2039/6037* (2013.01); *A61K 45/06* (2013.01)

(58) Field of Classification Search
CPC .................................................. A61K 39/092
See application file for complete search history.

(56) References Cited

U.S. PATENT DOCUMENTS

| | | |
|---|---|---|
| 4,221,906 A | 9/1980 | Querry et al. |
| 4,242,501 A | 12/1980 | Cano et al. |
| 4,459,286 A | 7/1984 | Hilleman et al. |
| 4,496,538 A | 1/1985 | Gordon |
| 4,673,574 A | 6/1987 | Anderson |
| 4,686,102 A | 8/1987 | Ritchey et al. |
| 4,902,506 A | 2/1990 | Anderson et al. |
| 5,097,020 A | 3/1992 | Anderson et al. |
| 5,192,540 A | 3/1993 | Kuo et al. |
| 5,360,897 A | 11/1994 | Anderson et al. |
| 5,445,817 A | 8/1995 | Schneerson et al. |
| 5,623,057 A | 4/1997 | Marburg et al. |
| 5,695,768 A | 12/1997 | Malcolm |
| 5,847,112 A | 12/1998 | Kniskern et al. |
| 5,965,714 A | 10/1999 | Ryall |
| 6,224,880 B1 | 5/2001 | Chan et al. |
| 6,451,317 B1 | 9/2002 | Blake et al. |
| 6,656,472 B1 | 12/2003 | Chong et al. |
| 7,018,637 B2 | 3/2006 | Chong et al. |
| 7,588,765 B2 | 9/2009 | Porro |
| 7,709,001 B2 | 5/2010 | Hausdorff et al. |
| 7,862,823 B1 | 1/2011 | Leroy |
| 7,955,605 B2 | 6/2011 | Prasad |
| 8,029,798 B2 | 10/2011 | Leroy |
| 8,192,746 B2 | 6/2012 | Caulfield et al. |
| 8,481,054 B2 | 7/2013 | Nahm et al. |
| 8,603,484 B2 | 12/2013 | Prasad |
| 8,753,645 B2 | 6/2014 | Biemans et al. |
| 8,808,707 B1 | 8/2014 | Siber et al. |
| 8,808,708 B2 | 8/2014 | Hausdorff et al. |
| 8,895,024 B2 | 11/2014 | Hausdorff et al. |
| 8,926,985 B2 | 1/2015 | Capiau et al. |
| 9,095,567 B2 | 8/2015 | Khandke et al. |
| 9,107,872 B2 | 8/2015 | Biemans et al. |
| 9,168,313 B2 | 10/2015 | Capiau et al. |
| 9,359,400 B2 | 6/2016 | Usera et al. |
| 9,399,060 B2 | 7/2016 | Hausdorff et al. |

(Continued)

FOREIGN PATENT DOCUMENTS

| | | | |
|---|---|---|---|
| CN | 104069488 A | 10/2014 | |
| EP | 0338265 B1 | 5/1994 | |

(Continued)

OTHER PUBLICATIONS

Extended European Search Report, mailed Jun. 7, 2021, in connection with Application No. EP 18864637.6.
[No Author Listed], Decision Denying Institution of Inter Partes Review 37 C.F.R. § 42.108. Case IPR2017-01223. U.S. Pat. No. 9,399,060 B2. Paper 8. Oct. 20, 2017. 22 pages.
Cox et al., Investigating the candidacy of a capsular polysaccharide-based glycoconjugate as a vaccine to combat *Haemophilus influenzae* type a disease: A solution for an unmet public health need. Vaccine. Oct. 27, 2017;35(45):6129-6136. doi: 10.1016/j.vaccine.2017.09.055. Epub Sep. 23, 2017.

(Continued)

*Primary Examiner* — Brian Gangle
*Assistant Examiner* — Lakia J Jackson-Tongue
(74) *Attorney, Agent, or Firm* — Wolf, Greenfield & Sacks, P.C.

(57) ABSTRACT

Saccharide-polypeptide conjugates, compositions containing these, methods of making and using the conjugates and compositions, and kits containing these, are disclosed.

20 Claims, 15 Drawing Sheets

Specification includes a Sequence Listing.

(56) References Cited

U.S. PATENT DOCUMENTS

| | | | |
|---|---|---|---|
| 9,492,559 B2 | 11/2016 | Emini et al. | |
| 9,610,340 B2 | 4/2017 | Biemans et al. | |
| 9,669,084 B2 | 6/2017 | Siber et al. | |
| 9,764,039 B2 | 9/2017 | Thanos et al. | |
| 9,884,113 B2 | 2/2018 | Biemans et al. | |
| 9,981,035 B2 | 5/2018 | Hausdorff et al. | |
| 10,124,050 B2 | 11/2018 | Watson et al. | |
| 10,716,848 B2 | 7/2020 | Hausdorff et al. | |
| 11,058,757 B2* | 7/2021 | Forrest | A61K 39/092 |
| 11,116,828 B2 | 9/2021 | Smith et al. | |
| 11,701,416 B2 | 7/2023 | Malley et al. | |
| 11,850,278 B2 | 12/2023 | Smith et al. | |
| 2005/0214329 A1 | 9/2005 | Laferriere et al. | |
| 2006/0228380 A1* | 10/2006 | Hausdorff | A61K 39/092 424/244.1 |
| 2009/0010959 A1 | 1/2009 | Biemans et al. | |
| 2015/0344530 A1 | 12/2015 | Kapre | |
| 2015/0374811 A1 | 12/2015 | Malley et al. | |
| 2016/0324949 A1 | 11/2016 | Han et al. | |
| 2017/0021006 A1 | 1/2017 | Watson et al. | |
| 2018/0333484 A1* | 11/2018 | Fairman | A61P 31/04 |
| 2020/0054739 A1* | 2/2020 | Fairman | A61P 31/04 |
| 2020/0113993 A1* | 4/2020 | Forrest | A61K 47/646 |
| 2020/0188502 A1* | 6/2020 | Faridmoayer | A61K 39/092 |
| 2020/0282040 A1* | 9/2020 | Porambo | C08B 37/0003 |
| 2020/0282070 A1* | 9/2020 | Porambo | A61P 11/00 |
| 2020/0330578 A1* | 10/2020 | Porambo | A61P 11/00 |
| 2020/0360500 A1* | 11/2020 | Chintala | A61K 9/0019 |
| 2021/0393764 A1* | 12/2021 | Cooper | A61P 31/04 |
| 2022/0143167 A1 | 5/2022 | Forrest et al. | |

FOREIGN PATENT DOCUMENTS

| | | |
|---|---|---|
| EP | 2865392 A1 | 4/2015 |
| WO | WO 2003/051392 A2 | 6/2003 |
| WO | WO 2007/071707 A2 | 6/2007 |
| WO | WO 2008/143709 A2 | 11/2008 |
| WO | WO 2011/100151 A1 | 8/2011 |
| WO | WO 2014/118201 A1 | 8/2014 |
| WO | WO 2016/113644 A1 | 7/2016 |
| WO | WO 2016/149771 A1 | 9/2016 |
| WO | WO 2016/207905 A2 | 12/2016 |
| WO | WO 2017/067962 A1 * | 4/2017 |
| WO | WO 2017/173415 A2 | 10/2017 |
| WO | WO 2018/064444 A1 | 4/2018 |
| WO | WO 2019/070994 A1 | 4/2019 |
| WO | WO 2019/139692 A2 | 7/2019 |
| WO | WO 2020/056202 A1 | 3/2020 |

OTHER PUBLICATIONS

Frasch, Analytical and Manufacturing Challenges: Preparation of Bacterial Polysaccharide Conjugates. Vaccine Technology III. Session IV: Conjugate Vaccines. Albufeira, Portugal. Jun. 1-6, 2008. 20 pages.

Guo et al., Genetic diversity of fluoroquinolone-nonsusceptible *Streptococcus pneumoniae* clinical isolates and the first identification of serotype 20B in China. Eur J Clin Microbiol Infect Dis. Mar. 2014;33(3):465-70. doi: 10.1007/s10096-013-1979-5. Epub Oct. 4, 2013.

Nunes et al., The impact of private use of PCV7 in 2009 and 2010 on serotypes and antimicrobial resistance of *Streptococcus pneumoniae* carried by young children in Portugal: Comparison with data obtained since 1996 generating a 15-year study prior to PCV13 introduction. Vaccine. Mar. 29, 2016;34(14):1648-56. doi: 10.1016/j.vaccine.2016.02.045. Epub Feb. 23, 2016.

Chochua et al., Invasive Serotype 35B Pneumococci Including an Expanding Serotype Switch Lineage, United States, 2015-2016. Emerg Infect Dis. Jun. 2017;23(6):922-930. doi: 10.3201/eid2306. 170071. Erratum in: Emerg Infect Dis. Oct. 2017;23(10):1762.

Curry et al., Preclinical evaluation of an investigational 21-valent pneumococcal conjugate vaccine, V116, in adult-rhesus monkey, rabbit, and mouse models. Vaccine. Jan. 23, 2023;41(4):903-913. doi: 10.1016/j.vaccine.2022.12.017. Epub Dec. 22, 2022.

Del Amo et al., High invasiveness of pneumococcal serotypes included in the new generation of conjugate vaccines. Clin Microbiol Infect. Jul. 2014;20(7):684-9. doi: 10.1111/1469-0691.12422. Epub Nov. 8, 2013.

Huang et al., Continued impact of pneumococcal conjugate vaccine on carriage in young children. Pediatrics. Jul. 2009;124(1):e1-11. doi: 10.1542/peds.2008-3099. Author Manuscript, 21 pages.

Kauffmann et al., Memorandum on the Nomenclature of the Pneumococcus Group. Int Bull Bacteriol Nomen Tax. Apr. 15, 1954;4(2):125-128.

Porat et al., Four antibiotic-resistant *Streptococcus pneumoniae* clones unrelated to the pneumococcal conjugate vaccine serotypes, including 2 new serotypes, causing acute otitis media in southern Israel. J Infect Dis. Feb. 1, 2004;189(3):385-92. doi: 10.1086/381183. Epub Jan. 16, 2004.

Robbins et al., Considerations for formulating the second-generation pneumococcal capsular polysaccharide vaccine with emphasis on the cross-reactive types within groups. J Infect Dis. Dec. 1983;148(6):1136-59. doi: 10.1093/infdis/148.6.1136.

Schiffman, G., Chemistry and immunochemistry of the pneumococcal polysaccharide vaccine with special reference to cross-reactions and immunologic factors. Rev Infect Dis. Mar.-Apr. 1981;3 Suppl:S18-30. doi: 10.1093/clinids/3.supplement_1.s18.

Sih, T.M., Acute otitis media in Brazilian children: analysis of microbiology and antimicrobial susceptibility. Ann Otol Rhinol Laryngol. Jul. 2001;110(7 Pt 1):662-6. doi: 10.1177/000348940111000712.

Extended European Search Report, mailed Nov. 4, 2019, in connection with Application No. EP 17776881.

International Search Report and Written Opinion, mailed Sep. 13, 2017, in connection with Application No. PCT/US2017/025621.

International Preliminary Report on Patentability, mailed Oct. 11, 2018, in connection with Application No. PCT/US2017/025621.

International Search Report and Written Opinion, mailed Feb. 11, 2019, in connection with Application No. PCT/US2018/054391.

International Preliminary Report on Patentability, mailed Apr. 16, 2020, in connection with Application No. PCT/US2018/054391.

Bentley et al., Genetic Analysis of the Capsular Biosynthetic Locus from All 90 Pneumococcal Serotypes. PLoS Genet. Mar. 2006; 2(3): e31. Epub Mar. 10, 2006. doi: 10.1371/journal.pgen.0020031.

Durando et al., Experience with pneumococcal polysaccharide conjugate vaccine (conjugated to CRM197 carrier protein) in children and adults. Clin Microbiol Infect. 2013;19 Suppl 1:1-9. doi: 10.1111/1469-0691.12320.

Hu et al., Towards the next generation of biomedicines by site-selective conjugation. Chem Soc Rev. 2016;45(6):1691-1719. doi:10. 1039/c4cs00388h.

Jefferies et al., 13-valent pneumococcal conjugate vaccine (PCV13). Hum Vaccin. 2011;7(10):1012-1018. doi: 10.4161/hv.7.10.16794.

Kolkman et al., Functional analysis of glycosyltransferases encoded by the capsular polysaccharide biosynthesis locus of *Streptococcus pneumoniae* serotype 14. J Biol Chem. 1997;272(31):19502-19508. doi: 10.1074/jbc.272.31.19502.

Skinner et al., Pre-clinical evaluation of a 15-valent pneumococcal conjugate vaccine (PCV15-CRM197) in an infant-rhesus monkey immunogenicity model. Vaccine. 2011;29(48):8870-8876. doi:10. 1016/j.vaccine.2011.09.078.

* cited by examiner

SEQUENCE LISTING

```
<160> NUMBER OF SEQ ID NOS: 1

<210> SEQ ID NO 1
<211> LENGTH: 535
<212> TYPE: PRT
<213> ORGANISM: Artificial Sequence
<220> FEATURE:
<223> OTHER INFORMATION: Synthetic Polypeptide

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270
```

```
Phe Ala Gly Ala Asn Tyr Ala Ala Trp Ala Val Asn Val Ala Gln Val
        275                 280                 285
Ile Asp Ser Glu Thr Ala Asp Asn Leu Glu Lys Thr Thr Ala Ala Leu
    290                 295                 300
Ser Ile Leu Pro Gly Ile Gly Ser Val Met Gly Ile Ala Asp Gly Ala
305                 310                 315                 320
Val His His Asn Thr Glu Glu Ile Val Ala Gln Ser Ile Ala Leu Ser
                325                 330                 335
Ser Leu Met Val Ala Gln Ala Ile Pro Leu Val Gly Glu Leu Val Asp
                340                 345                 350
Ile Gly Phe Ala Ala Tyr Asn Phe Val Glu Ser Ile Ile Asn Leu Phe
            355                 360                 365
Gln Val Val His Asn Ser Tyr Asn Arg Pro Ala Tyr Ser Pro Gly His
    370                 375                 380
Lys Thr Gln Pro Phe Leu His Asp Gly Tyr Ala Val Ser Trp Asn Thr
385                 390                 395                 400
Val Glu Asp Ser Ile Ile Arg Thr Gly Phe Gln Gly Glu Ser Gly His
                405                 410                 415
Asp Ile Lys Ile Thr Ala Glu Asn Thr Pro Leu Pro Ile Ala Gly Val
                420                 425                 430
Leu Leu Pro Thr Ile Pro Gly Lys Leu Asp Val Asn Lys Ser Lys Thr
            435                 440                 445
His Ile Ser Val Asn Gly Arg Lys Ile Arg Met Arg Cys Arg Ala Ile
        450                 455                 460
Asp Gly Asp Val Thr Phe Cys Arg Pro Lys Ser Pro Val Tyr Val Gly
465                 470                 475                 480
Asn Gly Val His Ala Asn Leu His Val Ala Phe His Arg Ser Ser Ser
                485                 490                 495
Glu Lys Ile His Ser Asn Glu Ile Ser Ser Asp Ser Ile Gly Val Leu
                500                 505                 510
Gly Tyr Gln Lys Thr Val Asp His Thr Lys Val Asn Ser Lys Leu Ser
        515                 520                 525
Leu Phe Phe Glu Ile Lys Ser
530                 535
```

SACCHARIDE-POLYPEPTIDE CONJUGATE COMPOSITIONS AND METHODS OF USE THEREOF

RELATED APPLICATIONS

This application is a national stage filing under 35 U.S.C. § 371 of international PCT application, PCT/US2018/054391, filed Oct. 4, 2018, which claims priority under 35 U.S.C. § 119 (e) to U.S. Provisional Application, U.S. Ser. No. 62/568,164, filed Oct. 4, 2017, and U.S. Provisional Application, U.S. Ser. No. 62/732,260, filed Sep. 17, 2018, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 1, 2018, is named 50308-706_601_SL.txt and is 5,037 bytes in size.

SUMMARY

Provided herein is a brief summary. This summary can be used to provide an understanding of the embodiments provided herein, but the embodiments are not limited to what is provided in this summary.

Provided herein is a pharmaceutical composition in unit dose form that can comprise a plurality of at least eight unique immunogenic saccharide-polypeptide conjugates each comprising individually a capsular polysaccharide, fragment thereof, or combination thereof conjugated to a polypeptide, wherein the capsular polysaccharide, fragment thereof, or combination thereof is from a unique *Streptococcus pneumoniae* serotype selected from a group consisting of 2, 6C, 7C, 8, 9N, 10A, 11A, 12F, 15A, 15B, 15C, 16F, 17F, 20A, 20B, 22F, 23A, 23B, 24F, 24B, 31, 33F, 33B, 34, 35B, 35F, and 38, and wherein a total amount of capsular polysaccharide, fragment thereof, or combination thereof, individually for each *Streptococcus pneumoniae* serotype in the pharmaceutical composition in unit dose form, ranges from about 0.5 µg to about 5 µg. A pharmaceutical composition in unit dose form can comprises a plurality of at least 29 unique immunogenic saccharide-polypeptide conjugates each comprising individually a capsular polysaccharide, fragment thereof, or combination thereof conjugated to a polypeptide, wherein the capsular polysaccharide, fragment thereof, or combination thereof is from a unique *Streptococcus pneumoniae* serotype selected from a group consisting of 1, 2, 3, 4, 5, 6A, 6B, 7F, 7C, 9V, 14, 18C, 19A, 19F, 23F, 6C, 8, 9N, 10A, 11A, 12F, 15A, 15B, 15C, 16F, 17F, 20A, 20B, 22F, 23A, 23B, 24F, 24B, 31, 33F, 33B, 35F, 34, 35B, and 38, and wherein a total amount of capsular polysaccharide, fragment thereof, or combination thereof, individually for each *Streptococcus pneumoniae* serotype in the pharmaceutical composition in unit dose form, ranges from about 0.5 µg to about 5 µg. A pharmaceutical composition in unit dose form can comprise at least 2 immunogenic saccharide-polypeptide conjugates each comprising individually a capsular polysaccharide, fragment thereof, or combination thereof conjugated to a polypeptide, wherein the capsular polysaccharide, fragment thereof, or combination thereof is from a unique *Streptococcus pneumoniae* serotype group, wherein one serotype is 6C and at least one additional serotype is selected from the group consisting of 1, 2, 3, 4, 5, 6A, 6B, 7F, 7C, 9V, 14, 18C, 19A, 19F, 23F, 8, 9N, 10A, 11A, 12F, 15A, 15B, 15C, 16F, 17F, 20A, 20B, 22F, 23A, 23B, 24F, 24B, 31, 33F, 33B, 34, 35B, and 38, and wherein a total amount of capsular polysaccharide, fragment thereof, or combination thereof, individually for each *Streptococcus pneumoniae* serotype in the pharmaceutical composition in unit dose form, ranges from about 0.5 µg to about 5 µg. A pharmaceutical composition in unit dose form can comprise at least 2 immunogenic saccharide-polypeptide conjugates each comprising individually a capsular polysaccharide, fragment thereof, or combination thereof conjugated to a polypeptide, wherein the capsular polysaccharide, fragment thereof, or combination thereof is from a unique *Streptococcus pneumoniae* serotype group, wherein one serotype is 20B and at least one additional serotype is selected from the group consisting of 1, 2, 3, 4, 5, 6A, 6B, 6C, 7F, 7C, 9V, 14, 18C, 19A, 19F, 23F, 8, 9N, 10A, 11A, 12F, 15A, 15B, 15C, 16F, 17F, 20A, 22F, 23A, 23B, 24F, 24B, 31, 33F, 33B, 34, 35B, and 38, and wherein a total amount of capsular polysaccharide, fragment thereof, or combination thereof, individually for each *Streptococcus pneumoniae* serotype in the pharmaceutical composition in unit dose form, ranges from about 0.5 µg to about 5 µg. A pharmaceutical composition can comprise an immunogenic saccharide-polypeptide conjugate comprising, individually, at least two unique capsular polysaccharides, fragments thereof, or combinations thereof conjugated to a polypeptide, wherein the at least two unique capsular polysaccharides, fragments thereof, or combinations thereof are from a *Streptococcus pneumoniae* serotype selected from a group consisting of 1, 2, 3, 4, 5, 6A, 6B, 7F, 7C, 9V, 14, 18C, 19A, 19F, 23F, 6C, 8, 9N, 10A, 11A, 12F, 15A, 15B, 15C, 16F, 17F, 20A, 20B, 22F, 23A, 23B, 24F, 24B, 31, 33F, 33B, 34, 35F, 35B, and 38. A vaccine in unit dose form can comprise at least one immunogenic saccharide-polypeptide conjugate comprising a capsular polysaccharide, fragment thereof, or combination thereof conjugated to a polypeptide, wherein the capsular polysaccharide, fragment thereof, or combination thereof is from a *Streptococcus pneumoniae* serotype selected from a group consisting of 23A and 23B, or a combination thereof.

Provided herein is a method that can comprise administering to a subject a first composition, wherein the first composition is one of any pharmaceutical composition or vaccine as described herein. Further provided herein is a method that can comprise administering to the subject the first composition occurs at least about four weeks before or at least about four weeks after an administration of a second composition comprising an immunogenic saccharide-polypeptide conjugate comprising a second polypeptide to the subject, wherein the second polypeptide has at least about 70% length homology, at least about 70% sequence homology, or a combination thereof, to the polypeptide of the first composition.

Provided herein is a method that can comprise: administering a second immunogenic saccharide-polypeptide conjugate composition to a subject at least four weeks after a first immunogenic saccharide-polypeptide conjugate composition was administered; wherein the second immunogenic saccharide-polypeptide conjugate composition comprises a first polypeptide that has at least about 70% length homology, at least about 70% sequence homology, or a combination thereof, to a second polypeptide of the second immunogenic saccharide-polypeptide conjugate composition; and wherein the first immunogenic saccharide-polypeptide conjugate composition comprises a first serotype; wherein the second immunogenic saccharide-polypeptide conjugate composition comprises a second serotype, and wherein the first serotype and the second serotype are different; wherein the first immunogenic saccharide-polypeptide conjugate composition or the second immunogenic saccharide-polypeptide conjugate composition is any one of the vaccines described herein.

Further provided herein is a method of making a composition that can comprise: contacting the immunogenic saccharide-polypeptide conjugate of any one of the described pharmaceutical compositions or vaccines with an excipient, an adjuvant, or any combination thereof.

Provided herein is a kit that can comprise any pharmaceutical composition or vaccine described herein contained in a container described herein.

Provided herein are methods of making pharmaceutical compositions or vaccines, methods of immunizing with pharmaceutical compositions or vaccines, and methods of vaccinating with pharmaceutical compositions or vaccines.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
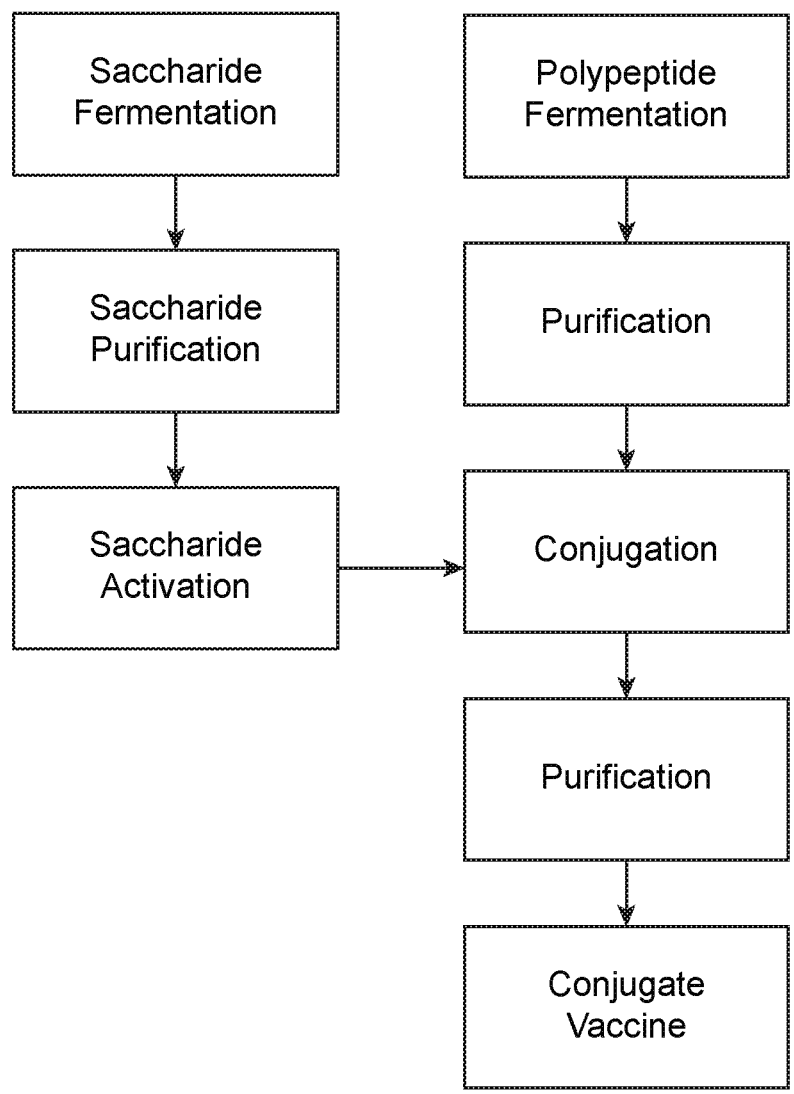
FIG. 1 illustrates a flow diagram of the general process for manufacture of a saccharide peptide conjugate vaccine.

Several aspects are described below with reference to example applications for illustration. It should be understood that numerous specific details, relationships, and methods are set forth to provide a full understanding of the features described herein. One having ordinary skill in the relevant art, however, will readily recognizes that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range covering plus or minus up to 20%, up to 10%, up to 5%, or up to 1% of a given value. Where particular values are described in the application and claims, unless otherwise stated the term "about" can mean within an acceptable error range for the particular value should be assumed. When a conjugate is present in μg, "about" can mean+/−0.5 μg, 0.75 μg, 1.0 μg, 1.25 μg, 1.5 μg, 1.75 μg, or 2 μg for each conjugate.

A "unit dose" when used in reference to a pharmaceutical composition or vaccine can refer to units suitable as unitary dosage for humans, each unit containing a predetermined quantity of active material calculated to produce the desired therapeutic effect. In some instance the unit dose can contain a diluent; i.e., carrier, or vehicle. In some instances, the unit dose can be a physically discrete.

The term "saccharide" can refer to a saccharide, oligosaccharide or polysaccharide. For example, saccharide can mean a monosaccharide, a disaccharide, a trisaccharide, a tetrasaccharide, a pentasaccharide, a hexasaccharide, a heptasaccharide, an octasaccharide, a nonasaccharide, or a decasaccharide. An oligosaccharide can refer to two to ten saccharides. A polysaccharide can refer to more than ten saccharides.

The term "polypeptide" can refer to a single linear chain of amino acids held together by amide bonds. A polypeptide can refer to at least two amino acids. A polypeptide can be an oligopeptide, wherein the term "oligopeptide" can refer to a single chain of from two to twenty amino acids joined by amide bonds. A polypeptide can be a protein, wherein the term "protein" can refer to a single chain of fifty or more amino acids held together by amide bonds.

The term an "immune response" can refer to the production of cytokines and/or antibodies with a degree of specificity for an antigen after administering the antigen to a subject. In some instances, the term "immune response" can refer to any change in immune cells or change caused by immune cells after administering the antigen to a subject. An immune response can be T cell independent, T cell dependent, or both.

The term "homology" can mean percent sequence identity between a particular nucleic acid or amino acid sequence and another nucleic acid or amino acid sequence. First, a nucleic acid or amino acid sequence can be compared another sequence using the BLAST 2 Sequences (Bl2seq) program from the stand-alone version of BLASTZ containing BLASTN version 2.0.14 and BLASTP version 2.0.14. BLASTN can be used to compare nucleic acid sequences, while BLASTP can be used to compare amino acid sequences. Once aligned, the number of matches is determined by counting the number of positions where an identical nucleotide or amino acid residue is presented in both sequences. The percent sequence identity or homology can be determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100%.

The term "length homology" can mean percent length identity between the length of a particular polypeptide and the length of another polypeptide. "Length homology" can in some instances be calculated by dividing the number of amino acids in a first peptide chain by the number of amino acids in a second peptide chain and multiplying the result by 100%. Chain amino acids can be those forming the backbone of the peptide.

The term "length" in reference to a polypeptide can refer to counting the number of amino acids along the amino acid chain.

The term "immunogenic fragment" can be a fragment that is conjugated to a polypeptide, administered to a subject, and which elicits an immune response. In some instances, the fragment can be a fragment of a capsular polysaccharide. In other instances, the polypeptide can be $CRM_{197}$.

Immunogenic, which can but need not be obligated to be preceded any term herein, can mean that which, when administered to a subject, which can be a human or an animal, for example a dog, cat, rat, mouse, sheep, or monkey, produces an immune response in the animal. For example, a dog can be *Canis lupis* familiarius, a cat can be *Felis catus*, a rat can be *Rattus norvegicus*, a mouse can be *Mus musculus*, a sheep can be *Ovis aries*, or a monkey can be *Simia inuus*. The administration can be, for example, subcutaneous, intramuscular, or rectal, for example in the form of a suppository.

In some embodiments, a unique immunogenic saccharide-polypeptide conjugate can be one that differs from other unique immunogenic saccharide-polypeptide conjugates, for example in a plurality of these, by at least one aspect. For example, the unique immunogenic saccharide-polypeptide conjugate can differ by the saccharide or fragment thereof it contains—in that this can render the unique immunogenic saccharide-polypeptide conjugate unique, or by the polypeptide it contains, or both. In some instances, unique immunogenic saccharide-polypeptide conjugates, to be unique, simply need not be 100% identical.

The term "partly mitigated" in reference to the toxin activity of a polypeptide can refer to a decreased toxicity of the polypeptide as compared to a wild type version of the polypeptide.

The term "molecular weight" can be a number average molecular weight or a weight average molecular weight.

The term "plurality" can mean two or more.

The term "subject" can refer to a human or an animal. The subject can be a subject in need thereof.

Bacteria can incorporate saccharides into their surface structure. For example, *Streptococcus pneumoniae* (*S. pneumoniae*) can contain saccharides in its surface structure. The saccharides can be antigens that can induce an immune response in host, such as an animal or human. For example, B cells can produce antibodies against a saccharide. This response can be a T cell independent immune response. An immune response can be induced with full-length, native form polysaccharides, oligosaccharides, or fragments thereof. An immune response can be induced with full-length, native form capsular polysaccharides, or fragments thereof. Other bacteria that can contain saccharides are *Neisseria meningitidis* (*N. meningitidis*), *Salmonella enterica* (*S. enterica*), and *Haemophilus influenzae* (*H. influenzae*).

The saccharides on bacteria can be used to classify the bacteria into a subclass or serotype. More specifically, a serotype can refer to the type of a microorganism determined by its constituent antigens. The constituent antigens can be different saccharides, such as different capsular polysaccharides or immunogenic fragments thereof. Some non-limiting examples of *S. pneumoniae* serotypes can include, but are not limited to 1, 2, 3, 4, 5, 6A, 6B, 6C, 7F, 7C, 8, 9N, 9V, 10A, 11A, 12F, 14, 15A, 15B, 15C, 16F, 17F, 18C, 19F, 19A, 22F, 23F, 23A, 23B, 24F, 24B, 31, 33F, 33B, 34, 35F, 35B, 38, and Serogroup 20 (comprising serotypes 20A and 20B).

By conjugating a saccharide to a polypeptide, the immune response to the saccharide can be enhanced by inducing a T cell dependent response. A saccharide alone may not stimulate T cells because, for example, a saccharide may not be loaded onto the Major Histocompatibility Complex (MHC) of antigen presenting cells. However, peptides can be loaded onto MHC. Therefore, by conjugating a saccharide to a polypeptide, the saccharide-polypeptide conjugate can then be loaded onto the MHC, recognized by the T cell, and stimulate a T cell response. T cells can then stimulate a more vigorous immune response and also promote a more rapid and long-lasting immunologic memory. Provided herein are saccharide-polypeptide conjugates that can be used to induce an immune response, which can be referred to as immunogenic saccharide-polypeptide conjugates. In some instances, the immunogenic saccharide-polypeptide conjugates can provide immune protection against a saccharide or organism containing the saccharides. In other instances, the immunogenic saccharide-polypeptide conjugates can be part of a vaccine.

Compositions of Saccharide-Polypeptide Conjugate

An immunogenic saccharide-polypeptide conjugate composition can be a saccharide conjugated to a polypeptide. An immunogenic saccharide-polypeptide conjugate composition can be a capsular polysaccharide conjugated to a polypeptide. An immunogenic saccharide-polypeptide conjugate composition can be a capsular polysaccharide or fragment of the capsular polysaccharide conjugated to a polypeptide. An immunogenic saccharide-polypeptide conjugate can comprise a saccharide antigen coupled to one or more polypeptides. An immunogenic saccharide-polypeptide conjugate can comprise one unique saccharide antigen coupled a polypeptide. An immunogenic saccharide-polypeptide conjugate can comprise two or more unique saccharide antigens coupled a polypeptide. A saccharide antigen can elicit an immune response.

A saccharide can be from any bacteria and fungi that can incorporate saccharides into their surface structure. For example, saccharides can be from *S. pneumoniae*. Further examples include saccharides from *N. meningitidis*, *S. enterica*, or *H. influenzae*. A saccharide can be a full-length, native form polysaccharide, oligosaccharide, or fragments thereof. A saccharide can be in any form that induces an immune response. A saccharide can be a capsular polysaccharide or fragment thereof. A saccharide can be from a subclass or serotype. Some non-limiting examples of saccharides from a *S. pneumoniae* serotype include, but are not limited to 1, 2, 3, 4, 5, 6A, 6B, 6C, 7F, 7C, 8, 9N, 9V, 10A, 11A, 12F, 14, 15A, 15B, 15C, 16F, 17F, 18C, 19F, 19A, 22F, 23F, 23A, 23B, 24F, 24B, 31, 33F, 33B, 34, 35F, 35B, 38, and Serogroup 20. Serogroup 20 can comprise serotype 20A and serotype 20B. *S. pneumoniae* that can produce serotype 20A polysaccharide can be identified by a mutated whaF allele as compared to the intact whaF allele of *S. pneumoniae* that can produce serotype 20B polysaccharide. TABLE 1 depicts exemplary repeat unit polysaccharide structures of various *S. pneumoniae* serotypes. FIGS. 10A, 10B, 10C, 10D, 10E, and 10F depict annotated the capsular polysaccharide (cps) locus for various *S. pneumoniae* serotypes (Bentley et al. Genetic Analysis of the Capsular Biosynthetic Locus from all 90 Pneumococcal Serotypes. *PloS Genet* 2(3): 31 (2006)).

TABLE 1

Exemplary *S. pneumoniae* Polysaccharide Serotypes

| Serotype | Polysaccharide Structure (Repeat Unit) |
|---|---|
| 1 | →3)-α-Sugp-(1→4)-α-D-GalpA-(1→3)-α-D-GalpA-(1→]$_n$ <br> Sugp: 2-acetamido-2,6-dideoxy-D-xylo-hexos-4-ulose |
| 2 | →4)-β-D-Glcp-(1→3)-α-L-Rhap-(1→3)-α-L-Rhap-(1→3)-β-L-Rhap-(1→]$_n$ <br>                                   2 <br>                                   ↓ <br>                                   1 <br> α-D-GlcpA-(1→6)-α-D-Glcp |
| 3 | →3)-β-D-GlcAp-(1→4)-β-D-Glcp-(1→]$_n$ |
| 4 | →3)-β-D-ManpNAc-(1→3)-α-L-FucpNAc-(1→3)-α-D-GalpNAc-(1→4)-α-Galp2,3(S)Pyr-(1→]$_n$ |
| 5 | →4)-β-D-Glcp-(1→4)-α-L-FucpNAc-(1→3)-β-D-Sugp-(1→]$_n$ <br>                                 3 <br>                                 ↑ <br>                                 1 <br> α-L-PnepNAc-(1-2)-β-D-GlcpA <br> L-PneNAc: 2-acetamido-2,6-dideoxy-1-talose (pneumosamine) <br> Sugp: 2-acetamido-2,6-dideoxy-D-xylo-hexos-4-ulose |
| 6A | →2)-α-D-Galp-(1→3)-α-D-Glcp-(1→3)-α-L-Rhap-(1→3)-D-Ribitool-(5→P→]$_n$ |
| 6B | →2)-α-D-Galp-(1→3)-α-D-Glcp-(1→3)-α-L-Rhap-(1→4)-D-Ribitol-(5→P→]$_n$ |
| 6C | →2)-α-D-Glcp-(1→3)-α-D-Glcp-(1→3)-α-L-Rhap-(1→3)-D-Ribitol-(5→P→]$_n$ |
| 7F | →6)-α-D-Galp-(1→3)-β-L-Rhap2Ac-(1→4)-β-D-Glcp-(1→3)-β-D-GalpNAc-(1→ <br>                2                                        4 <br>                ↑                                        ↑ <br>                1                                        1 <br> β-D-Galp                              α-D-GalpNAc-(1→2)-α-L-Rhap |

TABLE 1-continued

Exemplary *S. pneumoniae* Polysaccharide Serotypes

| Serotype | Polysaccharide Structure (Repeat Unit) |
|---|---|
| 7C | →6)-α-D-GlcpNAc-(1→2)-α-L-Rhap-(1→2)-β-L-Rhap-(1→4)-β-D-Glcp-(1→4)-α-D-GalpNAc-(1→<br>with 3↑1 branch: β-D-Ribf-(1→4)-α-L-Rhap |
| 8 | →4)-β-D-Glcp-(1→4)-α-D-Galp-(1→4)-α-D-GlcAp-(1→4)-β-D-Glcp-(1→]$_n$ |
| 9N | →4)-α-D-GlcpNAc-(1→4)-α-D-GlcpA-(1→3)-α-D-Glcp-(1→3)-β-D-ManpNAc-(1→4)-β-D-Glcp-(1→]$_n$ |
| 9V | →4)-α-D-GlcpA-(1→3)-α-D-Glcp-(1→3)-β-D-ManpNAc-(1→4)-β-D-Glcp-(1→4)-α-D-Glcp-(1→]$_n$<br>2Ac (17%) / 3Ac (25%);  4Ac (6%) / 6Ac (55%);  2Ac (3%) / 3Ac (4%) |
| 10A | Galβ1<br>↓<br>6<br>→4)-GalNAc-β-(1→3)-Gal-α-(1→2)-ribitol-5-PO$_4^-$-5Galfβ-(1→3)-Galβ-(1→]$_n$<br>3↑1 Galfβ1 |
| 11A | OAc$_{0.5}$ at 3; OAc at 2<br>→3)-β-D-Galp-(1→4)-β-D-Glcp-(1→6)-α-D-Glcp-(1→4)-α-D-Galp-(1→]$_n$<br>4↑1 PO$_4$-1-glycerol<br>0.5 OAc undeterminate |
| 12F | →4)-α-L-FucpNAc-(1→3)-β-D-GalpNAc-(1→4)-β-D-ManpNAc-(1→]<br>3↑1 α-D-Galp;  3↑1 α-D-Glcp-(1→2)-α-D-Glcp |
| 14 | →6)-β-D-GlcpNAc-(1→3)-β-D-Galp-(1→4)-β-D-Glcp-(1→]$_n$<br>4↑1 β-D-Galp |
| 15A | →3)-β-D-Galp-(1→4)-β-D-Glcp-(1→3)-α-Galp-(1→2)-β-D-Galp-(1→4)-β-D-GlcNAcp-(1→]$_n$<br>3↑ PO$_4$-1-glycerol |

TABLE 1-continued

Exemplary *S. pneumoniae* Polysaccharide Serotypes

| Serotype | Polysaccharide Structure (Repeat Unit) |
|---|---|
| 15B | →6)-β-D-GlcpNAc-(1→3)-β-D-Galp-(1→4)-β-D-Glcp-(1→]$_n$<br>        4<br>        ↑<br>        1<br>α-D-Galp-(1→2)-β-D-Galp-3-PO$_4$——R<br>80% R = H<br>20% R = choline<br>Note: On average 70% of the repeating units is O acetylated. The site of the O acetylation is unknown (Jansson et at. Carbohydr. Res. (1987) 162:111-116), although Venkateswaran et at. Infect. Dis. (1983) 147:1041-1054 suggested that it is linked to a galactose moiety. |
| 15C | →6)-β-D-GlcpNAc-(1→3)-β-D-Galp-(1→4)-β-D-Glcp-(1→]$_n$<br>        4<br>        ↑<br>        1<br>α-D-Galp-(1→2)-β-D-Galp-3-PO$_4$——R<br>80% R = H<br>20% R = choline |
| 17F | OAc<br>↓<br>2<br>-[3)-L-Rhap-β-(1→4)-D-Glcp-β-(1→3)-D-Galp-α-(1→3)-L-Rhap-β-(1→4)-L-Rhap-α-(1→2)-D-Arabinitol-1-PO$_4$→]$_n$ and<br>    4<br>    ↑<br>    4<br>    β-D-Galp<br>    OAc<br>    ↓<br>    2<br>-[3)-L-Rhap-β-(1→4)-D-Glcp-β-(1→3)-D-Galp-α-(1→3)-L-Rhap-β-(1→4)-L-Rhap-α-(1→2)-D-Arabinitol-1-PO$_4$→]$_n$<br>    1<br>    ↑<br>    4<br>    β-D-Galp |
| 18C | α-D-Glcp<br>1<br>↓<br>2<br>-[4)-β-D-Glcp-(1→4)-β-D-Galp-(1→4)-α-D-Glcp-(1→3)-α-L-Rhap-(1→]$n$<br>    3<br>    ↑<br>    PO4-1-glycerol |
| 19F | →2)-α-L-Rha-(1→5-PO$_4^-$-5→4)-β-D-ManNAc-(1→4)-β-D-Glc-(1→]$_n$ |
| 19A | →3)-α-L-Rha-(1→5-PO$_4^-$-5→4)-β-D-ManNAc-(1→4)-β-D-Glc-(1→]$_n$ |

TABLE 1-continued

Exemplary *S. pneumoniae* Polysaccharide Serotypes

Serotype  Polysaccharide Structure (Repeat Unit)

20A $\beta$-Galf
1
↓
4
→3)-$\alpha$-GlcNAcp-(1→PO$_4$→6)-$\alpha$-Glcp-(1→6)-$\beta$-Glcp-(1→3)-$\beta$-Galf-(1→3)-$\beta$-Glcp-(1→]$_n$

20B

OAc$_{0.9}$
↓
2
$\beta$-Galf
1                                              OAc$_{0.90}$
↓                                                ↓
4                                                5
→3)-$\alpha$-GlcNAcp-(1→PO$_4$→6)-$\alpha$-Glcp-(1→6)-$\beta$-Glcp-(1→3)-$\beta$-Galf-(1→3)-$\beta$-Glcp-(1→]$_n$
6                                                6
↑                                                ↑
1                                              OAc$_{0.90}$
$\alpha$-Glcp

22F

Ac
↓
2
→4)-$\beta$-D-GlcpA-(1→4)-$\beta$-L-Rhap-(1→4)-$\alpha$-D-Glcp-(1→3)-$\alpha$-D-Galf-(1→2)-$\alpha$-L-Rhap)-1→]$_n$
3
↑
$\alpha$-D-Glcp

23F $\alpha$-L-Rhap
1
↓
2
→4)-$\beta$-D-Glcp-(1→4)-$\beta$-D-Galp-(1→4)-$\beta$-L-Rhap)-(1→]$_n$
3
↑
PO$_4$-1-glycerol

23A $\alpha$-L-Rhap
1
↓
2
PO$_4$-1-glycerol-(2→P→3)-$\beta$-D-Galp-(1
↓
4
→4)-$\beta$-D-Glcp-(1→3)-$\beta$-L-Rhap)-(1→]$_n$ TABLE 1-continued Exemplary *S. pneumoniae* Polysaccharide Serotypes

| Serotype | Polysaccharide Structure (Repeat Unit) |
|---|---|
| 23B | →4)-β-D-Glcp-(1→4)-β-D-Galp-(1→4)-β-L-Rhap-(1→]$_n$<br>3<br>↑<br>\|<br>PO$_4$-1-glycerol |
| 31 | →2)-β-L-Rhap-(1→3)-β-D-Galf-(1→3)-β-Rhap-(1→4)-β-D-GlcpA-(1→3)-β-D-Galf-(1→]$_n$ |
| 33F | →3)-β-D-Galp-(1→3)-α-D-Galp-(1→3)-β-D-Galf-(1→3)-β-D-Glcp-(1→5)-β-Galf-(1→]$_n$<br>                 2                        2<br>                 ↑                        ↑<br>                 1               OAc$_{0.4}$<br>       α-D-Galp |
| 33B | Ac<br>2<br>↓<br>5)-β-D-Galf-(1→3)-β-D-Galp-NAc-(1→3)-α-D-Galp-(1→4)-Ribitol-5-P→2)-α-D-Glcp-(1→3)-β-D-Glcp-(1→]$_n$<br>                          2<br>                          ↑<br>                          1<br>                 α-D-Galp |
| 34 | →6)-Galf-β-(1→3)-Gal-α-(1→2)Rib-5-PO$_4^-$-6-Galf-β-(1→3)-Galf-β-(1→]$_n$<br>      ↓                        ↓<br>    2OAc             3,5OAc |
| 34 | →3)-β-D-Galf-(1→3)-α-D-Glcp-(1→2)-β-D-Galf6Ac$_{0.5}$-(1→3)-α-D-Galp-(1→2)-D-Rib-ol-(5→P→ |
| 35F | →6)-Galf-β-(1→3)-Gal-α-(1→2)Rib-5-PO$_4^-$-3-Galf-β-(1→3)-Gal-β-1→]$_n$<br>      ↓<br>    2OAc |
| 35B | OAc$_{0.7}$<br>↓<br>2<br>→4)-β-D-GalpNAc-(1→6)-β-D-Galf-(1→3)-β-D-Glcp-(1→6)-β-D-Galf-(1→1)-Rib-(5-PO$_4$→]$_n$ |

Saccharides can be isolated from bacteria. Saccharides can be isolated from bacteria and then conjugated to a polypeptide to form a saccharide-polypeptide conjugate. Any method for isolating the unconjugated polysaccharide can be used. For example, a polysaccharide serotype can be grown in a soy-based medium. The individual polysaccharides can then be purified by steps including centrifugation, precipitation, and ultra-filtration. See U.S. Patent Application Publication No. 2008/028638 and U.S. Pat. No. 5,847,112. Other processes for purifying polysaccharides are described in U.S. Pat. Nos. 4,686,102; 4,242,501; 4,221,906; 5,623,057; and 5,847,112. Alternatively or additionally, polysaccharides may be isolated simultaneously from more than one serotype, which can produce a mixture of polysaccharide serotypes with the desired polysaccharide already combined. Furthermore, these isolated polysaccharides can be sized by microfluidization. The polysaccharides can be sized in order to reduce viscosity in polysaccharide samples and/or to improve filterability for conjugated sample. A saccharide-polypeptide conjugate can include a saccharide or a fragment thereof which is at least partially embedded in one or more polypeptides. The one or more polypeptides can have one or more crosslinks. The at least partially embedded saccharide or fragment thereof can, but need not be, covalently bound to at least one of the polypeptides when at least partially embedded therein.

Any of the *S. pneumoniae* strains for isolating and purifying the polysaccharides as described herein can be provided by either the CDC, United States or CCUG, Gothenburg. Alternatively, any of the polysaccharides described herein can be isolated and purified from any source (e.g., any laboratory) in which serotyping or other genetic sequencing is used to identify the unique strain from which the polysaccharides are isolated and purified. A vial of a strain of *S. pneumoniae* can be seeded and then can be grown overnight on an agar plate. A single colony can be picked from this plate and streaked onto a new agar plate for overnight growth. This process can be repeated three times to purify the strain before a flask can be seeded and incubated. After allowing the seeded flask sufficient time for growth, the flask contents can be harvested by centrifugation. The centrifugation product can be resuspended in a medium of about 20% glycerol and then can be dispensed into cryogenic vials. The cell bank can be contained in the cryogenic vials, which can be stored at −70° C. until use. The cell bank of the strain can then be used for isolation and purification of the polysaccharides of that strain using a fermentation process.

Polysaccharides of a S. pneumoniae strain can be isolated and purified from a cell bank of a strain. The strain can be provided by either the CDC, United States or CCUG, Gothenburg, and then can be used to produce a cell bank as described above. Alternatively, strain can be provided by any source (e.g., any laboratory) in which serotyping or other genetic sequencing is used to identify the serotype of the strain. A vial of a cell bank can be produced as described above is used to inoculate a flask, which is allowed to grow overnight. This culture is used to seed a new culture for fermentation in a fermenter. The culture is allowed to grow under the appropriate conditions for that strain. After fermentation, the cells are inactivated and then are treated with deoxycholate to break open the cells and release the capsular polysaccharide. Subsequently, debris is removed by centrifugation, which is followed by a depth filter step through a 0.45 μm filter and the cell free broth is collected. The product is then purified and the polysaccharide size is determined. Quality control tests are performed on the product, such as a purity assay and confirmation of strain inactivation (no growth after plating). Any polysaccharides described herein can be isolated and purified using this method.

The saccharides or polysaccharides of the invention are depolymerized (sized) to a final range from 100-500 kDa.

Saccharides that can be used in the saccharide-polypeptide conjugate can also be obtained from commercial sources. For example, individual polysaccharide serotypes can be obtained in a powder form. These polysaccharides can be dissolved in water and incubated with a salt to dissociate residual impurities, which can then be removed by a filtration step. The purified polysaccharides serotypes can then be conjugated to a polypeptide.

A polypeptide of an immunogenic saccharide-polypeptide conjugate can be an oligopeptide. A polypeptide of can be a carrier protein. A polypeptide can be any polypeptide that allows for conjugation or coupling of saccharide and results in the display of the conjugate or coupling in a way that induces a protective immune response against the saccharide. A polypeptide can be any polypeptide that allows for conjugation or coupling of a capsular polysaccharide or fragment of the capsular polysaccharide and can result in the display of the conjugate or coupling in a way that can induce a protective immune response against the capsular polysaccharide or fragment of the capsular polysaccharide. A polypeptide can be $CRM_{197}$, tetanus toxoid, a diphtheria toxoid, a cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B *streptococcus*, a non-typable *H. influenzae* P4 protein, a non-typable *H. influenzae* P6 protein, *M catarrhalis* uspA, a keyhole limpet haemocyanin (KLH), OMPC from *N. meningitidis*, the purified protein derivative of tuberculin (PPD), protein D from *H. influenzae*, PspA, or any fragment thereof. The polypeptide can be a polypeptide in which the toxin activity of the polypeptide can be at least partially mitigated. Examples of suitable polypeptides for use as in a saccharide-polypeptide conjugate are described in U.S. Pat. No. 8,808,707 and can include: polylysine, polyglutamic acid, polyaspartic acid, co-polymers thereof, and mixed polymers of these amino acids and others, e.g., serines, threonines, or tyrosines, to confer desirable solubility properties on the resultant loaded carrier and conjugate. A polypeptide can be a $CRM_{197}$ with 100% sequence homology with GAD-DVVDSSKSFVMENFSSYHGTKPGYVD-SIQKGIQKPKSGTQGNYDDDWKEFYST DNKYDAAGYSVDNENPLSGKAGGVVKV-TYPGLTKVLALKVDNAETIKKELGLSLTE PLMEQVG-TEEFIKRFGDGASRVVLSLPFAEGSSS-VEYINNWEQAKALSVELEINFETR GKRGQDAMYEYMAQACAG-NRVRRSVGSSLSCINLDWDVIRDKTKTKIESLKEHGPI KNKMSESPNKTVSEEKAKQYLEEFHQTALEH-PELSELKTVTGTNPVFAGANYAAWA VNVAQVID-SETADNLEKTTAALSILPGIGSVMGIADGAVHHNTEE-IVAQSIALSSLMV AQAIPLVGELVDIGFAAYNFVESIINLFQVVHNSYNR-PAYSPGHKTQPFLHDGYAVS WNTVED-SIIRTGFQGESGHDIKITAENTPLPIAGVLLP-TIPGKLDVNKSKTHISVNGRKI RMRCRAIDGDVTFCRPK-SPVYVGNGVHANLHVAFHRSSSEKIHS-NEISSDSIGVLGYQ KTVDHTKVNSKLSLFFEIKS (SEQ ID NO: 1). A polypeptide can be a $CRM_{197}$ with at least 80%, 90%, 95%, or 98% sequence homology with SEQ ID NO: 1. A polypeptide can be a modified $CRM_{197}$ as disclosed in U.S. Pat. No. 9,359,400. A polypeptide can be $CRM_{197}$ with non-natural amino acid substitutions as disclosed in U.S. Pat. No. 9,764,039.

Moreover, suitable polypeptide carriers can include bacterial toxins, toxoids, or inactivated toxin. A toxoid can be a bacterial toxin whose toxicity has been weakened or suppressed while other properties, typically immunogenicity, are maintained. As a class, bacterial toxins and derivatives thereof can to be highly immunogenic. Polypeptides derived from bacterial toxins can be effective at eliciting an immune response to saccharides of the conjugate. Steps can be taken (e.g., by chemical and/or genetic means) to render the toxins non-toxic and safe for administration to mammals. Examples of such bacterial toxin-derived polypeptides which may currently commonly used in vaccine compositions, and can be used in the immunogenic saccharide-polypeptide conjugate described herein, include the diphtheria and tetanus toxoids, and variants thereof (e.g., DT, $CRM_{197}$, TT), cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B *streptococcus*, non-typable *H. influenzae* P4 protein, non-typable *H. influenzae* P6 protein, *M catarrhalis* uspA, keyhole limpet haemocyanin (KLH), OMPC from *N. meningitidis*, the purified protein derivative of tuberculin (PPD), protein D from *H. influenzae*, PspA, or any fragment thereof. Polypeptide fragments can be used to elicit a protective immune response against the capsular polysaccharide or fragment of the capsular polysaccharide of the immunogenic saccharide-polypeptide conjugate. These fragments can encompass T-helper epitopes.

$CRM_{197}$ is a non-toxic mutant of diphtheria toxin with a single amino acid substitution of glutamic acid for glycine at position 52, with the amino acid sequence of GAD-DVVDSSKSFVMENFSSYHGTKPGYVD-SIQKGIQKPKSGTQGNYDDDWKEFYST DNKYDAAGYSVDNENPLSGKAGGVVKV- TYPGLTKVLALKVDNAETIKKELGLSLTE PLMEQVG-
TEEFIKRFGDGASRVVLSLPFAEGSSS-
VEYINNWEQAKALSVELEINFETR
GKRGQDAMYEYMAQACAG-
NRVRRSVGSSLSCINLDWDVIRDKTKTKIESLKEHGPI
KNKMSESPNKTVSEEKAKQYLEEFHQTALEH-
PELSELKTVTGTNPVFAGANYAAWA VNVAQVID-
SETADNLEKTTAALSILPGIGSVMGIADGAVHHNTEE-
IVAQSIALSSLMV
AQAIPLVGELVDIGFAAYNFVESIINLFQVVHNSYNR-
PAYSPGHKTQPFLHDGYAVS WNTVED-
SIIRTGFQGESGHDIKITAENTPLPIAGVLLP-
TIPGKLDVNKSKTHISVNGRKI
RMRCRAIDGDVTFCRPK-
SPVYVGNGVHANLHVAFHRSSSEKIHS-
NEISSDSIGVLGYQ KTVDHTKVNSKLSLFFEIKS (SEQ ID NO: 1). $CRM_{197}$ can be from 58-59 kDa in size. $CRM_{197}$ can be 58.4 kDa in size. $CRM_{197}$ can be produced, isolated, and purified from a cell bank. A vial from a cell bank of $CRM_{197}$ can be used to seed a new flask and allowed to ferment. The fermentation culture can be centrifuged and the contents can be harvested, clarified, and filtered using a 0.2 μm filter. The filtrate can then be concentrated and diafiltered. The $CRM_{197}$ can be further purified by filtration using microtubes or membranes of the appropriate pore size. Then anion exchange chromatography can be used in the isolation and purification of the $CRM_{197}$, which can be followed by ammonium sulfate precipitation, and another filtration using a 0.45 μm filter. $CRM_{197}$ can be further isolated and purified from this product by hydrophobic interaction chromatography, after which $CRM_{197}$ can be concentrated and diafiltered into the desired buffer. A final step can be filtration with 0.2 μm filter. The isolated and purified $CRM_{197}$ can be stored at ≤−70° C. until use in conjugation with a saccharide or polysaccharide. Quality control tests can be performed on the isolated and purified $CRM_{197}$.

A polypeptide can be conjugated to an immunogenic serotype 1 capsular polysaccharide, fragment thereof, or combination thereof isolated from *S. pneumoniae*. A polypeptide can be conjugated to an immunogenic serotype 2 capsular polysaccharide, fragment thereof, or combination thereof isolated from *S. pneumoniae*. A polypeptide can be conjugated to an immunogenic serotype 3 capsular polysaccharide, fragment thereof, or combination thereof isolated from *S. pneumoniae*. A polypeptide can be conjugated to an immunogenic serotype 4 capsular polysaccharide, fragment thereof, or combination thereof isolated from *S. pneumoniae*. A polypeptide can be conjugated to an immunogenic serotype 5 capsular polysaccharide, fragment thereof, or combination thereof isolated from *S. pneumoniae*. A polypeptide can be conjugated to an immunogenic serotype 6A capsular polysaccharide, fragment thereof, or combination thereof isolated from *S. pneumoniae*. A polypeptide can be conjugated to an immunogenic serotype 6B capsular polysaccharide, fragment thereof, or combination thereof isolated from *S. pneumoniae*. A polypeptide can be conjugated to an immunogenic serotype 6C capsular polysaccharide, fragment thereof, or combination thereof isolated from *S. pneumoniae*. A polypeptide can be conjugated to an immunogenic serotype 7F capsular polysaccharide, fragment thereof, or combination thereof isolated from *S. pneumoniae*. A polypeptide can be conjugated to an immunogenic serotype 7C capsular polysaccharide, fragment thereof, or combination thereof isolated from *S. pneumoniae*. A polypeptide can be conjugated to an immunogenic serotype 8 capsular polysaccharide, fragment thereof, or combination thereof isolated from *S. pneumoniae*. A polypeptide can be conjugated to an immunogenic serotype 9N capsular polysaccharide, fragment thereof, or combination thereof isolated from *S. pneumoniae*. A polypeptide can be conjugated to an immunogenic serotype 9V capsular polysaccharide, fragment thereof, or combination thereof isolated from *S. pneumoniae*. A polypeptide can be conjugated to an immunogenic serotype 10A capsular polysaccharide, fragment thereof, or combination thereof isolated from *S. pneumoniae*. A polypeptide can be conjugated to an immunogenic serotype 11A capsular polysaccharide, fragment thereof, or combination thereof isolated from *S. pneumoniae*. A polypeptide can be conjugated to an immunogenic serotype 12F capsular polysaccharide, fragment thereof, or combination thereof isolated from *S. pneumoniae*. A polypeptide can be conjugated to an immunogenic serotype 14 capsular polysaccharide, fragment thereof, or combination thereof isolated from *S. pneumoniae*. A polypeptide can be conjugated to an immunogenic serotype 15A capsular polysaccharide, fragment thereof, or combination thereof isolated from *S. pneumoniae*. A polypeptide can be conjugated to an immunogenic serotype 15B capsular polysaccharide, fragment thereof, or combination thereof isolated from *S. pneumoniae*. A polypeptide can be conjugated to an immunogenic serotype 15C capsular polysaccharide, fragment thereof, or combination thereof isolated from *S. pneumoniae*. A polypeptide can be conjugated to an immunogenic serotype 16F capsular polysaccharide, fragment thereof, or combination thereof isolated from *S. pneumoniae*. A polypeptide can be conjugated to an immunogenic serotype 17F capsular polysaccharide, fragment thereof, or combination thereof isolated from *S. pneumoniae*. A polypeptide can be conjugated to an immunogenic serotype 18C capsular polysaccharide, fragment thereof, or combination thereof isolated from *S. pneumoniae*. A polypeptide can be conjugated to an immunogenic serotype 19A capsular polysaccharide, fragment thereof, or combination thereof isolated from *S. pneumoniae*. A polypeptide can be conjugated to an immunogenic serotype 19F capsular polysaccharide, fragment thereof, or combination thereof isolated from *S. pneumoniae*. A polypeptide can be conjugated to an immunogenic serotype 20A capsular polysaccharide, fragment thereof, or combination thereof isolated from *S. pneumoniae*. A polypeptide can be conjugated to an immunogenic serotype 20B capsular polysaccharide, fragment thereof, or combination thereof isolated from *S. pneumoniae*. A polypeptide can be conjugated to an immunogenic serotype 22F capsular polysaccharide, fragment thereof, or combination thereof isolated from *S. pneumoniae*. A polypeptide can be conjugated to an immunogenic serotype 23A capsular polysaccharide or fragment thereof isolated from *S. pneumoniae*. A polypeptide can be conjugated to an immunogenic serotype 23B capsular polysaccharide, fragment thereof, or combination thereof isolated from *S. pneumoniae*. A polypeptide can be conjugated to an immunogenic serotype 23F capsular polysaccharide, fragment thereof, or combination thereof isolated from *S. pneumoniae*. A polypeptide can be conjugated to an immunogenic serotype 24F capsular polysaccharide, fragment thereof, or combination thereof isolated from *S. pneumoniae*. A polypeptide can be conjugated to an immunogenic serotype 24B capsular polysaccharide, fragment thereof, or combination thereof isolated from *S. pneumoniae*. A polypeptide can be conjugated to an immunogenic serotype 31 capsular polysaccharide, fragment thereof, or combination thereof isolated from *S. pneumoniae*. A polypeptide can be conjugated to an immunogenic serotype 33F capsular polysaccharide, fragment thereof, or combination thereof isolated from *S. pneumoniae*. A polypeptide can be conjugated to an immunogenic serotype 33B capsular polysaccharide, fragment thereof, or combination thereof isolated from *S. pneumoniae*. A polypeptide can be conjugated to an immunogenic serotype 34 capsular polysaccharide, fragment thereof, or combination thereof isolated from *S. pneumoniae*. A polypeptide can be conjugated to an immunogenic serotype 35F capsular polysaccharide, fragment thereof, or combination thereof isolated from *S. pneumoniae*. A polypeptide can be conjugated to an immunogenic serotype 35B capsular polysaccharide, fragment thereof, or combination thereof isolated from *S. pneumoniae*. A polypeptide can be conjugated to an immunogenic serotype 38 capsular polysaccharide, fragment thereof, or combination thereof isolated from *S. pneumoniae*.

In some embodiments, $CRM_{197}$ can be conjugated to an immunogenic serotype 1 capsular polysaccharide, fragment thereof, or combination thereof isolated from *S. pneumoniae*. $CRM_{197}$ can be conjugated to an immunogenic serotype 2 capsular polysaccharide, fragment thereof, or combination thereof isolated from *S. pneumoniae*. $CRM_{197}$ can be conjugated to an immunogenic serotype 3 capsular polysaccharide, fragment thereof, or combination thereof isolated from *S. pneumoniae*. $CRM_{197}$ can be conjugated to an immunogenic serotype 4 capsular polysaccharide, fragment thereof, or combination thereof isolated from *S. pneumoniae*. $CRM_{197}$ can be conjugated to an immunogenic serotype 5 capsular polysaccharide, fragment thereof, or combination thereof isolated from *S. pneumoniae*. $CRM_{197}$ can be conjugated to an immunogenic serotype 6A capsular polysaccharide, fragment thereof, or combination thereof isolated from *S. pneumoniae*. $CRM_{197}$ can be conjugated to an immunogenic serotype 6B capsular polysaccharide, fragment thereof, or combination thereof isolated from *S. pneumoniae*. $CRM_{197}$ can be conjugated to an immunogenic serotype 6C capsular polysaccharide, fragment thereof, or combination thereof isolated from *S. pneumoniae*. $CRM_{197}$ can be conjugated to an immunogenic serotype 7F capsular polysaccharide, fragment thereof, or combination thereof isolated from *S. pneumoniae*. $CRM_{197}$ can be conjugated to an immunogenic serotype 7C capsular polysaccharide, fragment thereof, or combination thereof isolated from *S. pneumoniae*. $CRM_{197}$ can be conjugated to an immunogenic serotype 8 capsular polysaccharide, fragment thereof, or combination thereof isolated from *S. pneumoniae*. $CRM_{197}$ can be conjugated to an immunogenic serotype 9N capsular polysaccharide, fragment thereof, or combination thereof isolated from *S. pneumoniae*. $CRM_{197}$ can be conjugated to an immunogenic serotype 9V capsular polysaccharide, fragment thereof, or combination thereof isolated from *S. pneumoniae*. $CRM_{197}$ can be conjugated to an immunogenic serotype 10A capsular polysaccharide, fragment thereof, or combination thereof isolated from *S. pneumoniae*. $CRM_{197}$ can be conjugated to an immunogenic serotype 11A capsular polysaccharide, fragment thereof, or combination thereof isolated from *S. pneumoniae*. $CRM_{197}$ can be conjugated to an immunogenic serotype 12F capsular polysaccharide, fragment thereof, or combination thereof isolated from *S. pneumoniae*. $CRM_{197}$ can be conjugated to an immunogenic serotype 14 capsular polysaccharide, fragment thereof, or combination thereof isolated from *S. pneumoniae*. $CRM_{197}$ can be conjugated to an immunogenic serotype 15A capsular polysaccharide, fragment thereof, or combination thereof isolated from *S. pneumoniae*. $CRM_{197}$ can be conjugated to an immunogenic serotype 15B capsular polysaccharide, fragment thereof, or combination thereof isolated from *S. pneumoniae*. $CRM_{197}$ can be conjugated to an immunogenic serotype 15C capsular polysaccharide, fragment thereof, or combination thereof isolated from *S. pneumoniae*. $CRM_{197}$ can be conjugated to an immunogenic serotype 16F capsular polysaccharide, fragment thereof, or combination thereof from *S. pneumoniae*. $CRM_{197}$ can be conjugated to an immunogenic serotype 17F capsular polysaccharide, fragment thereof, or combination thereof isolated from *S. pneumoniae*. $CRM_{197}$ can be conjugated to an immunogenic serotype 18C capsular polysaccharide, fragment thereof, or combination thereof isolated from *S. pneumoniae*. $CRM_{197}$ can be conjugated to an immunogenic serotype 19A capsular polysaccharide, fragment thereof, or combination thereof isolated from *S. pneumoniae*. $CRM_{197}$ can be conjugated to an immunogenic serotype 19F capsular polysaccharide, fragment thereof, or combination thereof isolated from *S. pneumoniae*. $CRM_{197}$ can be conjugated to an immunogenic serotype 20A capsular polysaccharide, fragment thereof, or combination thereof isolated from *S. pneumoniae*. $CRM_{197}$ can be conjugated to an immunogenic serotype 20B capsular polysaccharide, fragment thereof, or combination thereof isolated from *S. pneumoniae*. $CRM_{197}$ can be conjugated to an immunogenic serotype 22F capsular polysaccharide, fragment thereof, or combination thereof isolated from *S. pneumoniae*. $CRM_{197}$ can be conjugated to an immunogenic serotype 23A capsular polysaccharide, fragment thereof, or combination thereof isolated from *S. pneumoniae*. $CRM_{197}$ can be conjugated to an immunogenic serotype 23B capsular polysaccharide, fragment thereof, or combination thereof isolated from *S. pneumoniae*. $CRM_{197}$ can be conjugated to an immunogenic serotype 23F capsular polysaccharide, fragment thereof, or combination thereof isolated from *S. pneumoniae*. $CRM_{197}$ can be conjugated to an immunogenic serotype 24F capsular polysaccharide, fragment thereof, or combination thereof isolated from *S. pneumoniae*. $CRM_{197}$ can be conjugated to an immunogenic serotype 24B capsular polysaccharide, fragment thereof, or combination thereof isolated from *S. pneumoniae*. $CRM_{197}$ can be conjugated to an immunogenic serotype 31 capsular polysaccharide, fragment thereof, or combination thereof isolated from *S. pneumoniae*. $CRM_{197}$ can be conjugated to an immunogenic serotype 33F capsular polysaccharide, fragment thereof, or combination thereof isolated from *S. pneumoniae*. $CRM_{197}$ can be conjugated to an immunogenic serotype 33B capsular polysaccharide, fragment thereof, or combination thereof isolated from *S. pneumoniae*. $CRM_{197}$ can be conjugated to an immunogenic serotype 34 capsular polysaccharide, fragment thereof, or combination thereof isolated from *S. pneumoniae*. $CRM_{197}$ can be conjugated to an immunogenic serotype 35F capsular polysaccharide, fragment thereof, or combination thereof isolated from *S. pneumoniae*. $CRM_{197}$ can be conjugated to an immunogenic serotype 35B capsular polysaccharide, fragment thereof, or combination thereof isolated from *S. pneumoniae*. $CRM_{197}$ can be conjugated to an immunogenic serotype 38 capsular polysaccharide, fragment thereof, or combination thereof isolated from *S. pneumoniae*.

In further embodiments, any of the saccharides as described herein can be conjugated to any polypeptides described herein. Any of the immunogenic saccharide-polypeptide conjugates described herein can be isolated and purified.

Methods of Conjugating a Saccharide and Polypeptide to Produce a Saccharide-Polypeptide Conjugate The saccharides can be conjugated to the polypeptide by, e.g., chemical or biological synthesis. A saccharide can be a polysaccharide, a capsular polysaccharide, or an immunogenic fragment thereof. A capsular polysaccharide or fragment of the capsular polysaccharide can be conjugated to the polypeptide by chemical or biological synthesis.

For example, the capsular polysaccharide or immunogenic fragment thereof can be chemically activated and then reacted with the polypeptide. For example, capsular polysaccharides or fragments of the capsular polysaccharides can be reacted with either ammonia or diaminoethane to generate a free terminal amino group. The amino group can then be reacted with an excess of disuccinimidyl ester of adipic acid, which can introduce an active succininmidyl ester group. This can then be reacted to a free amino group on the polypeptide to form covalent amide bonds.

A polysaccharide and polypeptide can be conjugated using 1-cyano-dimethylaminopyridinium tetrafluoroborate (CDAP) chemistry. CDAP can be used to activate a broad range of acidic, neutral, and other classes of polysaccharides, which can then be derivatized with diamines, dihydrazides or other functional groups in preparation for coupling to proteins. In CDAP, the cynanylating reagent 1-cyano-dimethylaminopyridinium tetrafluoroborate can be used for the synthesis of polysaccharide-protein conjugates. The cyanilation reaction can be performed under relatively mild conditions, which can avoid hydrolysis of the alkaline sensitive polysaccharides. This synthesis can allow for direct coupling to a carrier. The polysaccharide can be solubilized in water or a saline solution. CDAP can be dissolved in acetonitrile and can be added immediately to the polysaccharide solution. The CDAP can reacts with the hydroxyl groups of the polysaccharide to form a cyanate ester. This cyanate ester can be highly reactive, which can result in an activated polysaccharide. This can be done at a pH of 9-10. After this activation step, the polypeptide can be added. Amino groups of lysine of a polypeptide can react with the activated polysaccharide to form an isourea covalent link. This conjugation step can occur under mildly alkaline conditions, such as a pH of 7-9. In some cases, there can be a strong pH dependence on the epsilon amines of lysine to form a stable O-alkyl-isourea linkage. After the coupling reaction, a large excess of an amino-containing reagent such as glycine can then be added to quench the residual activated functional groups. The CDAP activation can take only a few minutes and conjugation can be completed in a few hours. The conjugate can then be passed through a gel permeation column to remove unreacted polypeptide and residual reagents.

In some embodiments, CDAP can be made up at 100 mg/ml in acetonitrile and stored at −20° C. for up to 1 month. CDAP can be slowly pipetted into a vortexed solution of polysaccharide in water (rapid addition of the organic co-solvent precipitates the polysaccharide) and 20 s later a volume of aqueous 0.2M triethylamine (TEA) equal to volume of CDAP used can be added. At 2.5 min, a large molar excess of a 0.5 M hexanediamine solution in either 0.1 M sodium borate at pH 9.3 or 0.75 M HEPES at pH 7.5, can be added. The reaction mixture can be allowed to stand overnight at 4° C., can be desalted on either a P-6 DG or a P-6 cartridge, can be equilibrated with saline and then can be further dialyzed into saline. The extent of derivatization with hexanediamine can be determined using a TNBS assay for primary amines; absorbance can be measured at 366 nm, using an extinction coefficient of 11000 $M^{-1}$. Polysaccharide concentrations can be determined as described by Monsigny et al., using the corresponding polysaccharide as the standard.

In some embodiments, polysaccharide can be solubilized in saline at 10 mg/ml. At t=0, CDAP (100 mg/ml in acetonitrile) can be added (1 mg CDAP/mg polysaccharide) while vortexing. At 30 s, 0.2 M TEA can be added (10 µl/mg polysaccharide) to raise the pH. At 2.5 min the pH can be readjusted to the coupling pH and the amine or hydrazide reagent or the polypeptide can be added, in the appropriate buffer. After an overnight reaction, the solution can be dialyzed and/or desalted on a P6DG column. Polysaccharide polypeptide conjugates can be fractionated on an S400HR column, which can be equilibrated with either saline or PBS. HPLC can be performed on HPLC size exclusion columns using a Waters 626 pump, monitored at 280 nm and with a refractive index detector. Samples can be filtered before chromatography using a Millex Ultrafree MC device.

In some embodiments, for low pH coupling, amines on polypeptide can be functionalized with hydrazides using the two-step method as follows. Five mg of polypeptide at 12.5 mg/ml in 0.19 M HEPES, 2.5 mM EDTA, pH 7.3 can be iodoacetylated by the addition of a 15-fold molar excess of SIA over moles of polypeptide. After 2 h reaction in the dark, the solution can be desalted on a 1×15 cm P6DG column, can be equilibrated with 2 mM MES, 0.2 M NaCl, pH 5.9 and the void volume fractions, which can be concentrated with a Centricon 50 device. DTPH (30 µl) at 0.1 M in water, can be reduced to 3-mercapto-propionyl hydrazide by addition of 25 µl 0.1 M TCEP in water, and can then be added to the iodoacetylated polypeptide with a pH that can be adjusted to about 5. After a 2 h reaction, reagent can be removed by desalting again and concentrating with a Centricon 50 device to 10 mg/ml. TNBS can be used to determined number of hydrazide per moles of polypeptide. To couple the hydrazide-derivatized polypeptide, 3 mg of polysaccharide at 10 mg/ml in saline can be activated by the addition of 15 µl CDAP at 100 mg/ml in acetonitrile, followed 30 s later by 30 µl of 0.2 M TEA. At 2.5 min, the pH can be reduced to 5.5 by the addition of 100 µl 1 M MES, pH 5.5 and the activated polysaccharide can be added to 3.8 mg of the polypeptide-hydrazide. After an overnight reaction at 4° C., the reaction can be quenched by the addition of 50 µl 1 M ethanolamine. The solution can be applied to an S400HR column, which can be equilibrated with PBS, and the void volume fractions can be pooled. Sterile filtration can be done by passage through a Millex GB 0.2 µm filter.

In some embodiments, CDAP can be used to conjugate a polysaccharide and $CRM_{197}$. The polysaccharide (10 mg) can be dissolved in 1.0 mL of 0.1M sodium borate buffer pH 9.0 and can be activated by addition of 50 µl of a solution of CDAP dissolved in acetone:water (6:4). Immediately, the pH can be adjusted and maintained at 9.0 by continuous dropwise addition of a 0.1 M NaOH solution. The mixture can be stirred for 5 min and then a volume of 1.4 mL of 0.05 M HCl can be added, stirred for a while and then left to rest during 1½ min more. The mixture can be rapidly passed through a PD-10 column equilibrated in 0.1 M sodium bicarbonate buffer pH 8.3. An aliquot of this can be used to determine cyanate ester formation and the rest of the preparation can be immediately used for coupling purposes. Polypeptide (15 mg) can be dissolved in 1.0 mL of 0.1 M $NaHCO_3$ buffer pH 8.3 and added to the activated polysaccharide solution. The mixture can be gently stirred during 8 h at room temperature. A volume of 1.0 mL 0.1 M Tris-HCl buffer pH 8.6 can be added to block any remaining activation sites on the unreacted polysaccharide and incubated during 1 h more. The final solution can be lyophilized and stored until used for the purification procedure. The progress of the conjugation can be analyzed by high-performance size exclusion chromatography (HPSEC) using a Zorbax GF-250 column and monitored at 280 nm and 210 nm. For example, aliquots of the reaction mixture can be taken at 10 min and at every hour up to 4 h. The column can be equilibrated in 0.025 M phosphate buffer pH 7.0 supplemented with 0.13 M NaCl and be calibrated with the following proteins: thyroglobulin (669 kDa), ferritin (440 kDa), catalase (232 kDa), aldolase (158 kDa), BSA (67 kDa), ovalbumin (43 kDa), and ribonuclease (13.7 kDa). The void volume can be determined with Blue dextran. Samples (10 µl aliquots) can be injected into the column and a flow rate of 0.5 mL/min can be used. Prior and after the analysis the column can be washed with the equilibration buffer. The conjugation reaction progress (%) can be measured by comparing the conjugate peak area related to the free protein peak area using detection at wavelength 280 nm according to the following equation: (conjugate peak area/(conjugate peak area+free protein peak area))×100.

In some embodiments, the polysaccharide can be activated via CDAP chemistry in a CDAP solution. The polysaccharide can be mixed with CDAP solution, which can then be incubated at the appropriate temperature for polysaccharide activation. A calculated amount of $CRM_{197}$ can be added to the activated polysaccharides. The reaction can then be quenched using glycine or any other suitable quenching reagent. The conjugation reaction mixture can be filtered, diafiltered, and concentrated for the polysaccharide-$CRM_{197}$ conjugates. The polysaccharide-$CRM_{197}$ conjugates can then be purified by gel filtration chromatography. The fractions containing the polysaccharide-$CRM_{197}$ conjugates can be pooled, concentrated, and then filtered through a 0.2 µm filter. The product can be stored at 2-8° C.

As another example, the capsular polysaccharide or immunogenic fragment thereof can activated by periodate oxidation. Sodium periodate oxidizes diols (two adjacent carbons with hydroxyl groups) can be converted into aldehydes (C=O) and in the process breaks C—C bonds. Thus, depending upon the structure, periodate activation can fragment a capsular polysaccharide or immunogenic fragment thereof and open the ring structures of sugars. When the diol is within a ring, the ring sugar can be opened possibly altering the polysaccharide conformation. When the diol is in a glycerol or ribitol side chain, the side chain can disappear. The reactive aldehyde groups can then condense with free amino groups on the polypeptide in the presence of sodium cyanoborohydride to form a stable secondary amine. Condensation of the aldehyde with the epsilon amino group on lysine can be a slow process and can take a few days. The remaining aldehyde groups can then be quenched using sodium borohydride, which can convert them back to hydroxyls.

Another example of coupling a polypeptide to a polysaccharide is based on thioether bonding of polysaccharides activated with 2-iminothiolane (2-IT), or alternatively, with cystamine, to bromoacetylated polypeptides such as tetanus toxoid.

Schematic I

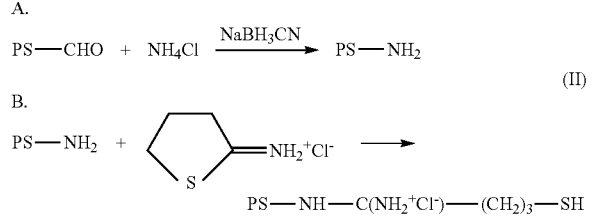

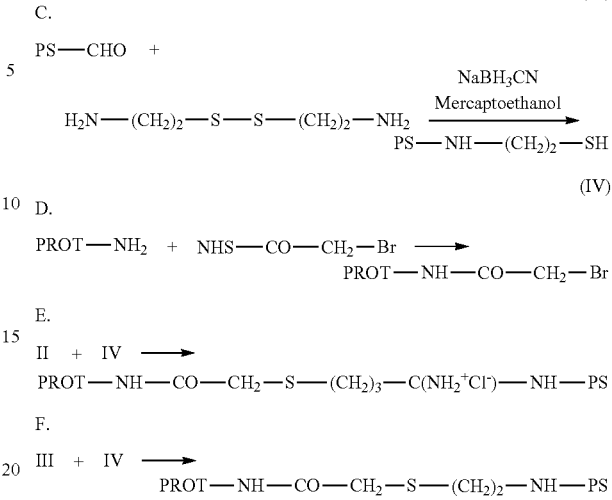

The above Schematic I represents end-point coupling of polysaccharides (PS) to proteins (PROT) through thioether bond. (A) Amination of polysaccharide through reducing terminal using ammonium chloride in the presence of cyanoborohydride ion. (B) Thiolation of aminated polysaccharide (I) with 2-iminothiolane (2-IT). (C) Alternative thiolation of polysaccharide through reductive amination with cystamine with concomitant cleavage of disulfide bond. (D) Bromoacetylation of amino groups of protein using N-hydroxysuccimidyl bromoacetate. (E) Coupling of polysaccharide derivatized with 2-IT (II) to bromoacetylated protein (IV). (F) Alternative coupling of polysaccharide derivatized with cystamine (III) to bromoacetylated protein (IV).

As another example, the immunogenic saccharide-polypeptide conjugate can be produced using bacteria, such as Escherichia coli (E. coli). The immunogenic saccharide-polypeptide can comprise the capsular polysaccharide at least partially embedded in the polypeptide. The immunogenic saccharide-polypeptide can comprise the capsular polysaccharide chemically cross-linked to the polypeptide. The immunogenic saccharide-polypeptide can comprise the capsular polysaccharide at least partially chemically cross-linked to the polypeptide. A capsular polysaccharide or fragment of the capsular polysaccharide of a serotype from S. pneumoniae can be conjugated to a polypeptide by chemical or biological synthesis. One saccharide can be conjugated to one polypeptide. Two or more saccharides can be conjugated to one polypeptide. The saccharides can be the same serotype. The saccharides can be different serotypes. One capsular polysaccharide or immunogenic fragment thereof can be conjugated to one polypeptide. Two or more capsular polysaccharides or fragments thereof can be conjugated to one polypeptide. The capsular polysaccharides or fragments thereof can be the same serotype. The capsular polysaccharides or fragments thereof can be different serotypes.

After conjugation, the polysaccharide polypeptide conjugate can be purified. For example, different chromatographic strategies can be used to purify a polysaccharide-polypeptide conjugate: SEC (using a column packed with Sepharose CL-6B), a combination of ion-exchange chromatography (DEAE-Sepharose) can be followed by HPSEC (Sepharose CL-6B and hydrophobic interaction chromatography (HIC) (column packed with Sephadex LH-20). For HPSEC purification on a Sepharose CL-6B column, an amount of 4.0 mg of the lyophilized mixture containing the polysaccharide polypeptide conjugate, free polysaccharide and free polypeptide, can be dissolved in 0.1 M formic acid buffer (ammonium salt) pH 6.0 and can be applied to the column (60 cm×4.0 cm) equilibrated with the same buffer, at a flow of 0.5 mL/min. Isocratic elution can be performed with the buffer, and the process can be continuously monitored using a differential refractometric detector. Fractions can be collected, can be lyophilized, and can be used for further analysis. For the second strategy, an amount of 4.0 mg of the lyophilized reaction mixture can be dissolved in 500 µL of 0.1 M phosphate-buffered saline (PBS) pH 7.0 and can be applied to the DEAE-Sepharose column, previously equilibrated in the same buffer. The pass-through of the column can be collected and after washing with the buffer, elution can be performed using a gradient (0.25-1.0 M) of NaCl. The presence of the polysaccharide can be analyzed in each fraction by the Phenol sulfuric technique. The eluted fractions can be pooled, can be lyophilized, can be resuspended in 0.1 M ammonium formate buffer pH 6.0, and can be applied to a Sepharose CL-6B column. Fractions of 5 mL can be collected, can be dialyzed, can be lyophilized, and can be analyzed for protein and carbohydrate contents. In a third chromatographic approach, an amount of 4.0 mg of the lyophilized reaction mixture can be dissolved in 1.0 mL of distilled water and applied to a column packed with Sephadex LH-20 previously equilibrated with distilled water, at a flow rate of 0.5 mL/min. Elution can be performed isocratically with distilled water, and the process can be monitored as described above. Fractions can be collected, can be lyophilized, and can be used for further analysis.

Furthermore, 'click' chemistry can be used to conjugate a saccharide with a polypeptide as disclosed in U.S. Pat. No. 8,753,645 and in Hu et al., Towards the next generation of biomedicines by site selective conjugation, *Chem. Soc. Rev.*, 2016, 45, 1691. 'Click' chemistry can be used to conjugate modified $CRM_{197}$ or $CRM_{197}$ with non-natural amino acids to polysaccharides.

Pharmaceutical Compositions and Vaccines

The saccharide-polypeptide conjugates described herein can be in the form of a pharmaceutical composition. The saccharide-polypeptide conjugates described herein can be in the form of a pharmaceutical composition in unit dose form. The saccharide-polypeptide conjugates described herein can be in the form of a vaccine. The saccharide-polypeptide conjugates described herein can be in the form of a vaccine in unit dose form. A pharmaceutical composition or vaccine can comprise an immunogenic saccharide-polypeptide conjugate. A pharmaceutical composition or vaccine can comprise an immunogenic capsular polysaccharide-polypeptide conjugate. A pharmaceutical composition or vaccine can be in unit dose form and can comprise an immunogenic capsular polysaccharide-polypeptide conjugate. A pharmaceutical composition or vaccine can comprise an immunogenic saccharide-polypeptide conjugate wherein the capsular polysaccharide or immunogenic fragment thereof of the saccharide-polypeptide conjugate can be one serotype. In another embodiment, a pharmaceutical composition or vaccine can comprise an immunogenic saccharide-polypeptide conjugates wherein the capsular polysaccharides or immunogenic fragments thereof can be from different serotypes, creating a mixture of different immunogenic saccharide-polypeptide conjugates. A pharmaceutical composition or vaccine can comprise an immunogenic saccharide-polypeptide conjugates wherein the polypeptide is the same polypeptide in all the immunogenic saccharide-polypeptide conjugates. In other embodiments, a pharmaceutical composition or vaccine can comprise immunogenic saccharide-polypeptide conjugates wherein the polypeptide (s) in the saccharide-polypeptide conjugates are a mixture of different polypeptide(s).

For example, a pharmaceutical composition or vaccine can comprise an immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 2, 6C, 8, 9N, 10A, 11A, 12F, 15A, 15B, 15C, 16F, 17F, 22F, 23A, 23B, 24F, 24B, 31, 33F, 34, 35F, 35B, 38 and Serogroup 20 (comprising serotypes 20A and 20B). A pharmaceutical composition or vaccine can comprise an immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising serotypes 20A and 20B). A pharmaceutical composition or vaccine can comprise a plurality of at least two immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B). A pharmaceutical composition or vaccine can comprise a plurality of at least two immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising serotypes 20A and 20B). A pharmaceutical composition or vaccine can comprise a plurality of at least eight immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B). A pharmaceutical composition or vaccine can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7C, 8, 9N, 10A, 11A, 12F, 15A, 16F, 19A, 19F, 22F, 23A, 23B, 31, 33F, 35F, 38, and Serogroup 20 (comprising serotypes 20A and 20B). A pharmaceutical composition or vaccine can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine can comprise a plurality of at least 15 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 7C, 8, 9N, 10A, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine can comprise a plurality of at least 16 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 7C, 8, 9N, 10A, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 8, 9N, 10A, 11A, 12F, 15A, 15B, 16F, 19A, 19F, 22F, 23A, 23B, 31, 33F, 35B, 35F, 38, and Serogroup 20 (comprising serotypes 20A and 20B). A pharmaceutical composition or vaccine can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 8, 9N, 10A, 11A, 12F, 15A, 15B, 15C, 16F, 19A, 22F, 23A, 23B, 24F, 33F, 35B, and 38. A pharmaceutical composition or vaccine can comprise a plurality of at least 10 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 8, 9N, 12F, 15A, 19A, 22F, 23A, 23B, and 24F. A pharmaceutical composition or vaccine can comprise a plurality of at least 11 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 8, 9N, 10A, 12F, 15A, 19A, 22F, 23A, 23B, and 24F. A pharmaceutical composition or vaccine can comprise a plurality of at least 24 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 4, 6C, 7C, 7F, 8, 9N, 10A, 11A, 12F, 15A, 15B, 15C, 16F, 19A, 22F, 23A, 23B, 24F, 31, 33F, 35B, 35F, 38, and Serogroup 20 (comprising serotypes 20A and 20B). A pharmaceutical composition or vaccine can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 8, 9N, 11A, 12F, 15A, 15B, 16F, 19A, 19F, 22F, 23A, 23B, 31, 33F, 35B, 35F, 38, and Serogroup 20 (comprising serotypes 20A and 20B). A pharmaceutical composition or vaccine can comprise a plurality of at least 20, 21, 22, 23, 24, 25, 26, or 27 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7C, 7F, 8, 9N, 10A, 11A, 12F, 15A, 15B, 15C, 16F, 17F, 19A, 19F, 22F, 23A, 23B, 24F, 31, 33F, 34, 35B, 35F, 38 and Serogroup 20 (comprising serotypes 20A and 20B). A pharmaceutical composition or vaccine can comprise a saccharide-polypeptide conjugate comprising a capsular polysaccharide or immunogenic fragment thereof from a serotype of *S. pneumoniae* conjugated to a polypeptide, and wherein the serotype is not any one of, or not at least any one of 1, 3, 4, 5, 6A, 6B, 7F, 9V, 14, 18C, 19A, 19F, and 23F; and the serotype is at least one of 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising serotypes 20A and 20B); or a combination thereof. A pharmaceutical composition or vaccine can comprise a saccharide-polypeptide conjugate comprising a capsular polysaccharide or immunogenic fragment thereof from a serotype of *S. pneumoniae* conjugated to a polypeptide, and wherein the serotype is not any one of, or not at least any one of 1, 3, 4, 5, 6A, 6B, 7F, 9V, 14, 18C, 19A, 19F, and 23F; and the serotype is at least one of 2, 6C, 7C, 7F, 8, 9N, 10A, 11A, 12F, 15A, 15B, 15C, 16F, 17F, 22F, 23A, 23B, 24F, 24B, 31, 33F, 34, 35F, 35B, 38 and Serogroup 20 (comprising serotypes 20A and 20B); or a combination thereof. A pharmaceutical composition or vaccine can comprise a plurality of saccharide-polypeptide conjugates each comprising individually a capsular polysaccharide, fragment thereof, or combination thereof conjugated to a polypeptide, wherein the capsular polysaccharide, fragment thereof, or combination thereof is from a unique *Streptococcus pneumoniae* serotype selected from a group consisting of at least 1, 2, 3, 4, 5, 6, 7, 8, or 9 serotypes selected from the group consisting of 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B). A pharmaceutical composition or vaccine can comprise a plurality of saccharide-polypeptide conjugates each comprising individually a capsular polysaccharide, fragment thereof, or combination thereof conjugated to a polypeptide, wherein the capsular polysaccharide, fragment thereof, or combination thereof is from a unique *Streptococcus pneumoniae* serotype selected from a group consisting of at least 1, 2, 3, 4, 5, 6, 7, 8, or 9 serotypes selected from the group consisting of 2, 6C, 7C, 7F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise at least 10, 11, 12, 13, 14, 15, or 16 serotypes selected from the group consisting of 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising serotypes 20A and 20B). A pharmaceutical composition or vaccine can comprise at least 17, 18, 19, 20, 21, 22, 23, or 24 serotypes selected from the group consisting of 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising serotypes 20A and 20B). A pharmaceutical composition or vaccine can comprise at least 10, 11, 12, 13, 14, 15, or 16 serotypes selected from the group consisting of 2, 6C, 7C, 7F, 8, 9N, 10A, 11A, 12F, 15A, 15B, 15C, 16F, 17F, 22F, 23A, 23B, 24F, 24B, 31, 33F, 34, 35F, 35B, 38 and Serogroup 20 (comprising serotypes 20A and 20B). A pharmaceutical composition or vaccine can comprise at least 17, 18, 19, 20, 21, 22, 23, or 24 serotypes selected from the group consisting of 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B). A pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. A pharmaceutical composition or vaccine can comprise a plurality of saccharide-polypeptide conjugates comprising the serotypes 6C, 8, 9N, 11A, 12F, 15A, 15B, 16F, 22F, 23A, 23B, 24F, 33F, and 35B. A pharmaceutical composition or vaccine can comprise a plurality of saccharide-polypeptide conjugates comprising the serotypes 6C, 8, 9N, 10A, 11A, 12F, 15A, 22F, 23A, 23B, 24F, 33F, and 35B. A pharmaceutical composition or vaccine can comprise a plurality of saccharide-polypeptide conjugates comprising the serotypes 6C, 8, 9N, 10A, 11A, 12F, 15A, 15B, 15C, 16F, 22F, 23A, 23B, 33F, and 35B. A pharmaceutical composition or vaccine can comprise a plurality of saccharide-polypeptide conjugates comprising the serotypes 6C, 8, 9N, 10A, 11A, 12F, 15A, 15B, 15C, 16F, 20B, 22F, 23A, 23B, 33F, and 35B. A pharmaceutical composition or vaccine can comprise a plurality of saccharide-polypeptide conjugates comprising the serotypes 6C, 10A, 11A, 15A, 15B, 15C, 22F, 23A, 24B, 33F, 35B, and 38. A pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. A pharmaceutical composition or vaccine can comprise a plurality of saccharide-polypeptide conjugates comprising the serotypes 6C, 8, 9N, 11A, 12F, 15A, 15B, 16F, 22F, 23A, 23B, 33F, and 35B. A pharmaceutical composition or vaccine can comprise a plurality of saccharide-polypeptide conjugates comprising the serotypes 6C, 8, 9N, 10A, 11A, 12F, 15A, 22F, 23A, 23B, 24F, 33F, and 35B. A pharmaceutical composition or vaccine can comprise a plurality of saccharide-polypeptide conjugates comprising 6C, 10A, 11A, 15A, 15B, 15C, 22F, 23A, 24B, 33F, 35B and 38. A pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. A pharmaceutical composition or vaccine can comprise a plurality of saccharide-polypeptide conjugates comprising the serotypes 6C, 8, 9N, 11A, 12F, 15A, 15B, 16F, 22F, 23A, 23B, 33F, and 35B. A pharmaceutical composition or vaccine can comprise a plurality of saccharide-polypeptide conjugates comprising the serotypes 6C, 8, 9N, 10A, 11A, 12F, 15A, 15B, 23A, 23B, and 35B. A pharmaceutical composition or vaccine can comprise a plurality of saccharide-polypeptide conjugates comprising the serotypes 6C, 8, 9N, 11A, 12F, 15A, 15B, 16F, 23A, 23B, 24F, and 35B. A pharmaceutical composition or vaccine can comprise a plurality of saccharide-polypeptide conjugates comprising the serotypes 6C, 8, 9N, 10A, 11A, 12F, 15A, 23A, 23B, 24F, and 35B. A pharmaceutical composition or vaccine can comprise a plurality of saccharide-polypeptide conjugates comprising the serotypes 6C, 10A, 11A, 15A, 15B, 15C, 23A, 24B, 35B, and 38. A pharmaceutical composition or vaccine can comprise a plurality of saccharide-polypeptide conjugates comprising the serotypes 6C, 8, 9N, 10A, 11A, 12F, 15A, 15B, 23A, 23B, and 35B. A pharmaceutical composition or vaccine can comprise a plurality of saccharide-polypeptide conjugates comprising the serotypes 6C, 8, 9N, 11A, 12F, 15A, 15B, 16F, 23A, 23B, and 35B. A pharmaceutical composition or vaccine can comprise a plurality of saccharide-polypeptide conjugates comprising the serotypes 6C, 8, 9N, 10A, 11A, 12F, 15A, 23A, 23B, 24F, and 35B. A pharmaceutical composition or vaccine can comprise a plurality of saccharide-polypeptide conjugates comprising 6C, 10A, 11A, 15A, 15B, 15C, 23A, 24B, 35B and 38. A pharmaceutical composition or vaccine can comprise a plurality of saccharide-polypeptide conjugates comprising the serotypes 6C, 8, 9N, 10A, 11A, 12F, 15A, 15B, 23A, 23B, and 35B. A pharmaceutical composition or vaccine can comprise a plurality of saccharide-polypeptide conjugates comprising the serotypes 6C, 8, 9N, 11A, 12F, 15A, 15B, 16F, 23A, 23B, and 35B. A pharmaceutical composition or vaccine can comprise a plurality of saccharide-polypeptide conjugates comprising the serotypes 6C, 9N, 15A, 15C, 16F, 23A, 23B, and 35B. A pharmaceutical composition or vaccine can comprise a plurality of saccharide-polypeptide conjugates comprising the serotypes 6C, 15A, 15C, 16F, 23A, 23B, and 35B. A pharmaceutical composition or vaccine can comprise a plurality of saccharide-polypeptide conjugates comprising the serotypes 6C, 9N, 15A, 15C, 16F, 17F, 20B, 23A, 23B, 24F, 31, 33F, 34, 35F, and 35B. A pharmaceutical composition or vaccine can comprise a plurality of saccharide-polypeptide conjugates comprising the serotypes 6C, 8, 9N, 10A, 11A, 12F, 15A, 15B, 15C, 16F, 20A, 22F, 23A, 23B, 33F, and 35B. A pharmaceutical composition or vaccine can comprise a plurality of saccharide-polypeptide conjugates comprising the serotypes 6C, 15A, 15C, 16F, 20B, 23A, 23B, 34F, 31, 33F, 34, 35F, and 35B. A pharmaceutical composition or vaccine can comprise a plurality of saccharide-polypeptide conjugates comprising the serotypes 6C, 8, 9N, 10A, 11A, 15A, 15B, 15C, 16F, 20A, 22F, 23A, 23B, 33F, and 35B. A pharmaceutical composition or vaccine can comprise a plurality of saccharide-polypeptide conjugates comprising at least 13 of the serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B). A pharmaceutical composition or vaccine can comprise a plurality of saccharide-polypeptide conjugates comprising at least 15 of the serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B). A pharmaceutical composition or vaccine can comprise a plurality of saccharide-polypeptide conjugates comprising at least 16 of the serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B 31, 33F, 33B, 35B, 34, 35F, 38 and Serogroup 20 (comprising serotypes 20A and 20B). A pharmaceutical composition or vaccine can comprise a plurality of saccharide-polypeptide conjugates comprising the serotype 6C and at least one additional serotype comprising 1, 2, 3, 4, 5, 6A, 6B, 7C, 7F, 9V, 14, 18C, 19A, 19F, 20B, 23F, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least one additional serotype comprising 2, 7F, 8, 9N, 10A, 11A, 12F, 15A, 15B, 16F, 17F, 22F, 23A, 23B, 24B, 31, 33F, 35B, 35F, 38 and Serogroup 20 (comprising serotypes 20A and 20B). A pharmaceutical composition or vaccine can comprise a plurality of saccharide-polypeptide conjugates comprising the serotype 6C and at least one additional serotype comprising 1, 3, 4, 6A, 6B, 7F, 8, 9N, 10A, 11A, 12F, 14, 15A, 15B, 15C, 16F, 19F, 19A, 22F, 23A, 23B, 24F, 33F, 35F, 35B, 38 or Serogroup 20 (comprising serotypes 20A and 20B). A pharmaceutical composition or vaccine can comprise can comprise a plurality of saccharide-polypeptide conjugates comprising the serotype 6C and at least one additional serotype selected from 1, 3, 4, 6A, 6B, 7F, 8, 9N, 9V, 10A, 11A, 12F, 14, 15A, 15B, 15C, 16F, 19F, 19A, 22F, 23A, 23B, 23F, 24F, 33F, 35F, 35B, 38 or Serogroup 20 (comprising serotypes 20A and 20B). A pharmaceutical composition or vaccine can comprise a plurality of saccharide-polypeptide conjugates comprising at least 13 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising at least 15 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 35B, 34, 35F, 38, and Serogroup 20 (comprising serotypes 20A and 20B). A pharmaceutical composition or vaccine can comprise a plurality of saccharide-polypeptide conjugates comprising at least 16 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B 31, 33F, 34, 35B, 35F, 38, and Serogroup 20 (comprising serotypes 20A and 20B). A pharmaceutical composition or vaccine can comprise can comprise a plurality of saccharide-polypeptide conjugates comprising the serotype 6C and at least one additional serotype comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 20, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least one additional serotype comprising 2, 8, 9N, 10A, 11A, 12F, 15A, 15B, 16F, 17F, 22F, 23A, 23B, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least one additional serotype comprising 1, 3, 4, 6A, 6B, 7F, 8, 9N, 10A, 11A, 12F, 14, 15A, 15B, 15C, 16F, 19F, 19A, 22F, 23A, 23B, 24F, 33F, 34, 35F, 35B, 38, and Serogroup 20 (comprising serotypes 20A and 20B). A pharmaceutical composition or vaccine can comprise can comprise a plurality of saccharide-polypeptide conjugates comprising the serotype 6C and at least one additional serotype selected from 1, 3, 4, 6A, 6B, 7F, 8, 9N, 9V, 10A, 11A, 12F, 14, 15A, 15B, 15C, 16F, 19F, 19A, 22F, 23A, 23B, 23F, 24F, 33F, 34, 35F, 35B, 38, and Serogroup 20 (comprising serotypes 20A and 20B). A pharmaceutical composition or vaccine can comprise a plurality of saccharide-polypeptide conjugates comprising the serotype 6C and at least one additional serotype selected from 3, 4, 7F, 8, 9N, 11A, 12F, 15A, 15B, 15C, 16F, 19A, 22F, 23A, 23B, and 35B. A pharmaceutical composition or vaccine can comprise a plurality of saccharide-polypeptide conjugates comprising the serotype 6C and at least one additional serotype selected from 1, 3, 4, 6A, 7F, 8, 9N, 10A, 11A, 12F, 14, 19A, 19F, 22F, 23A, 23B, 23F, 24F, and 33F. A pharmaceutical composition or vaccine can comprise a plurality of saccharide-polypeptide conjugates comprising the serotype 6C and at least one additional serotype selected from 3, 4, 6B, 10A, 15A, 15B, 19A, 19F, 22F, 23F, 24F, 35B. A pharmaceutical composition or vaccine can comprise a plurality of saccharide-polypeptide conjugates comprising the serotype 6C and at least two additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least three additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least four additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least five additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least six additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least seven additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least eight additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least nine additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least ten additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least eleven additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least twelve additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 35B, 34, 35F, 38 and Serogroup 20 (comprising serotypes 20A and 20B). A pharmaceutical composition or vaccine can comprise a plurality of saccharide-polypeptide conjugates comprising the serotype 6C and at least thirteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 35B, 34, 35F, 38 and Serogroup 20 (comprising serotypes 20A and 20B). A pharmaceutical composition or vaccine can comprise a plurality of saccharide-polypeptide conjugates comprising the serotype 6C and at least fourteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least fifteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least sixteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least seventeen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least eighteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least nineteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least twenty additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least twenty-one additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least twenty-two additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 35B, 34, 35F, 38 and Serogroup 20 (comprising serotypes 20A and 20B). A pharmaceutical composition or vaccine can comprise a plurality of saccharide-polypeptide conjugates comprising the serotype 6C and at least twenty-three additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least twenty-four additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 35B, 34, 35F, 38 and Serogroup 20 (comprising serotypes 20A and 20B). A pharmaceutical composition or vaccine can comprise a plurality of saccharide-polypeptide conjugates comprising the serotype 6C and at least twenty-five additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38 and Serogroup 20 (comprising serotypes 20A and 20B). A pharmaceutical composition or vaccine can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 additional serotypes comprising 1, 2, 3, 4, 5, 6A, 6B, 7F, 7C, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35F, 35B, 38 and Serogroup 20 (comprising serotypes 20A and 20B), or a combination thereof. A pharmaceutical composition or vaccine can comprise a plurality of saccharide-polypeptide conjugates comprising the serotype 6C and at least two additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least three additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least four additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least five additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least six additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least seven additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least eight additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least nine additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least ten additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least eleven additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twelve additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least thirteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least fourteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least fifteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least sixteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least seventeen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least eighteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least nineteen additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twenty additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twenty-one additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twenty-two additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twenty-three additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twenty-four additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least twenty-five additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35B, 35F, 38, and Serogroup 20 (comprising serotypes 20A and 20B). A pharmaceutical composition or vaccine can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 additional serotypes comprising 1, 2, 3, 4, 5, 6A, 6B, 7F, 7C, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 34, 35F, 35B, 38, and Serogroup 20 (comprising serotypes 20A and 20B), or a combination thereof.

A vaccine can comprise immunogenic saccharide-polypeptide conjugates that can each comprise a capsular polysaccharide, fragment thereof, or combination thereof conjugated to a polypeptide, wherein the capsular polysaccharide, fragment thereof, or combination thereof can be from a *Streptococcus pneumoniae* serotype selected from a group consisting of 23A and 23B. A vaccine can comprise at least 2 immunogenic saccharide-polypeptide conjugates that can each comprise a capsular polysaccharide, fragment thereof, or combination thereof conjugated to a polypeptide, wherein the capsular polysaccharide, fragment thereof, or combination thereof can be from a *Streptococcus pneumoniae* serotype group, wherein one serotype can be 23A and at least one additional serotype can be selected from the group consisting of 1, 2, 3, 4, 5, 6A, 6B, 6C, 7C, 7F, 9V, 14, 18C, 19A, 19F, 23F, 8, 9N, 10A, 11A, 12F, 15A, 15B, 15C, 16F, 17F, 20A, 20B, 22F, 23B, 24F, 24B, 31, 33F, 33B, 34, 35B, 35F, and 38. A vaccine can comprising at least 2 immunogenic saccharide-polypeptide conjugates that can each comprise a capsular polysaccharide, fragment thereof, or combination thereof conjugated to a polypeptide, wherein the capsular polysaccharide, fragment thereof, or combination thereof can be from a *Streptococcus pneumoniae* serotype group, wherein one serotype can be 23B and at least one additional serotype can be selected from the group consisting of 1, 2, 3, 4, 5, 6A, 6B, 6C, 7C, 7F, 9V, 14, 18C, 19A, 19F, 23F, 8, 9N, 10A, 11A, 12F, 15A, 15B, 15C, 16F, 17F, 20A, 20B, 22F, 23A, 24F, 24B, 31, 33F, 33B, 34, 35B, 35F, and 38.

The immunogenic saccharide-polypeptide conjugate(s) can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition or vaccine. The immunogenic saccharide-polypeptide conjugate(s) can include excipients that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition or vaccine. The immunogenic saccharide-polypeptide conjugate(s) can include adjuvants that can be individually, respectively, or collectively present in an amount of about: 0.001, 0.01, 0.1, 1, 2, 3, 4, 5, 6, 7, 8, 9, 10, 20, 30, 40, 50, 60, 70, 80, 90, 95, or 100%, by weight, based on the weight of the pharmaceutical composition or vaccine. The pharmaceutical composition or vaccine can be administered to one of a plurality of humans, which elicits at least one of the following side effects in less than about 5%, 10%, 20% or 30% of the plurality of humans: fatigue, headache, muscle pain, joint pain, decreased appetite, chills, or rash.

In other embodiments, a pharmaceutical composition or vaccine can comprise a saccharide-polypeptide conjugate wherein the saccharide is from *N. meningitidis*. A pharmaceutical composition can comprise a saccharide-polypeptide conjugate wherein the saccharide can be from *S. enterica*. A pharmaceutical composition or vaccine can comprise a saccharide-polypeptide conjugate wherein the saccharide can be from *H. influenzae*. A pharmaceutical composition can comprise a plurality of saccharide-polypeptide conjugates comprising saccharides from *Neisseria meningitidis*. A pharmaceutical composition or vaccine can comprise a plurality of saccharide-polypeptide conjugates comprising saccharides from *S. enterica*. A pharmaceutical composition or vaccine can comprise can comprise a plurality of saccharide-polypeptide conjugates comprising saccharides from *H. influenzae*.

The polypeptide of any of the plurality of saccharide-polypeptide conjugates can be the same polypeptide. For example, the polypeptide of any of the plurality of saccharide-polypeptide conjugates can be $CRM_{197}$. The plurality of saccharide-polypeptide conjugates can comprise a mixture of different polypeptides. For example, the plurality of saccharide-polypeptide conjugates can comprise a mixture of $CRM_{197}$, tetanus toxoid, a diphtheria toxoid, or any fragment thereof.

Any pharmaceutical composition or vaccine described herein can be in unit dose form. Additionally, the pharmaceutical composition or vaccine can further comprise an adjuvant. In some embodiments, the adjuvant can be an aluminum-cation comprises adjuvant. In other embodiments, the adjuvant can be aluminum phosphate, aluminum sulfate, or aluminum hydroxide. More examples of suitable adjuvants for use in the pharmaceutical composition or vaccine include: aluminum-based salts and variants thereof; emulsions (either water-in-oil or oil-in-water) and variants thereof, e.g., Freund's Incomplete Adjuvant, MF59® (Glaxosmithkline plc); PRR ligands and variants thereof, e.g., pathogen associated molecular patterns (PAMPs); TLR3 and RLR ligands or variants thereof, e.g., Synthetic analogs of dsRNA, poly(I:C), etc.; TLR4 ligands or variants thereof, e.g., bacterial flagellin, Glucopyranosyl Lipid Adjuvant (GLA), monophosphoryl lipid A, etc.; TLR5 ligands or variants thereof, e.g., imiquimod, gardiquimod, R848, etc.; TLR9 ligands or variants thereof, e.g., Oxydeoxynucleotides containing CpG motifs (CpG ODNs such as ODN1826 and ODN2006); NOD2 ligands or variants thereof, e.g., fragments of bacterial cell walls (such as muramyl dipeptide [MDP]); saponins including synthetic derivatives or variants thereof, e.g., QS21, TQL1055, etc.; or any combination of above. An adjuvant can be 3M-052.

A pharmaceutical composition or vaccine can further comprise an excipient. An excipient can be Acacia, Acesulfame Potassium, Acetic Acid, Glacial Acetone, Acetyltributyl Citrate, Acetyltriethyl Citrate, Agar, Albumin, Alcohol, Alginic Acid, Aliphatic Polyesters, Alitame, Almond Oil, Alpha Tocopherol, Aluminum Hydroxide Adjuvant, Aluminum Oxide, Aluminum Phosphate Adjuvant, Aluminum Stearate, Ammonia Solution, Ammonium Alginate, Ascorbic Acid, Ascorbyl Palmitate, Aspartame, Attapulgite, Bentonite, Benzalkonium Chloride, Benzethonium Chloride, Benzoic Acid, Benzyl Alcohol, Benzyl Benzoate, Boric Acid, Bronopol, Butylated Hydroxyanisole, Butylated Hydroxytoluene, Butylparaben, Calcium Alginate, Calcium Carbonate, Dibasic Anhydrous Calcium Phosphate, Dibasic Dihydrate Calcium Phosphate, Tribasic Calcium Phosphate, Calcium Stearate, Calcium Sulfate, Canola Oil, Carbomer, Carbon Dioxide, Carboxymethylcellulose Calcium, Carboxymethylcellulose Sodium, Carrageenan, Castor Oil, Hydrogenated Castor Oil, Microcrystalline Cellulose, Powdered Cellulose, Silicified Microcrystalline Cellulose, Cellulose Acetate, Cellulose Acetate Phthalate, Ceratonia, Cetostearyl Alcohol, Cetrimide, Cetyl Alcohol, Cetylpyridinium Chloride, Chitosan, Chlorhexidine, Chlorobutanol, Chlorocresol, Chlorodifluoroethane (HCFC), Chlorofluorocarbons (CFC), Chloroxylenol, Cholesterol, Citric Acid Monohydrate, Colloidal Silicon Dioxide, Coloring Agents, Copovidone, Corn Oil, Cottonseed Oil, Cresol, Croscarmellose Sodium, Crospovidone, Cyclodextrins, Cyclomethicone, Denatonium Benzoate, Dextrates, Dextrin, Dextrose, Dibutyl Phthalate, Dibutyl Sebacate, Diethanolamine, Diethyl Phthalate, Difluoroethane (HFC), Dimethicone, Dimethyl Ether, Dimethyl Phthalate, Dimethyl Sulfoxide, Dimethylacetamide, Disodium Edetate, Docusate Sodium, Edetic Acid, Erythorbic Acid, Erythritol, Ethyl Acetate, Ethyl Lactate, Ethyl Maltol, Ethyl Oleate, Ethyl Vanillin, Ethylcellulose, Ethylene Glycol Palmitostearate, Ethylene Vinyl Acetate, Ethylparaben, Fructose, Fumaric Acid, Gelatin, Glucose, Liquid, Glycerin, Glyceryl Behenate, Glyceryl Monooleate, Glyceryl Monostearate, Glyceryl Palmitostearate, Glycofurol, Guar Gum, Hectorite, Heptafluoropropane (HFC), Hexetidine, Hydrocarbons (HC), Hydrochloric Acid, Hydroxyethyl Cellulose, Hydroxyethylmethyl Cellulose, Hydroxypropyl Cellulose, Low-substituted Hydroxypropyl Cellulose, Hydroxypropyl Starch, Hypromellose, Hypromellose Acetate Succinate, Hypromellose Phthalate, Imidurea, Inulin, Iron Oxides, Isomalt, Isopropyl Alcohol, Isopropyl Myristate, Isopropyl Palmitate, Kaolin, Lactic Acid, Lactitol, Anhydrous Lactose, Monohydrate Lactose, Spray-Dried Lactose, Lanolin, Lanolin Alcohols, Hydrous Lanolin, Lauric Acid, Lecithin, Leucine, Linoleic Acid, Macrogol, Hydroxystearate Magnesium Aluminum Silicate, Magnesium Carbonate, Magnesium Oxide, Magnesium Silicate, Magnesium Stearate, Magnesium Trisilicate, Malic Acid, Maltitol, Maltitol Solution, Maltodextrin, Maltol, Maltose, Mannitol, Medium-chain Triglycerides, Meglumine, Menthol, Methylcellulose, Methylparaben, Mineral Oil, Light Mineral Oil, Mineral Oil and Lanolin Alcohols, Monoethanolamine, Monosodium Glutamate, Monothioglycerol, Myristic Acid, Neohesperidin Dihydrochalcone, Nitrogen, Nitrous Oxide, Octyldodecanol, Oleic Acid, Oleyl Alcohol, Olive Oil, Palmitic Acid, Paraffin, Peanut Oil, Pectin, Petrolatum, Petrolatum and Lanolin Alcohols, Phenol, Phenoxyethanol, Phenylethyl Alcohol, Phenylmercuric Acetate, Phenylmercuric Borate, Phenylmercuric Nitrate, Phosphoric Acid, Polacrilin Potassium, Poloxamer, Polycarbophil, Polydextrose, Polyethylene Glycol, Polyethylene Oxide, Polymethacrylates, Poly(methyl vinyl ether/maleic anhydride), Polyoxyethylene Alkyl Ethers, Polyoxyethylene Castor Oil Derivatives, Polyoxyethylene Sorbitan Fatty Acid Esters, Polyoxyethylene Stearates, Polyvinyl Acetate Phthalate, Polyvinyl Alcohol, Potassium Alginate, Potassium Benzoate, Potassium Bicarbonate, Potassium Chloride, Potassium Citrate, Potassium Hydroxide, Potassium Metabisulfite, Potassium Sorbate, Povidone, Propionic Acid, Propyl Gallate, Propylene Carbonate, Propylene Glycol, Propylene Glycol Alginate, Propylparaben, 2-Pyrrolidone, Raffinose, Saccharin, Saccharin Sodium, Saponite, Sesame Oil, Shellac, Simethicone, Sodium Acetate, Sodium Alginate, Sodium Ascorbate, Sodium Benzoate, Sodium Bicarbonate, Sodium Borate, Sodium Chloride, Sodium Citrate Dihydrate, Sodium Cyclamate, Sodium Hyaluronate, Sodium Hydroxide, Sodium Lactate, Sodium Lauryl Sulfate, Sodium Metabisulfite, Dibasic Sodium Phosphate, Monobasic Sodium Phosphate, Sodium Propionate, Sodium Starch Glycolate, Sodium Stearyl Fumarate, Sodium Sulfite, Sorbic Acid, Sorbitan Esters (Sorbitan Fatty Acid Esters), Sorbitol, Soybean Oil, Starch, Pregelatinized Starch, Sterilizable Maize Starch, Stearic Acid, Stearyl Alcohol, Sucralose, Sucrose, Compressible Sugar, Confectioner's Sugar, Sugar Spheres, Sulfobutylether b-Cyclodextrin, Sulfuric Acid, Sunflower Oil, Hard Fat Suppository Bases, Talc, Tartaric Acid, Tetrafluoroethane (HFC), Thaumatin, Thimerosal, Thymol, Titanium Dioxide, Tragacanth, Trehalose, Triacetin, Tributyl Citrate, Triethanolamine, Triethyl Citrate, Vanillin, Hydrogenated Vegetable Oil, Water, Anionic Emulsifying Wax, Carnauba Wax, Cetyl Esters Wax, Microcrystalline Wax, Nonionic Emulsifying Wax, White Wax, Yellow Wax, Xanthan Gum, Xylitol, Zein, Zinc Acetate, or Zinc Stearate.

A pharmaceutical composition or vaccine can further comprise a surfactant or emulsifier, or a combination thereof. A surfactant can be polysorbate, polymer glycol, a sorbitan ester, or any combination thereof. In some embodiments, polysorbate can be polysorbate 80. In some embodiments, polymer glycol can be polyethylene glycol. A surfactant can be TWEEN. A pharmaceutical composition or vaccine can comprise a specific polyethylene glycol based upon its molecular weight. A pharmaceutical composition or vaccine can comprise a preservative. A pharmaceutical composition or vaccine can comprise a salt. The salt can be an inorganic salt. A pharmaceutical composition or vaccine can further comprise an anti-fungal compound or a salt thereof. An antifungal compound can be thimerosal, phenol, benzethonium chloride, or 2-phenoxyethanol. A pharmaceutical composition or vaccine can further comprise a chelating agent. A chelating agent can be ethylenediaminetetraacetic acid (EDTA). A pharmaceutical composition or vaccine can further comprise a buffering agent. The buffering agent can be succinate buffer agent, tris-acetate-ethylenediaminetetraacetic acid (TAE) buffering agent, 4-(2-hydroxyethyl)-1-piperazineethanesulfonic acid (HEPES) buffering agent, phosphate buffering agent, sodium phosphate buffering agent, or a potassium phosphate buffering agent. A pharmaceutical composition or vaccine can further comprise sterile water. When the pharmaceutical composition or vaccine can be administered intramuscularly to a human, the pharmaceutical composition or vaccine can elicit an immune response that lasts from about 1 week to about 30 years. A pharmaceutical composition or vaccine retains at least about 60% of its original biological activity when stored in a sealed container for about 24 months at a temperature of about 2° C.-8° C. when the sealed container is stored in an atmosphere having about 50% relative humidity and 1 atm of atmospheric pressure. A pharmaceutical composition or vaccine can retain at least about 70% of its original biological activity when stored in a sealed container for about 24 months at a temperature of about 2° C.-8° C. when the sealed container is stored in an atmosphere having about 50% relative humidity and 1 atm of atmospheric pressure. A pharmaceutical composition or vaccine can retain at least about 80% of its original biological activity when stored in a sealed container for about 24 months at a temperature of about 2° C.-8° C. when the sealed container is stored in an atmosphere having about 50% relative humidity and 1 atm of atmospheric pressure. A pharmaceutical composition or vaccine can retain at least about 90% of its original biological activity when stored in a sealed container for about 24 months at a temperature of about 2° C.-8° C. when the sealed container is stored in an atmosphere having about 50% relative humidity and 1 atm of atmospheric pressure.

The polysaccharide-polypeptide conjugates as described herein can be adjuvanted. Suitable adjuvants can include an aluminum hydroxide gel (alum) or aluminum phosphate, but can also be a salt of calcium, magnesium, iron or zinc, or can be an insoluble suspension of acylated tyrosine, or acylated sugars, cationically or anionically derivatized polysaccharides, or polyphophazenes. An adjuvant can be 3M-052. When adjuvanted with aluminum salts, the ratio of aluminum salt to polysaccharide can be less than 10:1 (w/w), less than 8:1 (w/w), or more than 2:1 (w/w) in a pharmaceutical composition dose or formulation, or a vaccine dose or formulation.

The amount of polypeptide in a pharmaceutical composition dose or vaccine dose can be selected as an amount which can induces an immunoprotective response without significant adverse effects. A dose or formulation can comprise from 0.1-100 µg of polysaccharide and/or for a polysaccharide polypeptide conjugate from 0.1-50 µg of polysaccharide. A polysaccharide-polypeptide conjugate can comprise from 1-10 µg of polysaccharide, 1-5 µg of polysaccharide, or 2-5 µg of polysaccharide. A polysaccharide-polypeptide conjugate can comprise about 0.5 µg of polysaccharide, about 1 µg of polysaccharide, about 1.5 µg of polysaccharide, about 2 µg of polysaccharide, about 2.5 µg of polysaccharide, about 3 µg of polysaccharide, about 3.5 µg of polysaccharide, about 4 µg of polysaccharide, about 5 µg of polysaccharide, about 6 µg of polysaccharide, about 7 µg of polysaccharide, about 8 µg of polysaccharide about 9 µg of polysaccharide about 10 µg of polysaccharide, about 11 µg of polysaccharide, about 12 µg of polysaccharide, about 13 µg of polysaccharide, about 14 µg of polysaccharide, about 15 µg of polysaccharide, about 16 µg of polysaccharide, about 17 µg of polysaccharide, about 18 µg of polysaccharide, about 19 µg of polysaccharide, or about 20 µg of polysaccharide. The content of polypeptide in the vaccine can be in the range from 1-100 µg of polypeptide, 5-50 µg of polypeptide, or 5-25 µg of polypeptide.

The total amount of capsular polysaccharide, fragment thereof, or combination thereof, individually for each *Streptococcus pneumoniae* serotype in a pharmaceutical composition dose or a vaccine dose in unit dose form, can range from about 0.5 µg to about 5 µg. The total amount of capsular polysaccharide, fragment thereof, or combination thereof, individually for each *Streptococcus pneumoniae* serotype in a pharmaceutical composition dose or a vaccine dose in unit dose form, can range from 0.5 µg to 5 µg. The total amount of capsular polysaccharide, fragment thereof, or combination thereof, individually for each *Streptococcus pneumoniae* serotype in a pharmaceutical composition dose or in a vaccine dose in unit dose form, can range from about 1 µg to about 4 µg. The total amount of capsular polysaccharide, fragment thereof, or combination thereof, individually for each *Streptococcus pneumoniae* serotype in a pharmaceutical composition dose or a vaccine dose in unit dose form, can range from about 1 µg to about 4 µg. The total amount of capsular polysaccharide, fragment thereof, or combination thereof, individually for each *Streptococcus pneumoniae* serotype in a pharmaceutical composition dose or in a vaccine dose in unit dose form, can range from about 1 µg to about 8 µg. The total amount of capsular polysaccharide, fragment thereof, or combination thereof, individually for each *Streptococcus pneumoniae* serotype in a pharmaceutical composition dose or a vaccine dose in unit dose form, can range from about 1 µg to about 8 µg. The total amount of capsular polysaccharide, fragment thereof, or combination thereof, individually for each *Streptococcus pneumoniae* serotype in a pharmaceutical composition dose or in a vaccine dose in unit dose form, can range from about 1 µg to about 10 µg. The total amount of capsular polysaccharide, fragment thereof, or combination thereof, individually for each *Streptococcus pneumoniae* serotype in a pharmaceutical composition dose or a vaccine dose in unit dose form, can range from about 1 µg to about 10 µg. The total amount of capsular polysaccharide, fragment thereof, or combination thereof, individually for each *Streptococcus pneumoniae* serotype in a pharmaceutical composition dose or in a vaccine dose in unit dose form, can range from about 1 µg to about 15 µg. The total amount of capsular polysaccharide, fragment thereof, or combination thereof, individually for each *Streptococcus pneumoniae* serotype in a pharmaceutical composition dose or a vaccine dose in unit dose form, can range from about 1 µg to about 15 µg. The total amount of capsular polysaccharide, fragment thereof, or combination thereof, individually for each *Streptococcus pneumoniae* serotype in a pharmaceutical composition dose or in a vaccine dose in unit dose form, can range from about 1 µg to about 20 µg. The total amount of capsular polysaccharide, fragment thereof, or combination thereof, individually for each *Streptococcus pneumoniae* serotype in a pharmaceutical composition dose or a vaccine dose in unit dose form, can range from about 1 µg to about 20 µg. The total amount of capsular polysaccharide, fragment thereof, or combination thereof, individually for each *Streptococcus pneumoniae* serotype in a pharmaceutical composition dose or in a vaccine dose in unit dose form, can range from about 4 µg to about 8 µg. The total amount of capsular polysaccharide, fragment thereof, or combination thereof, individually for each *Streptococcus pneumoniae* serotype in a pharmaceutical composition dose or a vaccine dose in unit dose form, can range from about 4 µg to about 8 µg. The total amount of capsular polysaccharide, fragment thereof, or combination thereof, individually for each *Streptococcus pneumoniae* serotype in a pharmaceutical composition dose or in a vaccine dose in unit dose form, can range from about 2 µg to about 6 µg. The total amount of capsular polysaccharide, fragment thereof, or combination thereof, individually for each *Streptococcus pneumoniae* serotype in a pharmaceutical composition dose or a vaccine dose in unit dose form, can range from about 2 µg to about 6 µg. The total amount of capsular polysaccharide, fragment thereof, or combination thereof, individually for each *Streptococcus pneumoniae* serotype in a pharmaceutical composition dose or in a vaccine dose in unit dose form, can range from about 3 µg to about 5 µg. The total amount of capsular polysaccharide, fragment thereof, or combination thereof, individually for each *Streptococcus pneumoniae* serotype in a pharmaceutical composition dose or a vaccine dose in unit dose form, can range from about 3 µg to about 5 µg. The total amount of capsular polysaccharide, fragment thereof, or combination thereof, individually for each *Streptococcus pneumoniae* serotype in a pharmaceutical composition dose or a vaccine dose in unit dose form, can be about 0.5 µg, about 1 µg, about 2 µg, about 3 µg, about 4 µg, or about 5 µg. The total amount of capsular polysaccharide, fragment thereof, or combination thereof, individually for each *Streptococcus pneumoniae* serotype in a pharmaceutical composition dose or a vaccine dose in unit dose form, can be 0.5 µg, 1 µg, 2 µg, 3 µg, 4 µg, or 5 µg. In some embodiments, a total amount of unconjugated capsular polysaccharide, fragment thereof, or combination thereof, individually for each *Streptococcus pneumoniae* serotype in a pharmaceutical composition dose or vaccine dose in unit dose form, can range from about 0% to about 30% w/w. In some embodiments, a total amount of unconjugated capsular polysaccharide, fragment thereof, or combination thereof, individually for each *Streptococcus pneumoniae* serotype in a pharmaceutical composition dose or vaccine dose in unit dose form, can range from 0% to 30% w/w. In some embodiments, a total amount of unconjugated capsular polysaccharide, fragment thereof, or combination thereof, individually for each *Streptococcus pneumoniae* serotype in a pharmaceutical composition dose or vaccine dose in unit dose form, can range from about 0% to about 20% w/w. In some embodiments, a total amount of unconjugated capsular polysaccharide, fragment thereof, or combination thereof, individually for each *Streptococcus pneumoniae* serotype in a pharmaceutical composition dose or vaccine dose in unit dose form, can range from 0% to 20% w/w. In some embodiments, a total amount of unconjugated capsular polysaccharide, fragment thereof, or combination thereof, individually for each *Streptococcus pneumoniae* serotype in a pharmaceutical composition dose or vaccine dose in unit dose form, can range from about 0% to about 10% w/w. In some embodiments, a total amount of unconjugated capsular polysaccharide, fragment thereof, or combination thereof, individually for each *Streptococcus pneumoniae* serotype in a pharmaceutical composition dose or vaccine dose in unit dose form, can range from 0% to 10% w/w.

TABLE 2

Exemplary Total Amount of Polysaccharide in a Pharmaceutical Composition or Vaccine in Unit Dose Form

| Polysaccharide Serotype* | Total Amount of Polysaccharide in Polysaccharide-Polypeptide Conjugate** | | |
|---|---|---|---|
| 1 | about 1 µg | about 2 µg | about 4 µg |
| 2 | about 1 µg | about 2 µg | about 4 µg |
| 3 | about 1 µg | about 2 µg | about 4 µg |
| 4 | about 1 µg | about 2 µg | about 4 µg |
| 5 | about 1 µg | about 2 µg | about 4 µg |
| 6A | about 1 µg | about 2 µg | about 4 µg |
| 6B | about 1 µg | about 2 µg | about 4 µg |
| 6C | about 1 µg | about 2 µg | about 4 µg |
| 7F | about 1 µg | about 2 µg | about 4 µg |
| 7C | about 1 µg | about 2 µg | about 4 µg |
| 8 | about 1 µg | about 2 µg | about 4 µg |
| 9N | about 1 µg | about 2 µg | about 4 µg |
| 9V | about 1 µg | about 2 µg | about 4 µg |
| 10A | about 1 µg | about 2 µg | about 4 µg |
| 11A | about 1 µg | about 2 µg | about 4 µg |
| 12F | about 1 µg | about 2 µg | about 4 µg |
| 14 | about 1 µg | about 2 µg | about 4 µg |
| 15A | about 1 µg | about 2 µg | about 4 µg |
| 15B | about 1 µg | about 2 µg | about 4 µg |
| 15C | about 1 µg | about 2 µg | about 4 µg |
| 16F | about 1 µg | about 2 µg | about 4 µg |
| 17F | about 1 µg | about 2 µg | about 4 µg |
| 18C | about 1 µg | about 2 µg | about 4 µg |
| 19F | about 1 µg | about 2 µg | about 4 µg |
| 19A | about 1 µg | about 2 µg | about 4 µg |
| 20A | about 1 µg | about 2 µg | about 4 µg |
| 20B | about 1 µg | about 2 µg | about 4 µg |
| 20 (comprising 20A and 20B) | about 1 µg | about 2 µg | about 4 µg |
| 22F | about 1 µg | about 2 µg | about 4 µg |
| 23F | about 1 µg | about 2 µg | about 4 µg |
| 23A | about 1 µg | about 2 µg | about 4 µg |
| 23B | about 1 µg | about 2 µg | about 4 µg |
| 24F | about 1 µg | about 2 µg | about 4 µg |
| 24B | about 1 µg | about 2 µg | about 4 µg |
| 31 | about 1 µg | about 2 µg | about 4 µg |
| 33F | about 1 µg | about 2 µg | about 4 µg |
| 33B | about 1 µg | about 2 µg | about 4 µg |
| 34 | about 1 µg | about 2 µg | about 4 µg |
| 35F | about 1 µg | about 2 µg | about 4 µg |
| 35B | about 1 µg | about 2 µg | about 4 µg |
| 38 | about 1 µg | about 2 µg | about 4 µg |

*Each serotype polysaccharide can be in a pharmaceutical composition or a vaccine in any one of the total amounts listed in the table
**Total amount can refer to the amount of polysaccharide of a serotype in a pharmaceutical composition or a vaccine when the pharmaceutical composition or vaccine is in unit dose form A vaccine or pharmaceutical composition can be in unit dose form. A vaccine or pharmaceutical composition can comprise an immunogenic saccharide-$CRM_{197}$ conjugate comprising an immunogenic saccharide, fragment, combination thereof of serotype 1, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 1, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 2, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 2, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 3, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 3, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A pharmaceutical composition can comprise an immunogenic saccharide-$CRM_{197}$ conjugate comprising an immunogenic saccharide, fragment, combination thereof of serotype 4, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 4, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 5, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 5, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 6A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 6A, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 6B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 6B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 7F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 7F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 7C, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 7C, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 9V, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 9V, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 14, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 14, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 18C, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 18C, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 19A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 19A the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 19F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 19F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 23F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 23F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 6C, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 6C, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 8, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 8, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 9N, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 9N, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 10A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 10A, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 11A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 11A, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 12F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 12F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 15A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 15A, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 15B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 15B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 15C, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 15C, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 16F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 16F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 17F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 17F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 20A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 20A, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 20B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 20B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 22F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 22F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 23A, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 23A, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 23B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 23B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 24F the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 24F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 24B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 24B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 31, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 31, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 33F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 33F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 33B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 33B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 35F, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 35F, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 34, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 34, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 35B, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 35B, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0. A vaccine or pharmaceutical composition can comprise an immunogenic saccharide-$CRM_{197}$ conjugate comprising an immunogenic saccharide, fragment, combination thereof of serotype 38, the immunogenic saccharide-$CRM_{197}$ conjugate can have a molecular weight from about 300 kDa to about 10,000 kDa, and a ratio (w/w) of the capsular polysaccharide, fragment thereof, or combination thereof to the $CRM_{197}$ can be from about 0.3 to about 3.0. A vaccine or pharmaceutical composition can comprise an immunogenic saccharide-$CRM_{197}$ conjugate comprising an immunogenic saccharide, fragment, combination thereof of serotype 38, the immunogenic saccharide-$CRM_{197}$ conjugate can have a molecular weight from 300 kDa to 10,000 kDa, and a ratio (w/w) of the capsular polysaccharide, fragment thereof, or combination thereof to the $CRM_{197}$ can be from 0.3 to 3.0.

The vaccine or pharmaceutical composition can comprise in any combination of serotypes as described above (e.g., see EXAMPLE 6).

The vaccine dosage can be in the range from 1-5 μg of polysaccharide per polysaccharide polypeptide conjugate delivered intramuscularly as a single 0.5 mL injection. The vaccine dosage can comprise aluminum phosphate (1 mg/mL) and 0.01% polysorbate 80.

Methods of Use

The saccharide-polypeptide conjugates as described herein can be formulated for use in a vaccine. The pharmaceutical compositions comprising a saccharide-polypeptide conjugate as described herein can be formulated for use in a vaccine. The pharmaceutical compositions comprising a saccharide-polypeptide conjugate as described herein can be used in a vaccine. The vaccine can be administered to a subject. The vaccine can be used as a prophylactic for disease caused by *S. pneumoniae*, such as meningitis, pneumonia, and severe invasive diseases associated with pneumococcal infection. The subject can be a human. The subject or human can be a subject or human in need thereof.

The saccharide-polypeptide conjugate can be administered by intramuscular injection. The saccharide-polypeptide conjugate can be administered via intramuscular, intraperitoneal, intradermal or subcutaneous routes, or via mucosal administration to the oral/alimentary, respiratory or genitourinary tracts. The saccharide-polypeptide conjugate can be administered via a suppository. The saccharide-polypeptide conjugate can be administered intranasally. The saccharide-polypeptide conjugate can elicit an opsonophagocytic response after administration. The saccharide-polypeptide conjugate can elicit the production of antibodies against the serotype of the saccharide-polypeptide conjugate. This antibody response can be measured by an in vitro opsonophagocytic assay after administration of the saccharide-polypeptide conjugate.

The pharmaceutical composition or vaccine comprising a saccharide-polypeptide conjugate can be administered by intramuscular injection. The pharmaceutical composition or vaccine comprising a saccharide-polypeptide conjugate can be administered via intramuscular, intraperitoneal, intradermal or subcutaneous routes, or via mucosal administration to the oral/alimentary, respiratory or genitourinary tracts. The pharmaceutical composition or vaccine comprising a saccharide-polypeptide conjugate can be administered intranasally. The pharmaceutical composition or vaccine can be administered intramuscularly and can elicit an immune response that lasts from 1 week to 30 years. The saccharide-polypeptide conjugate can elicit an opsonophagocytic response after administration. The pharmaceutical composition or vaccine comprising a saccharide-polypeptide conjugate can elicit the production of antibodies against the serotype of the saccharide-polypeptide conjugate. This antibody response can be measured by an in vitro opsonophagocytic assay after administration of the pharmaceutical composition or vaccine comprising the saccharide-polypeptide conjugate.

For example, a pharmaceutical composition or vaccine administered to a subject can comprise a saccharide-polypeptide conjugate comprising a capsular polysaccharide or immunogenic fragment thereof from a serotype of *S. pneumoniae* conjugated to a polypeptide, and wherein the serotype is not at least one of, or is not 1, 3, 4, 5, 6A, 6B, 7F, 9V, 14, 18C, 19A, 19F, or 23F; the serotype is at least 1, 2, 3, 4, 5, 6, 7, 8, 9, 10, 11, 12, 13, 14, 15, 16, 17, 18, 19, 21, 22, 23, or 24 of 2, 6C, 7C, 7F, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B); or a combination thereof. A pharmaceutical composition or vaccine administered to a subject can comprise a plurality of saccharide-polypeptide conjugates comprising at least nine serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least ten serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 34, 35B, 35F, 38 and Serogroup 20 (comprising serotypes 20A and 20B). A pharmaceutical composition or vaccine administered to a subject can comprise at least eleven serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least twelve serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least thirteen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least fourteen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least fifteen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least sixteen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least seventeen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least eighteen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least nineteen serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least twenty serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least twenty-one serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). A pharmaceutical composition or vaccine administered to a subject can comprise at least twenty-two serotypes selected from the group consisting of 2, 6C, 7C, 7F, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). For example, a pharmaceutical composition or vaccine administered to a subject can comprise a saccharide-polypeptide conjugate comprising a capsular polysaccharide or immunogenic fragment thereof from a serotype of S. pneumoniae conjugated to a polypeptide, and wherein the serotype is not at least one of, or is not 1, 3, 4, 5, 6A, 6B, 7F, 9V, 14, 18C, 19A, 19F, or 23F; the serotype is at least 1, 2, 3, 4, 5, 6, 7, 8, 9, 10, 11, 12, 13, 14, 15, 16, 17, 18, 19, 20, 21, 22, 23, or of 2, 6C, 7C, 8, 9N, 10A, 11A, 12F, 15A, 15B, 15C, 16F, 17F, 22F, 23A, 23B, 24F, 24B, 31, 33F, 33B, 34, 35B, 35F, 38, and Serogroup 20 (comprising serotypes 20A and 20B); or a combination thereof. A pharmaceutical composition or vaccine administered to a subject can comprise a plurality of saccharide-polypeptide conjugates comprising at least nine serotypes selected from the group consisting of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38, and Serogroup 20 (comprising serotypes 20A and 20B). A pharmaceutical composition or vaccine administered to a subject can comprise at least ten serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least eleven serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least twelve serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least thirteen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least fourteen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least fifteen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition administered to a subject can comprise at least sixteen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least seventeen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least eighteen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least nineteen serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least twenty serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least twenty-one serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise at least twenty-two serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising serotypes 20A and 20B). A pharmaceutical composition or vaccine administered to a subject can comprise a plurality of saccharide-polypeptide conjugates comprising the serotypes 6C, 8, 9N, 10A, 11A, 12F, 15A, 15B, 22F, 23A, 23B, 33F, and 35B. A pharmaceutical composition or vaccine administered to a subject can comprise a plurality of saccharide-polypeptide conjugates comprising the serotypes 6C, 8, 9N, 11A, 12F, 15A, 15B, 16F, 22F, 23A, 23B, 24F, 33F, and 35B. A pharmaceutical composition or vaccine administered to a subject can comprise a plurality of saccharide-polypeptide conjugates comprising the serotypes 6C, 8, 9N, 10A, 11A, 12F, 15A, 22F, 23A, 23B, 24F, 33F, and 35B. A pharmaceutical composition or vaccine administered to a subject can comprise a plurality of saccharide-polypeptide conjugates comprising the serotypes 6C, 8, 9N, 10A, 11A, 12F, 15A, 15B, 15C, 16F, 22F, 23A, 23B, 33F, and 35B. A pharmaceutical composition administered to a subject can comprise a plurality of saccharide-polypeptide conjugates comprising the serotypes 6C, 8, 9N, 10A, 11A, 12F, 15A, 15B, 15C, 16F, 20B, 22F, 23A, 23B, 33F, and 35B. A pharmaceutical composition or vaccine administered to a subject can comprise a plurality of saccharide-polypeptide conjugates comprising the serotypes 6C, 8, 9N, 10A, 11A, 12F, 15A, 15B, 15C, 16F, 22F, 23A, 23B, 33F, 35B and Serogroup 20 (comprising 20A and 20B). A pharmaceutical composition or vaccine administered to a subject can comprise a plurality of saccharide-polypeptide conjugates comprising the serotypes 6C, 10A, 11A, 15A, 15B, 15C, 22F, 23A, 24B, 33F, 35B, and 38. A pharmaceutical composition or vaccine administered to a subject can comprise a plurality of saccharide-polypeptide conjugates comprising the serotypes 6C, 8, 9N, 10A, 11A, 12F, 15A, 15B, 22F, 23A, 23B, 33F, and 35B. A pharmaceutical composition or vaccine administered to a subject can comprise a plurality of saccharide-polypeptide conjugates comprising the serotypes 6C, 8, 9N, 11A, 12F, 15A, 15B, 16F, 22F, 23A, 23B, 33F, and 35B. A pharmaceutical composition or vaccine administered to a subject can comprise a plurality of saccharide-polypeptide conjugates comprising the serotypes 6C, 8, 9N, 10A, 11A, 12F, 15A, 22F, 23A, 23B, 24F, 33F, and 35B. A pharmaceutical composition or vaccine administered to a subject can comprise a plurality of saccharide-polypeptide conjugates comprising 6C, 10A, 11A, 15A, 15B, 15C, 22F, 23A, 24B, 33F, 35B and 38. A pharmaceutical composition or vaccine administered to a subject can comprise a plurality of saccharide-polypeptide conjugates comprising the serotypes 6C, 8, 9N, 10A, 11A, 12F, 15A, 15B, 22F, 23A, 23B, 33F, and 35B. A pharmaceutical composition or vaccine administered to a subject can comprise a plurality of saccharide-polypeptide conjugates comprising the serotypes 6C, 8, 9N, 11A, 12F, 15A, 15B, 16F, 22F, 23A, 23B, 33F, and 35B. A pharmaceutical composition or vaccine administered to a subject can comprise a plurality of saccharide-polypeptide conjugates comprising at least 13 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38 and Serogroup 20 (comprising serotypes 20A and 20B), or a combination thereof. A pharmaceutical composition or vaccine administered to a subject can comprise a plurality of saccharide-polypeptide conjugates comprising at least 14 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38 and Serogroup 20 (comprising serotypes 20A and 20B), or a combination thereof. A pharmaceutical composition or vaccine administered to a subject can comprise a plurality of saccharide-polypeptide conjugates comprising at least 15 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, and 38, and Serogroup 20 (comprising serotypes 20A and 20B), or a combination thereof. A pharmaceutical composition or vaccine administered to a subject can comprise a plurality of saccharide-polypeptide conjugates comprising at least 16 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38 and Serogroup 20 (comprising serotypes 20A and 20B), or a combination thereof. A pharmaceutical composition or vaccine administered to a subject can comprise a plurality of saccharide-polypeptide conjugates comprising at least 17 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38 and Serogroup 20 (comprising serotypes 20A and 20B), or a combination thereof. A pharmaceutical composition or vaccine administered to a subject can comprise a plurality of saccharide-polypeptide conjugates comprising at least 18 of the serotypes 1, 2, 3, 4, 5, 6A, 6B, 7F, 9V, 14, 18C, 19A, 19F, 33B, 23F, 6C, 8, 9N, 10A, 11A, 12F, 15A, 15B, 15C, 16F, 17F, 22F, 23A, 23B, 24F, 31, 33F, 34, 35B, 38 and Serogroup 20 (comprising serotypes 20A and 20B), or a combination thereof. A pharmaceutical composition or vaccine administered to a subject can comprise can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B), or a combination thereof. A pharmaceutical composition or vaccine administered to a subject can comprise can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional serotype comprising 1, 3, 4, 6A, 6B, 7F, 8, 9N, 10A, 11A, 12F, 14, 15A, 15B, 15C, 16F, 19F, 19A, 22F, 23A, 23B, 24F, 24B, 33F, 33B, 34, 35F, 35B, 38 or Serogroup 20 (comprising serotypes 20A and 20B). A pharmaceutical composition or vaccine administered to a subject can comprise can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 additional serotype 1, 3, 4, 6A, 6B, 7F, 8, 9N, 9V, 10A, 11A, 12F, 14, 15A, 15B, 15C, 16F, 19F, 19A, 22F, 23A, 23B, 23F, 24F, 24B, 33F, 33B, 34, 35F, 35B, 38 or Serogroup 20 (comprising serotypes 20A and 20B). A pharmaceutical composition or vaccine administered to a subject can comprise a plurality of saccharide-polypeptide conjugates comprising at least 13 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38, and Serogroup 20 (comprising 20A and 20B), or a combination thereof. A pharmaceutical composition or vaccine administered to a subject can comprise a plurality of saccharide-polypeptide conjugates comprising at least 14 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38, and Serogroup 20 (comprising 20A and 20B), or a combination thereof. A pharmaceutical composition or vaccine administered to a subject can comprise a plurality of saccharide-polypeptide conjugates comprising at least 15 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38, and Serogroup 20 (comprising 20A and 20B), or a combination thereof. A pharmaceutical composition or vaccine administered to a subject can comprise a plurality of saccharide-polypeptide conjugates comprising at least 16 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38, and Serogroup 20 (comprising 20A and 20B), or a combination thereof. A pharmaceutical composition or vaccine administered to a subject can comprise a plurality of saccharide-polypeptide conjugates comprising at least 17 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38, and Serogroup 20 (comprising 20A and 20B) or a combination thereof. A pharmaceutical composition or vaccine administered to a subject can comprise a plurality of saccharide-polypeptide conjugates comprising at least 18 of the serotypes 1, 2, 3, 4, 5, 6A, 6B, 7F, 9V, 14, 18C, 19A, 19F, 23F, 6C, 8, 9N, 10A, 11A, 12F, 15A, 15B, 15C, 16F, 17F, 22F, 23A, 23B, 24F, 31, 33F, 33B, 34, 35B, 38, and Serogroup 20 (comprising 20A and 20B), or a combination thereof. A pharmaceutical composition or vaccine administered to a subject can comprise can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 additional serotypes comprising 1, 2, 3, 4, 5, 6A, 6B, 7F, 9V, 14, 18C, 19A, 19F, 23F, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising 20A and 20B), or a combination thereof. A pharmaceutical composition or vaccine administered to a subject can comprise can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27 or 28 additional serotype comprising 1, 3, 4, 6A, 6B, 7F, 8, 9N, 10A, 11A, 12F, 14, 15A, 15B, 15C, 16F, 19F, 19A, 22F, 23A, 23B, 24F, 24B, 33F, 33B, 34, 35F, 35B, 38, or Serogroup 20 (comprising 20A and 20B). A pharmaceutical composition or vaccine administered to a subject can comprise can comprise a plurality of saccharide-polypeptide conjugates comprising the serotype 6C and at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 additional serotype 1, 3, 4, 6A, 6B, 7F, 8, 9N, 9V, 10A, 11A, 12F, 14, 15A, 15B, 15C, 16F, 19F, 19A, 22F, 23A, 23B, 23F, 24F, 24B, 33F, 33B, 34, 35F, 35B, 38, or Serogroup 20 (comprising 20A and 20B). A pharmaceutical composition or vaccine can comprise administered to a subject can comprise a plurality of saccharide-polypeptide conjugates comprising the serotype 6C and at least one additional serotype selected from 8, 9N, 10A, 11A, 12F, 15A, 15B, 15C, 16F, 22F, 23A, 23B, 33F, and 35B. A pharmaceutical composition or vaccine can comprise administered to a subject can comprise a plurality of saccharide-polypeptide conjugates comprising the serotype 6C and at least 2, 3, 4, 5, 6, 7, 8, 9, 10, 11, 12, 13, 14, or 15 additional serotypes selected from 8, 9N, 10A, 11A, 12F, 15A, 15B, 15C, 16F, 22F, 23A, 23B, 33F, 34, and 35B. A pharmaceutical composition or vaccine can comprise administered to a subject can comprise a plurality of saccharide-polypeptide conjugates comprising the serotype 6C and at least one additional serotype selected from 8, 9N, 10A, 11A, 12F, 15A, 15B, 15C, 16F, 20B, 22F, 23A, 23B, 33F, and 35B. A pharmaceutical composition or vaccine can comprise administered to a subject can comprise a plurality of saccharide-polypeptide conjugates comprising the serotype 6C and at least 2, 3, 4, 5, 6, 7, 8, 9, 10, 11, 12, 13, 14, 15, or 16 additional serotypes selected from 8, 9N, 10A, 11A, 12F, 15A, 15B, 15C, 16F, 20B, 22F, 23A, 23B, 33F, 34, and 35B. A pharmaceutical composition or vaccine can comprise administered to a subject can comprise a plurality of saccharide-polypeptide conjugates comprising the serotype 6C and at least one additional serotype selected from 8, 9N, 10A, 11A, 12F, 15A, 15B, 15C, 16F, 22F, 23A, 23B, 33F, 35B, and Serogroup 20 (comprising 20A and 20B). A pharmaceutical composition or vaccine can comprise administered to a subject can comprise a plurality of saccharide-polypeptide conjugates comprising the serotype 6C and at least 2, 3, 4, 5, 6, 7, 8, 9, 10, 11, 12, 13, 14, 15, or 16 additional serotypes selected from 8, 9N, 10A, 11A, 12F, 15A, 15B, 15C, 16F, 22F, 23A, 23B, 33F, 35B, and Serogroup 20 (comprising 20A and 20B). A pharmaceutical composition or vaccine can comprise administered to a subject can comprise a plurality of saccharide-polypeptide conjugates comprising the serotype 6C and at least one additional serotype selected from 3, 4, 7F, 8, 9N, 11A, 12F, 15A, 15B, 15C, 16F, 19F, 22F, 23A, 23B, and 35B. A pharmaceutical composition or vaccine administered to a subject can comprise can comprise a plurality of saccharide-polypeptide conjugates comprising the serotype 6C and at least one additional serotype selected from 1, 3, 4, 6A, 7F, 8, 9N, 10A, 11A, 12F, 14, 19A, 19F, 22F, 23A, 23B, 23F, 24F, and 33F. A pharmaceutical composition or vaccine administered to a subject can comprise can comprise a plurality of saccharide-polypeptide conjugates comprising the serotype 6C and at least one additional serotype selected from 3, 4, 6B, 10A, 15A, 15B, 19A, 19F, 22F, 23F, 24F, and 35B. A pharmaceutical composition or vaccine administered to a subject can comprise can comprise a plurality of saccharide-polypeptide conjugates comprising the serotype 6C and at least one additional serotype selected from 9N, 15A, 15C, 16F, 23A, 23B, and 33B. A pharmaceutical composition or vaccine administered to a subject can comprise can comprise a plurality of saccharide-polypeptide conjugates comprising the serotype 6C and at least one additional serotype selected from 9N, 15A, 15C, 16F, 23A, 23B, and 33F. A pharmaceutical composition or vaccine administered to a subject can comprise can comprise a plurality of saccharide-polypeptide conjugates comprising the serotype 6C and at least one additional serotype selected from 15A, 15C, 16F, 23A, 23B, and 33B. A pharmaceutical composition or vaccine administered to a subject can comprise can comprise a plurality of saccharide-polypeptide conjugates comprising the serotype 6C and at least one additional serotype selected from 15A, 15C, 16F, 23A, 23B, and 33F. A pharmaceutical composition or vaccine administered to a subject can comprise can comprise a plurality of saccharide-polypeptide conjugates comprising the serotype 6C and at least one additional serotype selected from 9N, 15A, 15C, 16F, 17F, 20B, 23A, 23B, 24F, 31, 33B, 34, 35F, and 35B. A pharmaceutical composition or vaccine administered to a subject can comprise can comprise a plurality of saccharide-polypeptide conjugates comprising the serotype 6C and at least one additional serotype selected from 9N, 15A, 15C, 16F, 17F, 20B, 23A, 23B, 24F, 31, 33F, 34, 35F, and 35B. A pharmaceutical composition or vaccine administered to a subject can comprise can comprise a plurality of saccharide-polypeptide conjugates comprising the serotype 6C and at least one additional serotype selected from 15A, 15C, 16F, 20B, 23A, 23B, 24F, 31, 33B, 34, 35F, and 35B. A pharmaceutical composition or vaccine administered to a subject can comprise can comprise a plurality of saccharide-polypeptide conjugates comprising the serotype 6C and at least one additional serotype selected from 15A, 15C, 16F, 20B, 23A, 23B, 24F, 31, 33F, 34, 35F, and 35B. A pharmaceutical composition or vaccine administered to a subject can comprise can comprise a plurality of saccharide-polypeptide conjugates comprising the serotype 6C and at least one additional serotype selected from 6C, 8, 9N, 10A, 11A, 15A, 15B, 15C, 16F, 20A, 22F, 23A, 23B, 33F, and 35B. A pharmaceutical composition or vaccine administered to a subject can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise a plurality of at least 15 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise a plurality of at least 16 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise a plurality of at least 15 or 16 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 8, 9N, 11A, 12F, 15A, 15B, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise a plurality of at least 15 or 16 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7F, 8, 9N, 10A, 11A, 12F, 15A, 15B, 15C, 16F, 19A, 22F, 23A, 23B, 24F, 33F, 35B, and 38. A pharmaceutical composition or vaccine administered to a subject can comprise a plurality of at least 10 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 8, 9N, 12F, 15A, 19A, 22F, 23A, 23B, and 24F. A pharmaceutical composition or vaccine administered to a subject can comprise a plurality of at least 11 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 8, 9N, 10A, 12F, 15A, 19A, 22F, 23A, 23B, and 24F. A pharmaceutical composition or vaccine administered to a subject can comprise a plurality of at least 24 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 4, 6C, 7C, 7F, 8, 9N, 10A, 11A, 12F, 15A, 15B, 15C, 16F, 19A, 22F, 23A, 23B, 24F, 31, 33F, 35B, 35F, 38, and Serogroup 20 (comprising serotypes 20A and 20B). A pharmaceutical composition or vaccine administered to a subject can comprise a plurality of at least 20 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 8, 9N, 11A, 12F, 15A, 15B, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise a plurality of at least 20, 21, 22, 23, 24, 25, 26, or 27 immunogenic saccharide-polypeptide conjugate comprising individually a capsular polysaccharide, fragment thereof, or combination thereof conjugated to a polypeptide, wherein the capsular polysaccharide, fragment thereof, or combination thereof is from a unique *S. pneumoniae* selected from the group comprising 3, 6C, 7C, 7F, 8, 9N, 10A, 11A, 12F, 15A, 15B, 15C, 16F, 17F, 19A, 19F, 22F, 23A, 23B, 24F, 31, 33F, 34, 35B, 35F, 38 and Serogroup 20 (comprising serotypes 20A and 20B). A pharmaceutical composition or vaccine administered to a subject can comprise at least 20 serotypes selected from the group consisting of 3, 6C, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise at least 20 serotypes selected from the group consisting of 3, 6C, 8, 9N, 11A, 12F, 15A, 15B, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise at least 20 serotypes selected from the group consisting of 3, 6C, 7F, 8, 9N, 10A, 11A, 12F, 15A, 15B, 15C, 16F, 19A, 22F, 23A, 23B, 24F, 33F, 35B, and 38. A pharmaceutical composition or vaccine administered to a subject can comprise at least 10 serotypes selected from the group consisting of 3, 8, 9N, 12F, 15A, 19A, 22F, 23A, 23B, and 24F. A pharmaceutical composition or vaccine administered to a subject can comprise at least 11 serotypes selected from the group consisting of 3, 8, 9N, 10A, 12F, 15A, 19A, 22F, 23A, 23B, and 24F. A pharmaceutical composition or vaccine administered to a subject can comprise at least 24 serotypes selected from the group consisting of 3, 4, 6C, 7F, 8, 9N, 10A, 11A, 12F, 15A, 15B, 15C, 16F, 19A, 22F, 23A, 23B, 24F, 31, 33F, 35B, 35F, 38, and Serogroup 20 (comprising serotypes 20A and 20B). A pharmaceutical composition or vaccine administered to a subject can comprise at least 20 serotypes selected from the group consisting of 3, 6C, 8, 9N, 11A, 12F, 15A, 15B, 16F, 19A, 19F, 22F, 23A, 23B, 31, 33F, 35B, 35F, 38, and Serogroup 20 (comprising serotypes 20A and 20B). A pharmaceutical composition or vaccine administered to a subject can comprise at least 20, 21, 22, 23, 24, 25, 26, or 27 serotypes selected from the group consisting of 3, 6C, 7C, 7F, 8, 9N, 10A, 11A, 12F, 15A, 15B, 15C, 16F, 17F, 19A, 19F, 22F, 23A, 23B, 24F, 31, 33F, 34, 35B, 35F, 38 and Serogroup 20 (comprising serotypes 20A and 20B).

Each dosage can be formulated in 0.5 mL. The formulation can comprise normal saline. The formulation can have a pH of 6.5. The formulation can be a pH from 6.3 to 6.7 or from 6.2 to 6.8. The formulation can have a pH of 5.8. The formulation can be a pH from 5.5 to 6.1 or from 5.6 to 6.0. The formulation can comprise 0.001% to 0.01% polysorbate 80.

A first composition and second composition can be administered to a subject. The first composition and the second composition can be distinct. The first composition can be a first pharmaceutical composition or vaccine. The second composition can be a second pharmaceutical composition or vaccine. The first pharmaceutical composition or vaccine can be administered to the subject at least about four weeks, six weeks, two months, six months, eight months, one year, two years, or five years before or at least about four weeks, six weeks, two months, six months, eight months, one year, two years, or five years after an administration to the subject a second pharmaceutical composition or vaccine. The first pharmaceutical composition or vaccine can be administered to a subject who is at least 4 weeks old, 6 weeks old, 12 weeks old, 24 weeks old, 6 months old, 8 months old, 10 months old, 12 months old, 14 months old, 15 months old, 16 months old, 17 months old, 18 months old, 19 months old, 20 months old, 21 months old, 22 months old, 23 months old, 2 years old or older. The first pharmaceutical composition or vaccine can be administered to a subject with an age from 4 weeks to 2 years old. The first pharmaceutical composition or vaccine can be administered to a subject with an age from 18 years old to 100 years old. The first pharmaceutical composition can be administered to a subject with an age of 100 years old or older. In some embodiments, the second pharmaceutical composition or vaccine can comprise a saccharide-polypeptide conjugate comprising a polypeptide that has at least about 70%, 80%, 90%, 95%, 99%, or 100% length homology, about 70%, 80%, 90%, 95%, 99%, or 100% sequence homology, or a combination thereof to a polypeptide of a saccharide-polypeptide conjugate of the first pharmaceutical composition or vaccine. For example, the polypeptide in a saccharide-conjugate of the first pharmaceutical composition or vaccine and the polypeptide in a saccharide-conjugate of the second pharmaceutical composition or vaccine can be $CRM_{197}$. In other embodiments, the second pharmaceutical composition or vaccine can comprise a saccharide-polypeptide conjugate comprising a polypeptide that has at less than 70% length homology, 70% sequence homology, or a combination thereof to a polypeptide of a saccharide-polypeptide conjugate of the first pharmaceutical composition.

In some embodiments, the first pharmaceutical composition or vaccine can comprise a saccharide-polypeptide conjugate comprising a capsular polysaccharide or immunogenic fragment thereof from a serotype of *S. pneumoniae* conjugated to a polypeptide, and wherein the serotype is not at least 1, 2, 3, 4, 5, 6, 7, 8, 9, 10, 11, 12, or 13, of 1, 3, 4, 5, 6A, 6B, 7F, 9V, 14, 18C, 19A, 19F, or 23F; the serotype is at least one of 2, 6C, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B); or a combination thereof. The first pharmaceutical composition or vaccine can comprise a plurality of saccharide-polypeptide conjugates comprising at least 3, 4, 5, 6, 7, 8, 9, 10, 11, 12, 13, 14, 15, 16, 17, 18, 19, 20, 21, 22, 23, or 24 serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B). The first pharmaceutical composition or vaccine can comprise at least 10, 11, 12, 13, 14, 15, 16, 17, 18, 19, 20, 21, 22 23, or 24 serotypes selected from the group consisting of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B). In some embodiments, the first pharmaceutical composition or vaccine can comprise a saccharide-polypeptide conjugate comprising a capsular polysaccharide or immunogenic fragment thereof from a serotype of *S. pneumoniae* conjugated to a polypeptide, and wherein the serotype is not at least 1, 2, 3, 4, 5, 6, 7, 8, 9, 10, 11, 12, or 13, of 1, 3, 4, 5, 6A, 6B, 7F, 9V, 14, 18C, 19A, 19F, or 23F; the serotype is at least one of 2, 6C, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising 20A and 20B); or a combination thereof. The first pharmaceutical composition or vaccine can comprise a plurality of saccharide-polypeptide conjugates comprising at least 3, 4, 5, 6, 7, 8, 9, 10, 11, 12, 13, 14, 15, 16, 17, 18, 19, 20, 21, 22, 23, or 24 serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising 20A and 20B). The first pharmaceutical composition can comprise at least 10, 11, 12, 13, 14, 15, 16, 17, 18, 19, 20, 21, 22 23, or 24 serotypes selected from the group consisting of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38, and Serogroup 20 (comprising 20A and 20B). The first pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. The first pharmaceutical composition or vaccine can comprise a plurality of saccharide-polypeptide conjugates comprising the serotypes 6C, 8, 9N, 11A, 12F, 15A, 15B, 16F, 22F, 23A, 23B, 24F, 33F, and 35B. The first pharmaceutical composition or vaccine can comprise a plurality of saccharide-polypeptide conjugates comprising the serotypes 6C, 8, 9N, 10A, 11A, 12F, 15A, 22F, 23A, 23B, 24F, 33F, and 35B. The first pharmaceutical composition or vaccine can comprise a plurality of saccharide-polypeptide conjugates comprising the serotypes 6C, 10A, 11A, 15A, 15B, 15C, 22F, 23A, 24B, 33F, 35B, and 38. The first pharmaceutical composition or vaccine can comprise a plurality of saccharide-polypeptide conjugates comprising the serotypes 6C, 8, 9N, 10A, 11A, 15A, 15B, 15C, 16F, 22F, 23A, 23B, 33F, and 35B. The first pharmaceutical composition or vaccine can comprise a plurality of saccharide-polypeptide conjugates comprising the serotypes 6C, 8, 9N, 10A, 11A, 15A, 15B, 15C, 16F, 20B, 22F, 23A, 23B, 33F, and 35B. The first pharmaceutical composition or vaccine can comprise a plurality of saccharide-polypeptide conjugates comprising the serotypes 6C, 8, 9N, 10A, 11A, 15A, 15B, 15C, 16F, 20A, 22F, 23A, 23B, 33F, and 35B. The first pharmaceutical composition or vaccine can comprise a plurality of saccharide-polypeptide conjugates comprising the serotypes 6C, 9N, 15A, 15C, 16F, 23A, 23B, and 33B. The first pharmaceutical composition or vaccine can comprise a plurality of saccharide-polypeptide conjugates comprising the serotypes 6C, 9N, 15A, 15C, 16F, 23A, 23B, and 33F. The first pharmaceutical composition or vaccine can comprise a plurality of saccharide-polypeptide conjugates comprising the serotypes 6C, 15A, 15C, 16F, 23A, 23B, and 33B. The first pharmaceutical composition or vaccine can comprise a plurality of saccharide-polypeptide conjugates comprising the serotypes 6C, 15A, 15C, 16F, 23A, 23B, and 33F. The first pharmaceutical composition or vaccine can comprise a plurality of saccharide-polypeptide conjugates comprising the serotypes 6C, 9N, 15A, 15C, 16F, 17F, 20B, 23A, 23B, 24F, 31, 33B, 34, 35F, and 35B. The first pharmaceutical composition or vaccine can comprise a plurality of saccharide-polypeptide conjugates comprising the serotypes 6C, 9N, 15A, 15C, 16F, 17F, 20B, 23A, 23B, 24F, 31, 33F, 34, 35F, and 35B. The first pharmaceutical composition or vaccine can comprise a plurality of saccharide-polypeptide conjugates comprising the serotypes 6C, 15A, 15C, 16F, 20B, 23A, 23B, 24F, 31, 33B, 34, 35F, and 35B. The first pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. The first pharmaceutical composition or vaccine can comprise a plurality of saccharide-polypeptide conjugates comprising the serotypes 6C, 8, 9N, 11A, 12F, 15A, 15B, 16F, 22F, 23A, 23B, 33F, and 35B. The first pharmaceutical composition or vaccine can comprise a plurality of saccharide-polypeptide conjugates comprising the serotypes 6C, 8, 9N, 10A, 11A, 12F, 15A, 22F, 23A, 23B, 24F, 33F, and 35B. The first pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. The first pharmaceutical composition or vaccine can comprise a plurality of saccharide-polypeptide conjugates comprising the serotypes 6C, 10A, 11A, 15A, 15B, 15C, 22F, 23A, 24B, 33F, 35B and 38. The first pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B. The first pharmaceutical composition or vaccine can comprise a plurality of saccharide-polypeptide conjugates comprising the serotypes 6C, 8, 9N, 11A, 12F, 15A, 15B, 16F, 22F, 23A, 23B, 33F, and 35B. In other embodiments, the first pharmaceutical composition or vaccine can comprise a plurality of saccharide-polypeptide conjugates comprising a serotype that is at least one of 1, 3, 4, 5, 6A, 6B, 7F, 9V, 14, 18C, 19A, 19F, and 23F. The first pharmaceutical composition or vaccine can comprise a plurality of saccharide-polypeptide conjugates comprising the serotypes 1, 3, 4, 5, 6A, 6B, 7F, 9V, 14, 18C, 19A, 19F, and 23F. The first pharmaceutical composition or vaccine can comprise a plurality of saccharide-polypeptide conjugates comprising the serotypes 3, 6C, 7C, 8, 9N, 11A, 12F, 15A, 16F, 19F, 19A, 22F, 23A, 23B, 31, 33F, 35F, 35B, 38 and Serogroup 20 (comprising serotypes 20A and 20B). The first pharmaceutical composition or vaccine can comprise a plurality of saccharide-polypeptide conjugates comprising the serotypes 3, 6C, 7F, 7C, 8, 9N, 11A, 12F, 15A, 16F, 19F, 19A, 22F, 23A, 23B, 31, 33F, 35F, 35B, 38 and Serogroup 20 (comprising serotypes 20A and 20B). The first pharmaceutical composition or vaccine can comprise a plurality of saccharide-polypeptide conjugates comprising the serotypes 3, 6C, 8, 9N, 11A, 12F, 15A, 15B, 16F, 19A, 19F, 22F, 23A, 23B, 31, 33F, 35F, 35B, 38 and Serogroup 20 (comprising serotypes 20A and 20B). The first pharmaceutical composition or vaccine can comprise a plurality of saccharide-polypeptide conjugates comprising the serotypes 3, 8, 9N, 12F, 15A, 19A, 22F, 23A, 23B, and 24F. The first pharmaceutical composition or vaccine can comprise a plurality of saccharide-polypeptide conjugates comprising the serotypes 3, 6C, 7F, 8, 9N, 10A, 11A, 12F, 15A, 15B, 15C, 16F, 19A, 22F, 23A, 23B, 24F, 33F, 35B, and 38. The first pharmaceutical composition or vaccine can comprise a plurality of saccharide-polypeptide conjugates comprising the serotypes 3, 8, 9N, 10A, 12F, 15A, 19A, 22F, 23A, 23B, and 24F. The first pharmaceutical composition or vaccine can comprise a plurality of saccharide-polypeptide conjugates comprising the serotypes 3, 4, 6C, 7F, 8, 9N, 10A, 11A, 12F, 15A, 15B, 15C, 16F, 19A, 22F, 23A, 23B, 24F, 31, 33F, 35F, 35B, 38 and Serogroup 20 (comprising serotypes 20A and 20B). The first pharmaceutical composition or vaccine can comprise a plurality of saccharide-polypeptide conjugates comprising the serotypes 3, 6C, 8, 9N, 11A, 12F, 15A, 15B, 16F, 19A, 19F, 22F, 23A, 23B, 31, 33F, 35B, 35F, 38 and Serogroup 20 (comprising serotypes 20A and 20B). When administering any of the first pharmaceutical compositions or vaccines described above, the first pharmaceutical composition or vaccine can be distinct from the second pharmaceutical composition or vaccine administered to a subject.

In some embodiments, the second pharmaceutical composition or vaccine can comprise a plurality of saccharide-polypeptide conjugates comprising a serotype that is at least one of 1, 3, 4, 5, 6A, 6B, 7F, 9V, 14, 18C, 19A, 19F, and 23F. The second pharmaceutical composition or vaccine can comprise a plurality of saccharide-polypeptide conjugates comprising the serotypes 1, 3, 4, 5, 6A, 6B, 7F, 9V, 14, 18C, 19A, 19F, and 23F. The second pharmaceutical composition or vaccine can comprise a plurality of saccharide-polypeptide conjugates comprising a serotype that is at least one of 2, 6C, 8, 9N, 10A, 11A, 12F, 15A, 15B, 15C, 16F, 17F, 22F, 23A, 23B, 24B, 24F, 31, 33F, 33B, 35B, 35F, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising a serotype that is at least one of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising 20A and 20B), wherein the serotype of the first pharmaceutical composition or vaccine and the serotype of the second pharmaceutical composition or vaccine are distinct. The second pharmaceutical composition or vaccine can comprise a saccharide-polypeptide conjugate comprising a capsular polysaccharide or immunogenic fragment thereof from a serotype of S. pneumoniae conjugated to a polypeptide, and wherein the serotype is not at least 1, 2, 3, 4, 5, 6, 7, 8, 9, 10, 11, 12, or 13, of 1, 3, 4, 5, 6A, 6B, 7F, 9V, 14, 18C, 19A, 19F, or 23F; and the serotype is at least one of 2, 6C, 8, 9N, 10A, 11A, 12F, 15A, 15B, 15C, 16F, 17F, 22F, 23A, 23B, 24F, 24B, 31, 33F, 33B, 35F, 35B, 38 and Serogroup 20 (comprising serotypes 20A and 20B); wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising at least 3, 4, 5, 6, 7, 8, 9, 10, 11, 12, 13, 14, 15, 16, 17, 18, 19, 20, 21, 22, 23, or 24 serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise at least 10, 11, 12, 13, 14, 15, 16, 17, 18, 19, 20, 21, 22, 23, or 24 serotypes selected from the group consisting of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise a saccharide-polypeptide conjugate comprising a capsular polysaccharide or immunogenic fragment thereof from a serotype of S. pneumoniae conjugated to a polypeptide, and wherein the serotype is not at least 1, 2, 3, 4, 5, 6, 7, 8, 9, 10, 11, 12, or 13, of 1, 3, 4, 5, 6A, 6B, 7F, 9V, 14, 18C, 19A, 19F, or 23F; and the serotype is at least one of 2, 6C, 8, 9N, 10A, 11A, 12F, 15A, 15B, 15C, 16F, 17F, 22F, 23A, 23B, 24F, 24B, 31, 33F, 33B, 34, 35F, 35B, 38, and Serogroup 20 (comprising 20A and 20B); wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising at least 3, 4, 5, 6, 7, 8, 9, 10, 11, 12, 13, 14, 15, 16, 17, 18, 19, 20, 21, 22, 23, or 24 serotypes selected from the group consisting of 2, 6C, 8, 9N, 10A, 11A, 12F, 15A, 15B, 15C, 16F, 17F, 22F, 23A, 23B, 24B, 24F, 31, 33F, 33B, 34, 35B, 35F, 38, and Serogroup 20 (comprising 20A and 20B), wherein the serotype of the first pharmaceutical composition or vaccine and the serotype of the second pharmaceutical composition or vaccine are distinct. The second pharmaceutical composition or vaccine can comprise at least 10, 11, 12, 13, 14, 15, 16, 17, 18, 19, 20, 21, 22, 23, or 24 serotypes selected from the group consisting of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38, and Serogroup 20 (comprising 20A and 20B), wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 11A, 12F, 15A, 15B, 16F, 22F, 23A, 23B, 24F, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 12F, 15A, 22F, 23A, 23B, 24F, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 10A, 11A, 15A, 15B, 15C, 22F, 23A, 24B, 33F, 35B, and 38, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 15A, 15B, 15C, 16F, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 15A, 15B, 15C, 16F, 20B, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 15A, 15B, 15C, 16F, 20A, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 9N, 15A, 15C, 16F, 23A, 23B, and 33B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 9N, 15A, 15C, 16F, 23A, 23B, and 33F, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 15A, 15C, 16F, 23A, 23B, and 33B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 15A, 15C, 16F, 23A, 23B, and 33F, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 9N, 15A, 15C, 16F, 17F, 20B, 23A, 23B, 24F, 31, 33B, 34, 35F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 9N, 15A, 15C, 16F, 17F, 20B, 23A, 23B, 24F, 31, 33F, 34, 35F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 15A, 15C, 16F, 20B, 23A, 23B, 24F, 31, 33B, 34, 35F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 15A, 15C, 16F, 20B, 23A, 23B, 24F, 31, 33F, 34, 35F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 11A, 12F, 15A, 15B, 16F, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 12F, 15A, 22F, 23A, 23B, 24F, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 10A, 11A, 15A, 15B, 15C, 22F, 23A, 24B, 33F, 35B, and 38, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 10A, 11A, 12F, 15A, 15B, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 6C, 8, 9N, 11A, 12F, 15A, 15B, 16F, 22F, 23A, 23B, 33F, and 35B, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 6C, 7C, 8, 9N, 11A, 12F, 15A, 16F, 19F, 19A, 22F, 23A, 23B, 31, 33F, 35F, 35B, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 6C, 7F, 7C, 8, 9N, 11A, 12F, 15A, 16F, 19F, 19A, 22F, 23A, 23B, 31, 33F, 35F, 35B, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 6C, 8, 9N, 11A, 12F, 15A, 15B, 16F, 19A, 19F, 22F, 23A, 23B, 31, 33F, 35F, 35B, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 8, 9N, 12F, 15A, 19A, 22F, 23A, 23B, and 24F, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 6C, 7F, 8, 9N, 10A, 11A, 12F, 15A, 15B, 15C, 16F, 19A, 22F, 23A, 23B, 24F, 33F, 35B, and 38, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 8, 9N, 10A, 12F, 15A, 19A, 22F, 23A, 23B, and 24F, wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 4, 6C, 7F, 8, 9N, 10A, 11A, 12F, 15A, 15B, 15C, 16F, 19A, 22F, 23A, 23B, 24F, 31, 33F, 35F, 35B, 38 and Serogroup 20 (comprising serotypes 20A and 20B), wherein the serotype of the first pharmaceutical composition or vaccine and the serotype of the second pharmaceutical composition or vaccine are distinct. The second pharmaceutical composition or vaccine can comprise a plurality of saccharide-polypeptide conjugates comprising the serotypes 3, 6C, 8, 9N, 11A, 12F, 15A, 15B, 16F, 19A, 19F, 22F, 23A, 23B, 31, 33F, 35B, 35F, 38 and Serogroup 20 (comprising serotypes 20A and 20B), wherein the serotype of the first pharmaceutical composition or vaccine and the serotype of the second pharmaceutical composition or vaccine are distinct.

In other embodiments, the first pharmaceutical composition or vaccine and the second pharmaceutical composition or vaccine can be administered at least about 4 weeks apart, at least 6 about weeks apart, at least 2 about months apart, at a least about 3 months apart, at least about 4 months apart, at least about 5 months apart, at least 6 months apart, at least about 7 months apart, at least about 8 months apart, at least about 9 months apart, at least about 10 months apart, at least 11 about months apart, at least about 1 year apart, at least about 1.5 years apart, at least about 2 years apart, at least about 5 years apart, at least about 10 years apart, at least about 15 year, at least about 20 years apart, or at least about 30 years apart.

In some embodiments, a serotype of the first pharmaceutical composition or vaccine can be from a different bacteria than the serotype of the second pharmaceutical composition or vaccine. For example, the serotype of the first composition or vaccine can be from *Streptococcus pneumoniae*, and the serotype of the second composition or vaccine can be from *Neisseria meningitidis, Salmonella enterica,* or *Haemophilus influenzae*. The serotype of the first pharmaceutical composition or vaccine can be from *Neisseria meningitidis, Salmonella enterica,* or *Haemophilus influenzae*, and the serotype of the second pharmaceutical composition or vaccine can be from *Streptococcus pneumoniae*.

In some embodiments, a serotype of the first pharmaceutical composition or vaccine can be from the same bacteria as a serotype for the second pharmaceutical composition or vaccine. For example, the first pharmaceutical composition or vaccine can comprise at least one of 1, 3, 4, 5, 6A, 6B, 7F, 9V, 14, 18C, 19A, 19F, and 23F from *Streptococcus pneumoniae*, and the second pharmaceutical composition or vaccine can comprise at least one of 2, 6C, 8, 9N, 10A, 11A, 12F, 15A, 15B, 15C, 16F, 17F, 22F, 23A, 23B, 24F, 24B, 31, 33F, 34, 35B, 35F 38 and Serogroup 20 (comprising serotypes 20A and 20B) from *Streptococcus pneumoniae*. The first pharmaceutical composition or vaccine can comprise at least one of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38 and Serogroup 20 (comprising serotypes 20A and 20B), from *Streptococcus pneumoniae*, and the second pharmaceutical composition or vaccine can comprise at least one of 1, 3, 4, 5, 6A, 6B, 7F, 9V, 14, 18C, 19A, 19F, and 23F from *Streptococcus pneumoniae*. The first pharmaceutical composition or vaccine can comprise at least one of 1, 3, 4, 5, 6A, 6B, 7F, 9V, 14, 18C, 19A, 19F, and 23F from *Streptococcus pneumoniae*, and the second pharmaceutical composition or vaccine can comprise at least one of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38, and Serogroup 20 (comprising serotypes 20A and 20B) from *Streptococcus pneumoniae*. The first pharmaceutical composition or vaccine can comprise at least one of 2, 6C, 8, 9N, 10A, 11A, 12F, 15A, 15B, 15C, 16F, 17F, 22F, 23A, 23B, 24F, 24B, 31, 33F, 33B, 34, 35B, 35F, 38, and Serogroup 20 (comprising serotypes 20A and 20B) from *Streptococcus pneumoniae*, and the second pharmaceutical composition or vaccine can comprise at least one of 1, 3, 4, 5, 6A, 6B, 7F, 9V, 14, 18C, 19A, 19F, and 23F from *Streptococcus pneumoniae*. The first pharmaceutical composition or vaccine can comprise at least one of 1, 3, 4, 5, 6A, 6B, 7F, 9V, 14, 18C, 19A, 19F, and 23F from *Streptococcus pneumoniae*, and the second pharmaceutical composition or vaccine can comprise at least one of 6C, 8, 9N, 10A, 11A, 12F, 15A, 15B, 15C, 16F, 22F, 23A, 23B, 33F, and 35B from *Streptococcus pneumoniae*. The first pharmaceutical composition or vaccine can comprise at least one of 6C, 8, 9N, 10A, 11A, 12F, 15A, 15B, 15C, 16F, 22F, 23A, 23B, 33F, and 35B from *Streptococcus pneumoniae*, and the second pharmaceutical composition or vaccine can comprise at least one of 1, 3, 4, 5, 6A, 6B, 7F, 9V, 14, 18C, 19A, 19F, and 23F from *Streptococcus pneumoniae*. The first pharmaceutical composition or vaccine can comprise at least one of 1, 3, 4, 5, 6A, 6B, 7F, 9V, 14, 18C, 19A, 19F, and 23F from *Streptococcus pneumoniae*, and the second pharmaceutical composition or vaccine comprises at least one of 6C, 8, 9N, 10A, 11A, 12F, 15A, 15B, 15C, 16F, 22F, 23A, 23B, 33F, 35B and Serogroup 20 (comprising serotypes 20A and 20B) from *Streptococcus pneumoniae*. The first pharmaceutical composition or vaccine can comprise at least one of 6C, 8, 9N, 10A, 11A, 12F, 15A, 15B, 15C, 16F, 22F, 23A, 23B, 33F, 35B, and Serogroup 20 (comprising serotypes 20A and 20B) from *Streptococcus pneumoniae*, and the second pharmaceutical composition or vaccine can comprise at least one of 1, 3, 4, 5, 6A, 6B, 7F, 9V, 14, 18C, 19A, 19F, and 23F from *Streptococcus pneumoniae*. The first pharmaceutical composition or vaccine can comprise at least one of 1, 3, 4, 5, 6A, 6B, 7F, 9V, 14, 18C, 19A, 19F, and 23F from *Streptococcus pneumoniae*, and the second pharmaceutical composition or vaccine can comprise at least one of 6C, 8, 9N, 10A, 11A, 12F, 15A, 15B, 15C, 16F, 22F, 23A, 23B, 33F, 35B, and Serogroup 20 (comprising serotypes 20A and 20B) from *Streptococcus pneumoniae*. The first pharmaceutical composition or vaccine can comprise at least one of 6C, 8, 9N, 10A, 11A, 12F, 15A, 15B, 15C, 16F, 22F, 23A, 23B, 33F, 35B and Serogroup 20 (comprising serotypes 20A and 20B) from *Streptococcus pneumoniae*, and the second pharmaceutical composition or vaccine can comprise at least one of 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 8, 9N, 10A, 11A, 12F, 15A, 15B, 15C, 16F, 22F, 23A, 23B, 33F, and 35B from *Streptococcus pneumoniae*. The first pharmaceutical composition or vaccine can comprise the serotypes 6C, 8, 9N, 10A, 11A, 12F, 15A, 15B, 15C, 16F, 22F, 23A, 23B, 33F, and 35B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 8, 9N, 10A, 11A, 12F, 15A, 15B, 15C, 16F, 20B, 22F, 23A, 23B, 33F, and 35B from *Streptococcus pneumoniae*. The first pharmaceutical composition or vaccine can comprise the serotypes 6C, 8, 9N, 10A, 11A, 12F, 15A, 15B, 15C, 16F, 20B, 22F, 23A, 23B, 33F, and 35B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 9N, 15A, 15C, 16F, 23A, 23B, and 33B from *Streptococcus pneumoniae*. The first pharmaceutical composition or vaccine can comprise the serotypes 6C, 9N, 15A, 15C, 16F, 23A, 23B, and 33B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 15A, 15C, 16F, 23A, 23B, and 33B from *Streptococcus pneumoniae*. The first pharmaceutical composition or vaccine can comprise the serotypes 6C, 15A, 15C, 16F, 23A, 23B, and 33B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 9N, 15A, 15C, 16F, 17F, 20B, 23A, 23B, 24F, 31, 33B, 34, 35F, and 35B from *Streptococcus pneumoniae*. The first pharmaceutical composition or vaccine can comprise the serotypes 6C, 9N, 15A, 15C, 16F, 17F, 20B, 23A, 23B, 24F, 31, 33B, 34, 35F, and 35B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 15A, 15C, 16F, 20B, 23A, 23B, 24F, 31, 33B, 34, 35F, and 35B from *Streptococcus pneumoniae*. The first pharmaceutical composition or vaccine can comprise the serotypes 6C, 15A, 15C, 16F, 20B, 23A, 23B, 24F, 31, 33B, 34, 35F, and 35B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 8, 9N, 10A, 11A, 15A, 15B, 15C, 16F, 20A, 22F, 23A, 23B, 33F, and 35B from *Streptococcus pneumoniae*. The first pharmaceutical composition or vaccine can comprise the serotypes 6C, 8, 9N, 10A, 11A, 15A, 15B, 15C, 16F, 20A, 22F, 23A, 23B, 33F, and 35B from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*. The first pharmaceutical composition or vaccine can comprise the serotypes 1, 3, 4, 5, 6A, 6B, 7F, 9V, 14, 18C, 19A, 19F, and 23F from *Streptococcus pneumoniae*, and the second pharmaceutical composition or vaccine can comprise the serotypes 6C, 8, 9N, 10A, 11A, 12F, 15A, 15B, 15C, 16F, 22F, 23A, 23B, 33F, 35B, and Serogroup 20 (comprising serotypes 20A and 20B) from *Streptococcus pneumoniae*. The first pharmaceutical composition or vaccine can comprise the serotypes 6C, 8, 9N, 10A, 11A, 12F, 15A, 15B, 15C, 16F, 22F, 23A, 23B, 33F, 35B, and Serogroup 20 (comprising serotypes 20A and 20B) from *Streptococcus pneumoniae*, and the second pharmaceutical composition or vaccine can comprise the serotypes 1, 3, 4, 5, 6A, 6B, 7F, 9V, 14, 18C, 19A, 19F, and 23F from *Streptococcus pneumoniae*.

Different serotypes of *S. pneumoniae* can be more pervasive or endemic in different geographical areas. For example, a certain group of serotypes can commonly cause pneumococcal disease in the United States and Canada. This group of serotypes can be different for Europe, the Middle East, North Africa, Japan and Korea. For example, administration of a pharmaceutical composition or vaccine to a subject comprising a plurality of saccharide-polypeptide conjugates comprising the serotypes 3, 4, 6A, 6B, 6C, 7F, 8, 9N, 10A, 11A, 12F, 15A, 15B, 15C, 16F, 19F, 19A, 20A, 22F, 23A, 23B, 33F, 35F, 35B, and 38 can improve protection against *S. pneumoniae* disease for the subject in the United States and/or Canada. Administration of a pharmaceutical composition or vaccine to a subject comprising a plurality of saccharide-polypeptide conjugates comprising the serotypes 3, 4, 6A, 6B, 6C, 7F, 8, 9N, 10A, 11A, 12F, 15A, 15B, 15C, 16F, 19F, 19A, 22F, 23A, 23B, 33F, 35F, 35B, 38 and Serogroup 20 (comprising serotypes 20A and 20B) can improve protection against *S. pneumoniae* disease for the subject in the United States and/or Canada. Administration of a pharmaceutical composition or vaccine to a subject comprising a plurality of saccharide-polypeptide conjugates comprising the serotypes 3, 6C, 7C, 8, 9N, 11A, 12F, 15A, 16F, 19F, 19A, 22F, 23A, 23B, 31, 33F, 35F, 35B, 38 and Serogroup 20 (comprising serotypes 20A and 20B) can improve protection against *S. pneumoniae* disease for the subject in the United States. Administration of a pharmaceutical composition or vaccine to a subject comprising a plurality of saccharide-polypeptide conjugates comprising the serotypes 3, 6C, 7F, 7C, 8, 9N, 11A, 12F, 15A, 16F, 19F, 19A, 22F, 23A, 23B, 31, 33F, 35F, 35B, 38 and Serogroup 20 (comprising serotypes 20A and 20B) can improve protection against *S. pneumoniae* disease for the subject in the United States. Administration of a pharmaceutical composition or vaccine to a subject comprising a plurality of saccharide-polypeptide conjugates comprising the serotypes 3, 6C, 8, 9N, 11A, 12F, 15A, 15B, 16F, 19A, 19F, 22F, 23A, 23B, 31, 33F, 35F, 35B, 38 and Serogroup 20 (comprising serotypes 20A and 20B) can improve protection against *S. pneumoniae* disease for the subject in the United States. Administration of a pharmaceutical composition or vaccine to a subject comprising a plurality of saccharide-polypeptide conjugates comprising the serotypes 3, 8, 9N, 12F, 15A, 19A, 22F, 23A, 23B, and 24F can improve protection against *S. pneumoniae* disease for the subject in the United States. Administration of a pharmaceutical composition or vaccine to a subject comprising a plurality of saccharide-polypeptide conjugates comprising the serotypes 3, 6C, 7F, 8, 9N, 10A, 11A, 12F, 15A, 15B, 15C, 16F, 19A, 22F, 23A, 23B, 24F, 33F, 35B, and 38 can improve protection against *S. pneumoniae* disease for the subject in the United Kingdom. Administration of a pharmaceutical composition or vaccine to a subject comprising a plurality of saccharide-polypeptide conjugates comprising the serotypes 3, 8, 9N, 10A, 12F, 15A, 19A, 22F, 23A, 23B, and 24F can improve protection against *S. pneumoniae* disease for the subject in the United Kingdom or in Europe. Administration of a pharmaceutical composition or vaccine to a subject comprising a plurality of saccharide-polypeptide conjugates comprising the serotypes 3, 4, 6C, 7F, 8, 9N, 10A, 11A, 12F, 15A, 15B, 15C, 16F, 19A, 22F, 23A, 23B, 24F, 31, 33F, 35F, 35B, 38 and Serogroup 20 (comprising serotypes 20A and 20B) can improve protection against *S. pneumoniae* disease for the subject in Germany. Administration of a pharmaceutical composition or vaccine to a subject comprising a plurality of saccharide-polypeptide conjugates comprising the serotypes 3, 6C, 8, 9N, 11A, 12F, 15A, 15B, 16F, 19A, 19F, 22F, 23A, 23B, 31, 33F, 35B, 35F, 38 and Serogroup 20 (comprising serotypes 20A and 20B) can improve protection against *S. pneumoniae* disease for the subject in Germany. Administration of a pharmaceutical composition or vaccine to a subject comprising a plurality of saccharide-polypeptide conjugates comprising the serotypes 1, 3, 4, 6A, 6B, 6C, 7F, 8, 9N, 10A, 11A, 12F, 14, 15A, 15B, 16F, 18C, 19F, 19A, 22F, 23F, 23A, 23B, 24F, 33F, 35F, 35B, and 38 can improve protection against *S. pneumoniae* disease for the subject in the Europe, the Middle East, and/or North Africa. Administration of a pharmaceutical composition or vaccine to a subject comprising a plurality of saccharide-polypeptide conjugates comprising the serotypes 3, 4, 6A, 6B, 6C, 7F, 10A, 11A, 14, 15A, 15B, 15C, 19F, 19A, 22F, 23F, 23A, 24F, 35F, 35B, and 38 can improve protection against *S. pneumoniae* disease for the subject in the Japan and/or Korea. Additionally, invasive clinical disease can be caused by serotype 20B (as opposed to serotype 20A). The subject can be a human who resides in the specific geographical location as indicated above, or can be a human who is visiting the specific geographical location as indicated above.

A method of administration can comprise administering a first saccharide-polypeptide conjugate composition to a subject; administering a second saccharide-polypeptide conjugate composition to the subject at least four weeks after administering the first saccharide-polypeptide conjugate composition; wherein the first saccharide-polypeptide conjugate composition comprises a first polypeptide that has at least about 70%, 80%, 90%, 95%, 99%, or 100% length homology, about 70%, 80%, 90%, 95%, 99%, or 100% sequence homology, or a combination thereof to a second polypeptide of the second saccharide-polypeptide conjugate composition; and wherein the first saccharide-polypeptide conjugate composition comprises a first serotype; wherein the second saccharide-polypeptide conjugate composition comprises a second serotype, and wherein the first serotype and the second serotype are different. In some embodiments, the first serotype is from the same bacteria as the second serotype. For example, the polypeptide in a saccharide-conjugate of the first pharmaceutical composition and the polypeptide in a saccharide-conjugate of the second pharmaceutical composition can be $CRM_{197}$. In other embodiments, the second pharmaceutical composition comprises a saccharide-polypeptide conjugate comprising a polypeptide that has at less than about 70% length homology, about 70% sequence homology, or a combination thereof to a polypeptide of a saccharide-polypeptide conjugate of the first pharmaceutical composition. The first saccharide-polypeptide conjugate composition can be a vaccine comprising a plurality of unique immunogenic saccharide-polypeptide conjugates that can comprise individually a capsular polysaccharide, fragment thereof, or combination thereof conjugated to a polypeptide, wherein the capsular polysaccharide, fragment thereof, or combination thereof can be from a unique *Streptococcus pneumoniae* serotype selected from a group consisting of 23A and 23B in a vaccine. The first saccharide-polypeptide conjugate composition can be a vaccine comprising at least 2 immunogenic saccharide-polypeptide conjugates that can each comprise individually a capsular polysaccharide, fragment thereof, or combination thereof conjugated to a polypeptide, wherein the capsular polysaccharide, fragment thereof, or combination thereof can be from a unique *Streptococcus pneumoniae* serotype group, wherein one serotype can be 23A and at least one additional serotype can be selected from the group consisting of 1, 2, 3, 4, 5, 6A, 6B, 6C, 7F, 9V, 14, 18C, 19A, 19F, 23F, 8, 9N, 10A, 11A, 12F, 15A, 15B, 15C, 16F, 17F, 20A, 20B, 22F, 23B, 24F, 24B, 31, 33F, 33B, 34, 35B, 35F, and 38. The first saccharide-polypeptide conjugate composition can be a vaccine comprising at least 2 immunogenic saccharide-polypeptide conjugates that can each comprise individually a capsular polysaccharide, fragment thereof, or combination thereof conjugated to a polypeptide, wherein the capsular polysaccharide, fragment thereof, or combination thereof can be from a unique *Streptococcus pneumoniae* serotype group, wherein one serotype can be 23B and at least one additional serotype can be selected from the group consisting of 1, 2, 3, 4, 5, 6A, 6B, 6C, 7F, 9V, 14, 18C, 19A, 19F, 23F, 8, 9N, 10A, 11A, 12F, 15A, 15B, 15C, 16F, 17F, 20A, 20B, 22F, 23A, 24F, 24B, 31, 33F, 33B, 34, 35B, 35F, and 38. The second saccharide-polypeptide conjugate composition can be a vaccine comprising a plurality of unique immunogenic saccharide-polypeptide conjugates that can comprise individually a capsular polysaccharide, fragment thereof, or combination thereof conjugated to a polypeptide, wherein the capsular polysaccharide, fragment thereof, or combination thereof can be from a unique *Streptococcus pneumoniae* serotype selected from a group consisting of 23A and 23B. The second saccharide-polypeptide conjugate composition be a vaccine comprising at least 2 immunogenic saccharide-polypeptide conjugates that can each comprise individually a capsular polysaccharide, fragment thereof, or combination thereof conjugated to a polypeptide, wherein the capsular polysaccharide, fragment thereof, or combination thereof can be from a unique *Streptococcus pneumoniae* serotype group, wherein one serotype can be 23A and at least one additional serotype can be selected from the group consisting of 1, 2, 3, 4, 5, 6A, 6B, 6C, 7F, 9V, 14, 18C, 19A, 19F, 23F, 8, 9N, 10A, 11A, 12F, 15A, 15B, 15C, 16F, 17F, 20A, 20B, 22F, 23B, 24F, 24B, 31, 33F, 33B, 34, 35B, 35F, and 38, in a vaccine. The second saccharide-polypeptide conjugate composition can be a vaccine comprising at least 2 immunogenic saccharide-polypeptide conjugates that can each comprise individually a capsular polysaccharide, fragment thereof, or combination thereof conjugated to a polypeptide, wherein the capsular polysaccharide, fragment thereof, or combination thereof can be from a unique *Streptococcus pneumoniae* serotype group, wherein one serotype can be 23B and at least one additional serotype can be selected from the group consisting of 1, 2, 3, 4, 5, 6A, 6B, 6C, 7F, 9V, 14, 18C, 19A, 19F, 23F, 8, 9N, 10A, 11A, 12F, 15A, 15B, 15C, 16F, 17F, 20A, 20B, 22F, 23A, 24F, 24B, 31, 33F, 33B, 34, 35B, 35F, and 38. The first saccharide-polypeptide conjugate composition and the second saccharide-polypeptide conjugate composition can be distinct.

In other embodiments, the conducting of any of the methods described herein may not result in more than about: 50%, 40%, 30%, 20%, 10%, 5%, 4%, 3%, 2%, or 1% suppression of an immunity conveyed by a first vaccine containing an immunogenic saccharide-polypeptide conjugate, as measured by antibody response to the saccharide of the immunogenic saccharide-polypeptide conjugate, wherein the antibody response is measured by measuring antibody titers.

Saccharide-polypeptide Conjugate Kits

The saccharide-polypeptide conjugates, pharmaceutical compositions, and vaccines described herein can be contained in a kit. The kit can further comprise instructions for use. The saccharide-polypeptide conjugates and/or pharmaceutical compositions and/or vaccines can be stored in a container. The container can be a syringe. The container can be a vial. The vial can be a 2 mL borosilicate glass vial. The vial can be 3 mL Vials USP Type I glass, non-siliconized. The top can be an aluminum crimp top. The container can be a vial with a rubber septum or a septum made of flexible, reclose-able material. The container can be a vial with a stopper. The stopper can be a non-siliconized stopper. The vial can have a fill volume of 0.6 mL. The extractable volume can be 0.5 mL.

EXAMPLES

The following examples are included to further describe some aspects of the present disclosure, and should not be used to limit the scope of the embodiments described herein.

Example 1

Method of Establishing a Cell Bank

Figure 2:
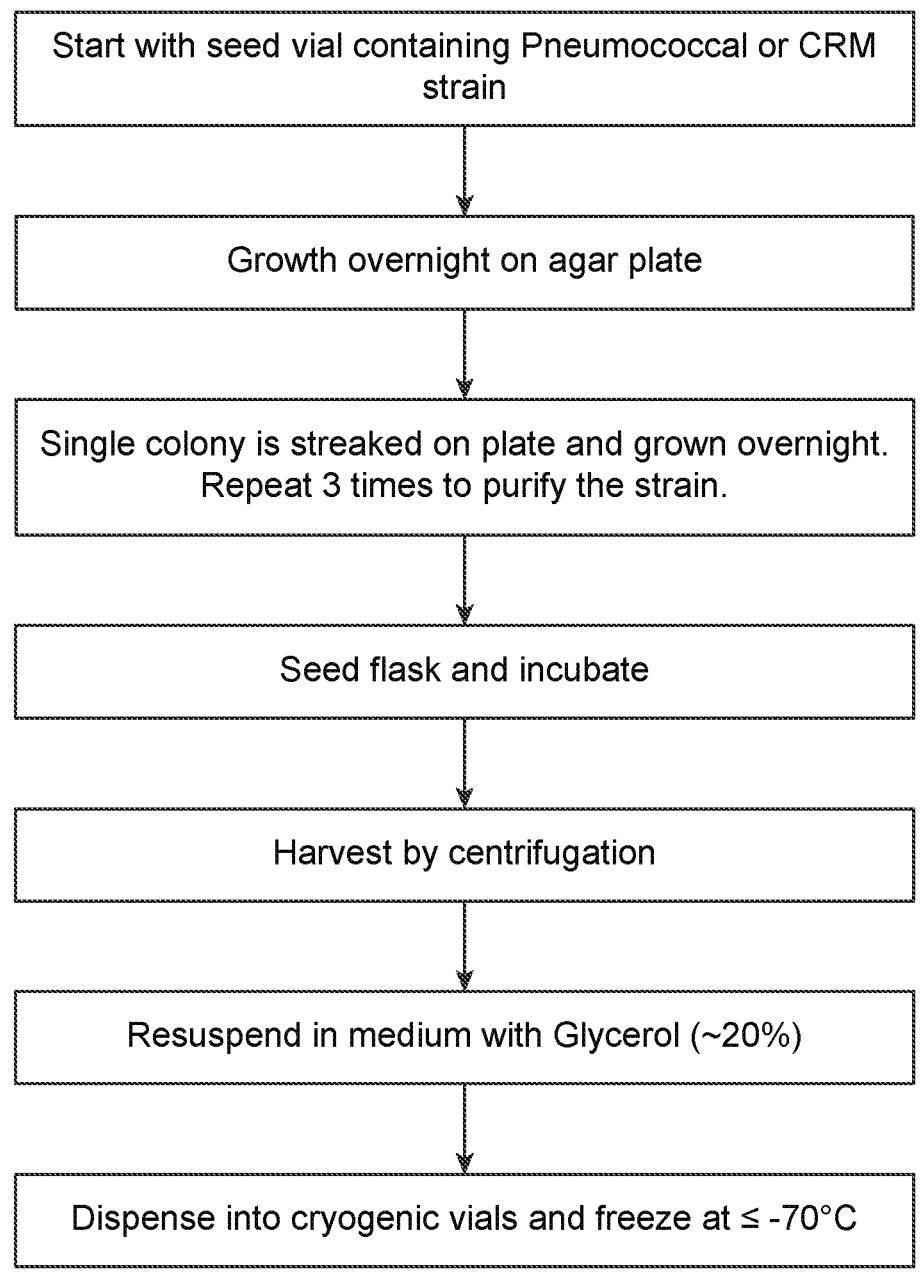
FIG. 2 illustrates a flow diagram of a process for cell banking of a bacterial strain.

This example shows the establishment of a cell bank for a *S. pneumoniae* strain for use in producing polysaccharides for a polysaccharide-$CRM_{197}$ conjugate vaccine. Any strain that produces the polysaccharides of TABLE 1 or of FIGS. 10A-10F (e.g., polysaccharides from serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 35F, 35B, or 38 and Serogroup 20 (comprising serotypes 20A and 20B)) are established as a cell bank by this method. A *S. pneumoniae* strain is provided by either the Center for Disease Control and Prevention (CDC), United States or the Culture Collection, University of Gothenburg (CCUG). The cell bank process is depicted in FIG. 2. A vial of a strain of *S. pneumoniae* is seeded and then is grown overnight on an agar plate. A single colony is picked from this plate and streaked onto a new agar plate for overnight growth. This process is repeated three times to purify the strain before a flask is seeded and is incubated. After allowing the seeded flask sufficient time for growth, the flask contents are harvested by centrifugation. The centrifugation product is resuspended in a medium of about 20% glycerol and then is dispensed into cryogenic vials. The cell bank is contained in the cryogenic vials, which are stored at −70° C. until use.

*S. pneumoniae* strains that produce serotype 6C polysaccharide was acquired by the University of Alabama, Birmingham (UAB) for establishing a 6C cell bank. The cell bank process is depicted in FIG. 2. For 6C polysaccharide serotype, a vial of the strain of *S. pneumoniae* is seeded and then is grown overnight on an agar plate. A single colony is picked from this plate and streaked onto a new agar plate for overnight growth. This process is repeated three times to purify the strain before a flask is seeded and is incubated. After allowing the seeded flask sufficient time for growth, the flask contents are harvested by centrifugation. The centrifugation product is resuspended in a medium of about 20% glycerol and then is dispensed into cryogenic vials. The cell bank for each strain are contained in the cryogenic vials, which are stored at −70° C. until use.

*S. pneumoniae* strains that produce serotype 8 polysaccharide, serotype 10A polysaccharide, serotype 11A polysaccharide, serotype 12F polysaccharide, serotype 22F polysaccharide, or serotype 33F polysaccharide were acquired by either the Center for Disease Control and Prevention (CDC), United States or the Culture Collection, University of Gothenburg (CCUG) for establishing a cell bank. The cell bank process is depicted in FIG. 2. For each polysaccharide serotype, a vial of the strain of *S. pneumoniae* was seeded and then was grown overnight on an agar plate. A single colony was picked from this plate and streaked onto a new agar plate for overnight growth. This process was repeated three times to purify the strain before a flask was seeded and was incubated. After allowing the seeded flask sufficient time for growth, the flask contents were harvested by centrifugation. The centrifugation product was resuspended in a medium of about 20% glycerol and then was dispensed into cryogenic vials. The cell bank for each strain were contained in the cryogenic vials, which were stored at −70° C. until use.

Example 2

Method of Isolating and Purifying Polysaccharides

Figure 4:
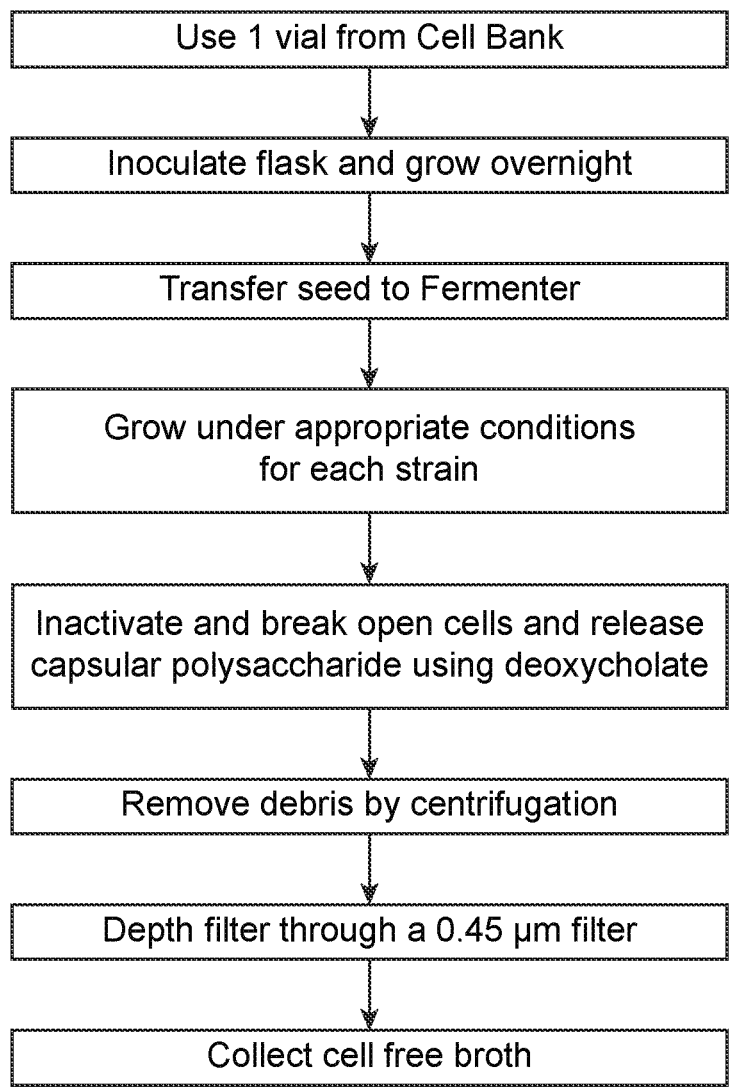
FIG. 4 illustrates a flow diagram of a fermentation process for isolating a polysaccharide from a strain of *Streptococcus pneumoniae*.

This examples shows how polysaccharides are isolated and purified from cell banks for use in a polysaccharide-$CRM_{197}$ conjugate vaccine. Any of the polysaccharides of TABLE 1 or of FIGS. 10A-10F (e.g., polysaccharides from serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33B, 33F, 34, 35F, 35B, or 38 and Serogroup 20 (comprising serotypes 20A and 20B)) are isolated and purified by this method. This process for the isolation and purification of polysaccharides is shown in FIG. 4. A vial of a cell bank produced as described in EXAMPLE 1 is used to inoculate a flask containing an appropriate culture medium and incubated overnight. This culture is used to seed a new culture for fermentation in a fermenter. The culture is allowed to grow under the appropriate conditions for that strain. After fermentation, the cells are inactivated and then are treated with deoxycholate to break open the cells and release the capsular polysaccharide. Subsequently, debris is removed by centrifugation, which is followed by a depth filter step through a 0.45 µm filter and the cell free broth is collected. The product is then purified and the polysaccharide size is determined. Quality control tests are performed on the product, such as a purity assay and confirmation of strain inactivation (no growth after plating).

A cell bank of an *S. pneumoniae* strain that produces serotype 8, serotype 10A, serotype 11A, serotype 12F, serotype 22F, or serotype 33F was used to inoculate a flask containing the appropriate culture medium and incubated overnight. This culture was used to seed a new culture for fermentation in a fermenter. The culture was allowed to grow under the appropriate conditions for the specific strain. After fermentation, the cells were inactivated and then were treated with deoxycholate to break open the cells and release the capsular polysaccharide. Subsequently, debris was removed by centrifugation, which was followed by a depth filter step through a 0.45 µm filter and the cell free broth was collected. The product was then purified and the polysaccharide size was determined. Quality control tests were performed on the product, such as a purity assay and confirmation of strain inactivation (no growth after plating).

Example 3

Method of $CRM_{197}$ Production

Figure 3:
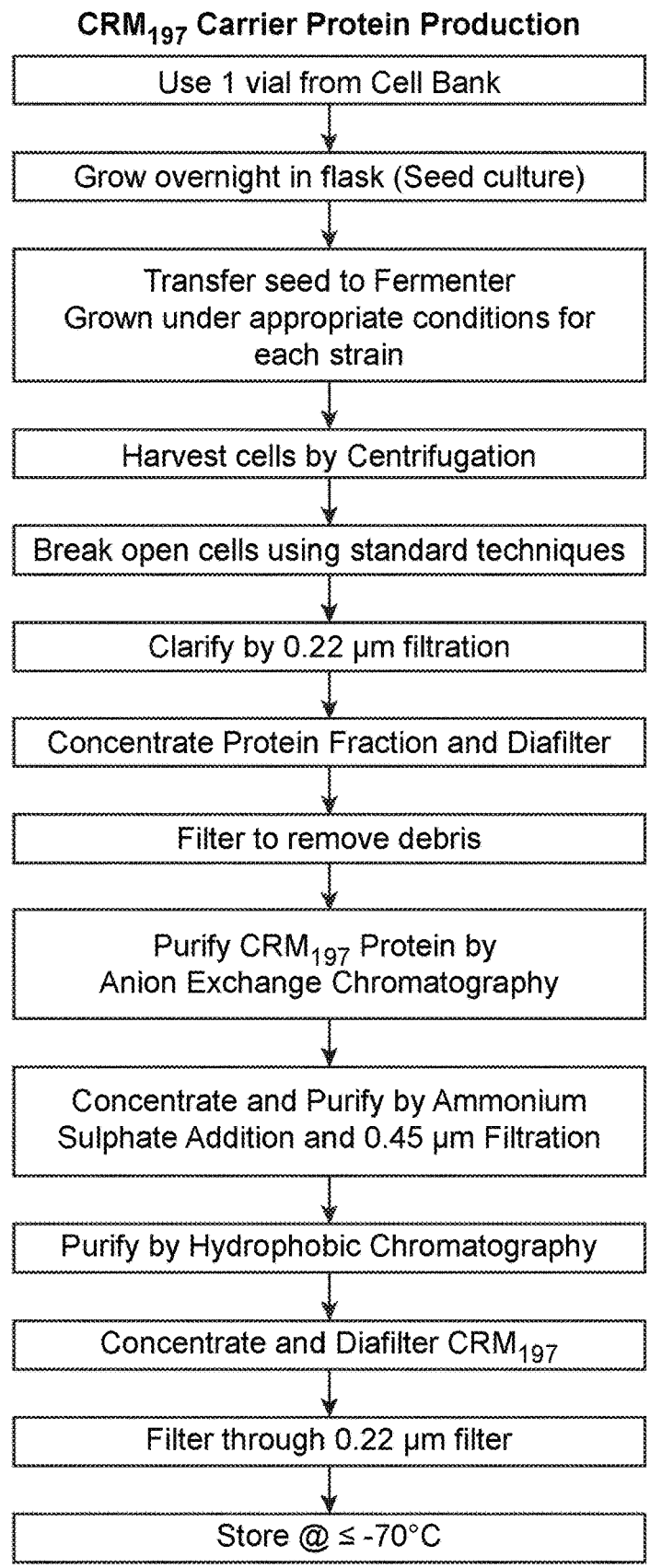
FIG. 3 illustrates a flow diagram of a process for producing, isolating, and purifying $CRM_{197}$.

This example shows the production of $CRM_{197}$ (SEQ ID NO: 1) for use in saccharide polypeptide vaccines, which is depicted in FIG. 3. A vial from a working cell bank of $CRM_{197}$ was seeded into a flask containing the appropriate culture medium and incubated overnight. The fermentation culture was centrifuged and the contents were harvested, were clarified, and then were filtered through a 0.2 µm filter. The filtrate was concentrated about ten-fold, and then was diafiltered to exchange the buffer and remove contaminants. The protein was further purified by microfiltration using an appropriate pore size membrane. Then the filtrate was further purified by anion exchange chromatography, followed by ammonium sulfate precipitation, and filtration (0.45 µm). A final purification using hydrophobic chromatography was conducted, and the highly purified $CRM_{197}$ protein was concentrated and diafiltered, and then filtered through a 0.2 µm filter. The product was stored at −70° C. until use in conjugation with a polysaccharide, such as any polysaccharide listed in TABLE 1 or of FIGS. 10A-10F (e.g., polysaccharides from serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B)). Quality control tests were performed on the product to assess concentration (BCA for Lowry NLT 15 mg/mL), purity (SDS-PAGE gel with a target of ≥95% pure), confirming $CRM_{197}$ identification (using a monoclonal antibody), assessing size (SDS-Page with a target of ~58 kDa), assessing endotoxin level (LAL kit with target of <1 IU/µg of protein), assessing lack of toxicity (Vero Cytotoxicity or DT enzyme test; non-lethal in Guinea Pigs), assessing pH (meter, target of 6.5±0.2), and assessing appearance (visually, target for clear liquid).

Example 4

Method of Conjugation

This example shows the conjugation of a capsular polysaccharide to a polypeptide via CDAP conjugation chemistry. The polysaccharide are isolated as described in EXAMPLE 2 and are thawed. The polypeptide is chosen from any of the following: diphtheria and tetanus toxoids, and variants thereof (e.g., DT, $CRM_{197}$, TT), cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B *streptococcus*, non-typable *H. influenzae* P4 protein, non-typable *H. influenzae* P6 protein, *M catarrhalis* uspA, keyhole limpet haemocyanin (KLH), OMPC from *N. meningitidis*, the purified protein derivative of tuberculin (PPD), protein D from *H. influenzae*, or any fragment thereof. The polysaccharide is activated via CDAP chemistry in a CDAP solution. The polypeptide is added to the activated polysaccharides, and then the conjugation reaction is quenched. The reaction mixture is filtered, is diafiltrated, and is concentrated. The polysaccharide polypeptide conjugates are then separated using gel filtration chromatography. These conjugates are then concentrated for the final polysaccharide polypeptide conjugate.

Example 5

Method of Polysaccharide-$CRM_{197}$ Conjugation

Figure 5:
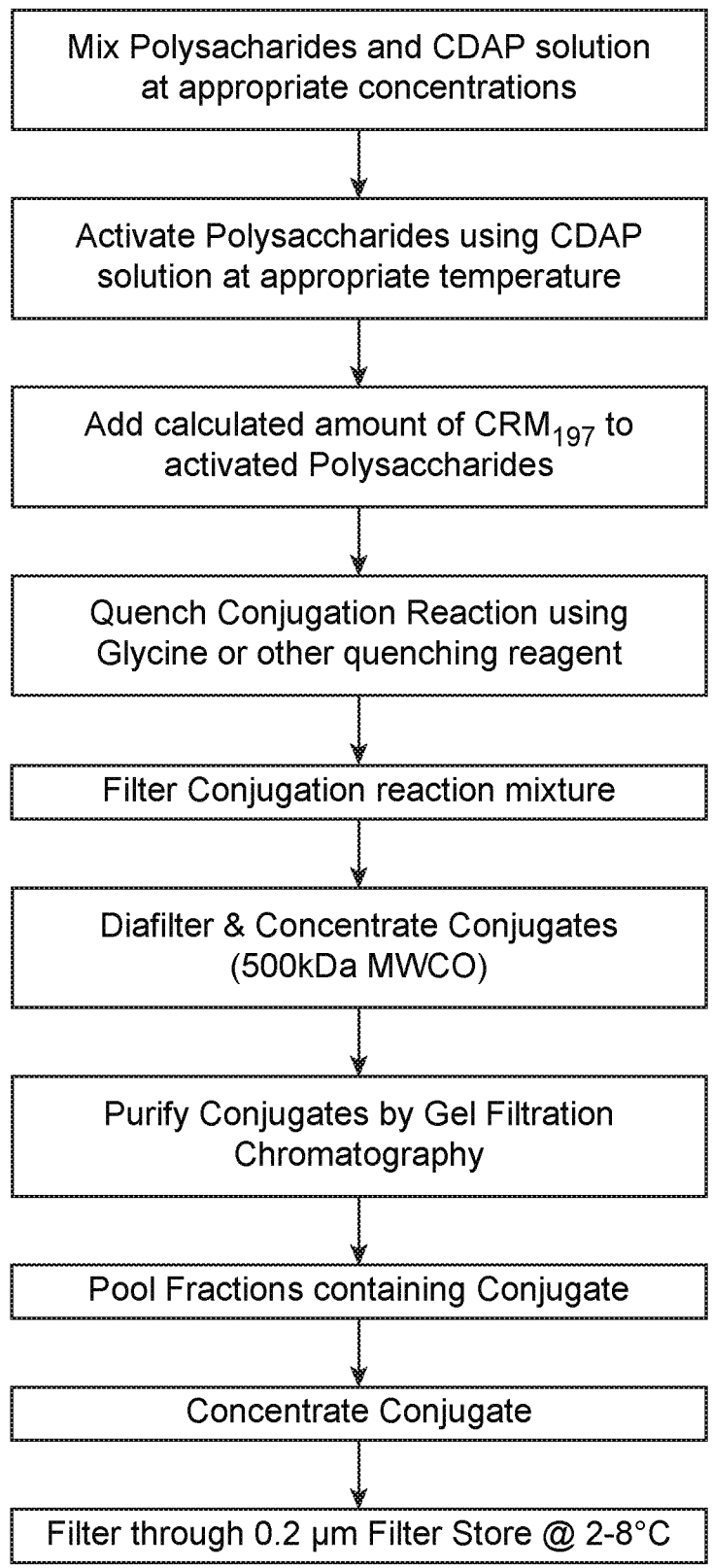
FIG. 5 illustrates a flow diagram of a conjugation process for conjugating a polysaccharide and $CRM_{197}$.

This example shows the conjugation of a capsular polysaccharide to $CRM_{197}$ via CDAP conjugation chemistry. The isolated polysaccharide is any polysaccharide as described in TABLE 1 or of FIGS. 10A-10F (e.g., polysaccharides from serotypes 1, 2, 3, 4, 5, 6A, 6B, 7C, 7F, 9V, 14, 18C, 19A, 19F, 23F, 6C, 8, 9N, 10A, 11A, 12F, 15A, 15B, 15C, 16F, 17F, 22F, 23A, 23B, 24F, 24B, 31, 33F, 33B, 34, 35F, 35B, 38 and Serogroup 20 (comprising serotypes 20A and 20B)), or in EXAMPLE 2, and $CRM_{197}$ is as described in EXAMPLE 3. The conjugation process is depicted in FIG. 5. The polysaccharide and $CRM_{197}$ are thawed. The polysaccharide is mixed with CDAP solution, which is then incubated at the appropriate temperature for polysaccharide activation. A calculated amount of $CRM_{197}$ is added to the activated polysaccharides. The reaction is then quenched using glycine or any other suitable quenching reagent. The conjugation reaction mixture is filtered, is diafiltered, and is concentrated for the polysaccharide-$CRM_{197}$ conjugates. The polysaccharide-$CRM_{197}$ conjugates are then purified by gel filtration chromatography. The fractions containing the polysaccharide-$CRM_{197}$ conjugates are pooled, are concentrated, and then are filtered through a 0.2 µm filter. The product is stored at 2-8° C.

The isolated polysaccharide from serotype 8, serotype 10A, serotype 11A, serotype 12F, serotype 22F, or serotype 33F as described in TABLE 1 and EXAMPLE 2, and $CRM_{197}$ as described in EXAMPLE 3 were thawed. The polysaccharide from serotype 8, serotype 10A, serotype 11A, serotype 12F, serotype 22F, or serotype 33F were mixed with CDAP solution, which was then incubated at the appropriate temperature for polysaccharide activation. A calculated amount of $CRM_{197}$ was added to the activated polysaccharides. The reaction was then quenched using glycine or any other suitable quenching reagent. The conjugation reaction mixture was filtered, was diafiltered, and was concentrated for the polysaccharide-$CRM_{197}$ conjugates. The polysaccharide-$CRM_{197}$ conjugates were then purified by gel filtration chromatography. The fractions containing the polysaccharide-$CRM_{197}$ conjugates were pooled, were concentrated, and then were filtered through a 0.2 µm filter. The product is stored at 2-8° C.

Example 6

Combinations of Polysaccharide-$CRM_{197}$ Conjugates in a Vaccine Composition

This example shows combinations of polysaccharides that are used in a polysaccharide-$CRM_{197}$ conjugate vaccine. Each polysaccharide serotype is individually conjugated to a $CRM_{197}$ to produce the polysaccharide $CRM_{197}$ conjugate. The polysaccharide-$CRM_{197}$ conjugates for each serotype are combined into vaccine composition. See the below TABLE 3 for exemplary polysaccharide-$CRM_{197}$ conjugate serotype combinations.

TABLE 3

Combinations of Polysaccharides in Polysaccharide-$CRM_{197}$ Conjugate Vaccines List of Polysaccharide Serotype Combinations 1, 3, 4, 5, 6A, 6B, 7F, 9V, 14, 18C, 19A, 19F, and 23F
6C, 8, 9N, 10A, 12F, 15A, 15B, 15C, 16F, 22F, 23A, 23B, 33F, and 35B
6C, 8, 9N, 10A, 11A, 12F, 15A, 15B, 22F, 23A, 23B, 33F, and 35B
6C, 8, 9N, 11A, 12F, 15A, 15B, 16F, 22F, 23A, 23B, 24F, 33F, and 35B
6C, 8, 9N, 10A, 11A, 12F, 15A, 22F, 23A, 23B, 24F, 33F, and 35B
6C, 8, 9N, 10A, 11A, 12F, 15A, 15B, 22F, 23A, 23B, 33F, and 35B
6C, 8, 9N, 11A, 12F, 15A, 15B, 16F, 22F, 23A, 23B, 33F, and 35B
6C, 8, 9N, 10A, 11A, 12F, 15A, 15B, 15C, 16F, 22F, 23A, 23B, 33F, and 35B
6C, 8, 9N, 10A, 11A, 12F, 15A, 22F, 23A, 23B, 24F, 33F, and 35B
6C, 10A, 11A, 15A, 15B, 15C, 22F, 23A, 24B, 33F, 35B and 38
6C, 8, 9N, 11A, 12F, 15A, 15B, 16F, 22F, 23A, 23B, 33F, and 35B
1, 3, 4, 6A, 6B, 6C, 7F, 8, 9N, 10A, 11A, 12F, 14, 15A, 15B, 15C, 16F, 19F, 19A, 20A, 22F, 23A, 23B, 24F, 33F, 35F, 35B, and 38
3,4, 6C, 7F, 8, 9N, 11A, 12F, 15A, 15B, 15C, 16F, 19A, 22F, 23A, 23B, and 35B
1, 3, 4, 6A, 6C, 7F, 8, 9N, 10A, 11A, 12F, 14, 19A, 19F, 22F, 23A, 23B, 23F, 24F, and 33F
3, 4, 6B, 6C, 10A, 15A, 15B, 19A, 19F, 22F, 23F, 24F, and 35B
6C, 9N, 15A, 15C, 16F, 20A, 23A, 23B, 24F, 31, 34, 35F, and 38
6C, 15A, 15C, 16F, 23A, 23B, 24F, 31, 34, 35F, and 38

TABLE 3-continued

Combinations of Polysaccharides in Polysaccharide-CRM$_{197}$ Conjugate Vaccines 6C, 15A, 15C, 16F, 23A, 23B, and 35B
6C, 9N, 15A, 15C, 16F, 23A, 23B, and 35B
6C, 9N, 15A, 15C, 16F, 23A, 23B, 33F, and 35B
6C, 9N, 15A, 15C, 16F, 17F, 20A, 23A, 23B, 33F, 34, 35F, 35B, 24F, and 31
6C, 9N, 15A, 15C, 16F, 17F, 20B, 23A, 23B, 33F, 34, 35F, 35B, 24F, and 31
6C, 9N, 15A, 15C, 16F, 23A, 23B, 33F, 35F, and 35B
1, 3, 4, 6A, 6B, 6C, 7F, 8, 9N, 10A, 11A, 12F, 14, 15A, 15B, 15C, 16F, 19F, 19A, 20A, 22F, 23A, 23B, 24F, 33F, 35F, 35B, and 38
1, 2, 3, 4, 5, 6A, 6B, 6C, 7F, 8, 9N, 9V, 10A, 11A, 12F, 14, 15A, 15B, 15C, 16F, 17F, 19F, 19A, 20A, 22F, 23F, 23A, 23B, 24F, 31, 33F, 35F, 35B, and 38
1, 3, 4, 5, 6A, 6B, 6C, 7F, 8, 9N, 9V, 10A, 11A, 12F, 14, 15A, 15B, 15C, 16F, 17F, 18C, 20A, 22F, 23F, 23A, 23B, 24F, 31, 33F, 35F, 35B, and 38
6C, 15A, 15C, 16F, 23A, 23B, 31, 33F, 34, 35B, and 38
1, 4, 6A, 6C, 7F, 8, 9N, 10A, 11A, 12F, 15A, 15C, 16F, 17F, 19F, 19A, 20A, 22F, 23A, 23B, 31, 33F, 34, 35B, 35F, 38
1, 3, 4, 6A, 6C, 7F, 8, 9N, 10A, 11A, 12F, 15A, 15C, 16F, 17F, 19F, 19A, 20A, 22F, 23A, 23B, 24F, 31, 33F, 34, 35B, 35F, and 38
1, 3, 4, 5, 6A, 6B, 7F, 9V, 14, 18C, 19A, 19F, 20B, and 23F
6C, 8, 9N, 10A, 12F, 15A, 15B, 15C, 16F, 20B, 22F, 23A, 23B, 33F, and 35B
6C, 8, 9N, 10A, 11A, 12F, 15A, 15B, 20B, 22F, 23A, 23B, 33F, and 35B
6C, 8, 9N, 11A, 12F, 15A, 15B, 16F, 20B, 22F, 23A, 23B, 24F, 33F, and 35B
6C, 8, 9N, 10A, 11A, 12F, 15A, 15B, 20B, 22F, 23A, 23B, 24F, 33F, and 35B
6C, 8, 9N, 10A, 11A, 12F, 15A, 15B, 20B, 22F, 23A, 23B, 33F, and 35B
6C, 8, 9N, 11A, 12F, 15A, 15B, 16F, 20B, 22F, 23A, 23B, 33F, and 35B
6C, 8, 9N, 10A, 11A, 12F, 15A, 15B, 15C, 16F, 20B, 22F, 23A, 23B, 33F, and 35B
6C, 8, 9N, 10A, 11A, 12F, 15A, 20B, 22F, 23A, 23B, 24F, 33F, and 35B
6C, 10A, 11A, 15A, 15B, 15C, 20B, 22F, 23A, 24B, 33F, 35B and 38
6C, 8, 9N, 11A, 12F, 15A, 15B, 16F, 20B, 22F, 23A, 23B, 33F, and 35B
1, 3, 4, 6A, 6B, 6C, 7F, 8, 9N, 10A, 11A, 12F, 14, 15A, 15B, 15C, 16F, 19F, 19A, 20A, 20B, 22F, 23A, 23B, 24F, 33F, 35F, 35B, and 38
3,4, 6C, 7F, 8, 9N, 11A, 12F, 15A, 15B, 15C, 16F, 19F, 20B, 22F, 23A, 23B, and 35B
1, 3, 4, 6A, 6C, 7F, 8, 9N, 10A, 11A, 12F, 14, 19A, 19F, 20B, 22F, 23A, 23B, 23F, 24F, and 33F
3, 4, 6B, 6C, 10A, 15A, 15B, 19A, 19F, 20B, 22F, 23F, 24F, and 35B
6C, 9N, 15A, 15C, 16F, 20A, 20B, 23A, 23B, 24F, 31, 34, 35F, and 38
6C, 15A, 15C, 16F, 20B, 23A, 23B, 24F, 31, 34, 35F, and 38
6C, 15A, 15C, 16F, 20B, 23A, 23B, and 35B
6C, 9N, 15A, 15C, 16F, 20B, 23A, 23B, and 35B
6C, 9N, 15A, 15C, 16F, 20B, 23A, 23B, 33F, and 35B
6C, 9N, 15A, 15C, 16F, 17F, 20A, 20B, 23A, 23B, 33F, 34, 35F, 35B, 24F, and 31
6C, 9N, 15A, 15C, 16F, 20B, 23A, 23B, 33F, 35F, and 35B
1, 3, 4, 6A, 6B, 6C, 7F, 8, 9N, 10A, 11A, 12F, 14, 15A, 15B, 15C, 16F, 19F, 19A, 20A, 20B, 22F, 23A, 23B, 24F, 33F, 35F, 35B, and 38
1, 2, 3, 4, 5, 6A, 6B, 6C, 7F, 8, 9N, 9V, 10A, 11A, 12F, 14, 15A, 15B, 15C, 16F, 17F, 19F, 19A, 20A, 20B, 22F, 23F, 23A, 23B, 24F, 31, 33F, 35F, 35B, and 38
1, 3, 4, 5, 6A, 6B, 6C, 7F, 8, 9N, 9V, 10A, 11A, 12F, 14, 15A, 15B, 15C, 16F, 17F, 18C, 20B, 22F, 23F, 23A, 23B, 24F, 31, 33F, 35F, 35B, and 38
6C, 15A, 15C, 16F, 20B, 23A, 23B, 31, 35B, 34, 35F, and 38
1, 4, 6A, 6C, 7F, 8, 9N, 10A, 11A, 12F, 15A, 15C, 16F, 17F, 19F, 19A, 20B, 22F, 23A, 23B, 31, 33F, 34, 35B, 35F, 38
1, 3, 4, 6A, 6B, 6C, 7F, 8, 9N, 10A, 11A, 12F, 14, 15A, 15B, 15C, 16F, 19F, 19A, 20B, 22F, 23A, 23B, 24F, 33F, 35F, 35B, and 38
6C, 9N, 15A, 15C, 16F, 20B, 23A, 23B, 24F, 31, 34, 35F, and 38
1, 2, 3, 4, 5, 6A, 6B, 6C, 7F, 8, 9N, 9V, 10A, 11A, 12F, 14, 15A, 15B, 15C, 16F, 17F, 19F, 19A, 20B, 22F, 23F, 23A, 23B, 24F, 31, 33F, 35F, 35B, and 38
1, 3, 4, 5, 6A, 6B, 6C, 7F, 8, 9N, 9V, 10A, 11A, 12F, 14, 15A, 15B, 15C, 16F, 17F, 18C, 20B, 22F, 23F, 23A, 23B, 24F, 31, 33F, 35F, 35B, and 38
1, 4, 6A, 6C, 7F, 8, 9N, 10A, 11A, 12F, 15A, 15C, 16F, 17F, 19F, 19A, 20B, 22F, 23A, 23B, 31, 33F, 34, 35B, 35F, 38
1, 3, 4, 6A, 6C, 7F, 8, 9N, 10A, 11A, 12F, 15A, 15C, 16F, 17F, 19F, 19A, 20B, 22F, 23A, 23B, 24F, 31, 33F, 34, 35B, 35F, and 38
6C, 15A, 15C, 16F, 20B, 23A, 23B, 24F, 31, 34, 35F, and 35B
6C, 8, 9N, 10A, 11A, 15A, 15B, 15C, 16F, 20A, 22F, 23A, 23B, 33F, and 35B
6C, 15A, 15C, 16F, 20B, 23A, 23B, 24F, 31, 33F, 34, 35F, and 35B
6C, 9N, 15A, 15C, 16F, 23A, 23B, and 33F
6C, 15A, 15C, 16F, 23A, 23B, and 33F
6C, 9N, 15A, 15C, 16F, 17F, 20B, 23A, 23B, 24F, 31, 33F, 34, 35F, and 35B
3, 6C, 7C, 8, 9N, 11A, 12F, 15A, 16F, 19A, 19F, 20 (comprising 20A and 20B), 22F, 23A, 23B, 31, 33F, 35B, 35F, and 38
3, 6C, 7C, 7F, 8, 9N, 11A, 12F, 15A, 16F, 19A, 19F, 20 (comprising 20A and 20B), 22F, 23A, 23B, 31, 33F, 35B, 35F, and 38
3, 6C, 8, 9N, 11A, 12F, 15A, 15B, 16F, 19A, 19F, (comprising 20A and 20B), 22F, 23A, 23B, 31, 33F, 35B, 35F, 38
3, 6C, 7F, 8, 9N, 10A, 11A, 12F, 15A, 15B, 15C, 16F, 19A, 22F, 23A, 23B, 24F, 33F, 35B, and 38
3, 8, 9N, 12F, 15A, 19A, 22F, 23A, 23B, and 24F
3, 8, 9N, 10A, 12F, 15A, 19A, 22F, 23A, 23B, and 24F
3, 4, 6C, 7F, 8, 9N, 10A, 11A, 12F, 15A, 15B, 15C, 16F, 19A, (comprising 20A and 20B), 22F, 23A, 23B, 24F, 31, 33F, 35B, 35F, and 38
3, 6C, 8, 9N, 11A, 12F, 15A, 15B, 16F, 19A, 19F, (comprising 20A and 20B), 22F, 23A, 23B, 31, 33F, 35B, 35F, and 38

Example 7

Formulation of Polysaccharide-CRM$_{197}$ Conjugate Vaccine

This example shows a formulation for a polysaccharide-CRM$_{197}$ conjugate vaccine. Any combination of polysaccharide-CRM$_{197}$ conjugates from EXAMPLE 5 or the combinations listed in EXAMPLE 6 are used in the vaccine composition. In addition to the polysaccharide-CRM$_{197}$ conjugates, the vaccine is composed of normal saline and 0.01% Polysorbate 80, with a pH of 6.5±0.2. This formulation of the polysaccharide CRM$_{197}$ vaccine composition is stored in 2 mL glass vials with an aluminum crimp top and stopper at 2-8° C. The vial is filled to a volume of 0.60 mL to allow for an extractable volume of 0.50 mL.

Example 8

Process for Formulating a Polysaccharide-CRM$_{197}$ Conjugate Vaccine

Figure 6:
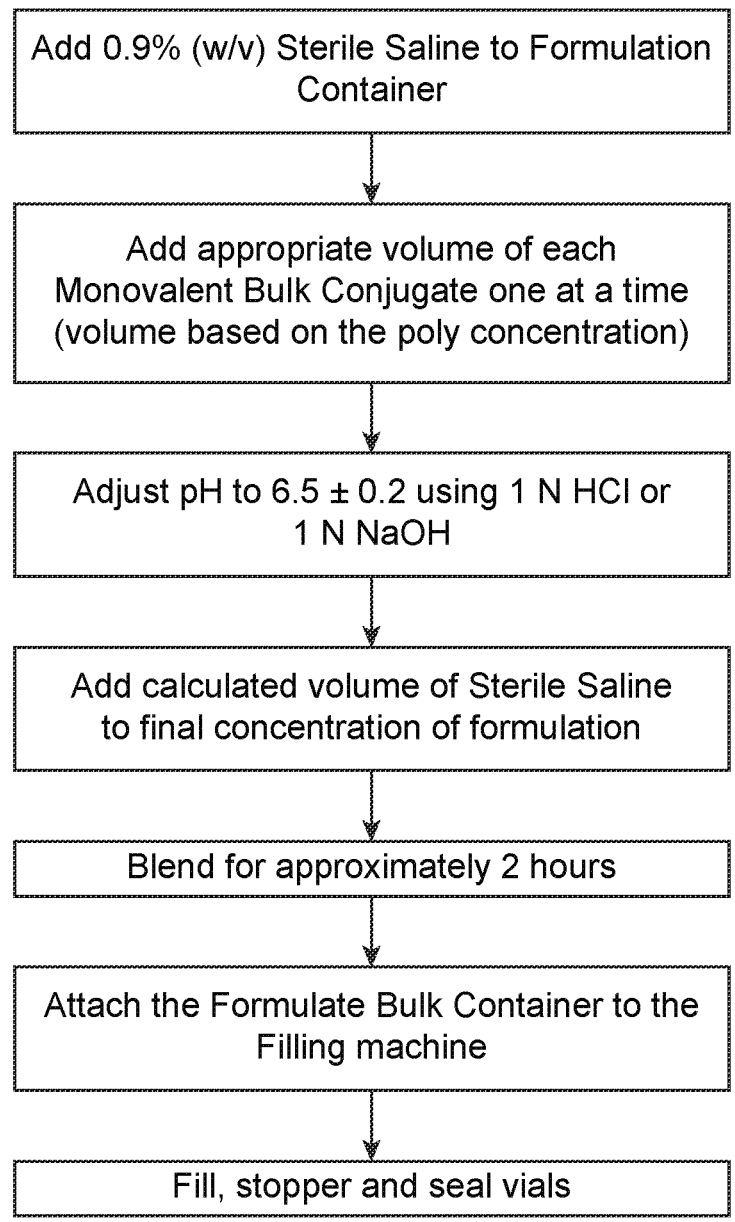
FIG. 6 illustrates a flow diagram for a process for formulating a polysaccharide polypeptide conjugate vaccine.
Figure 7:
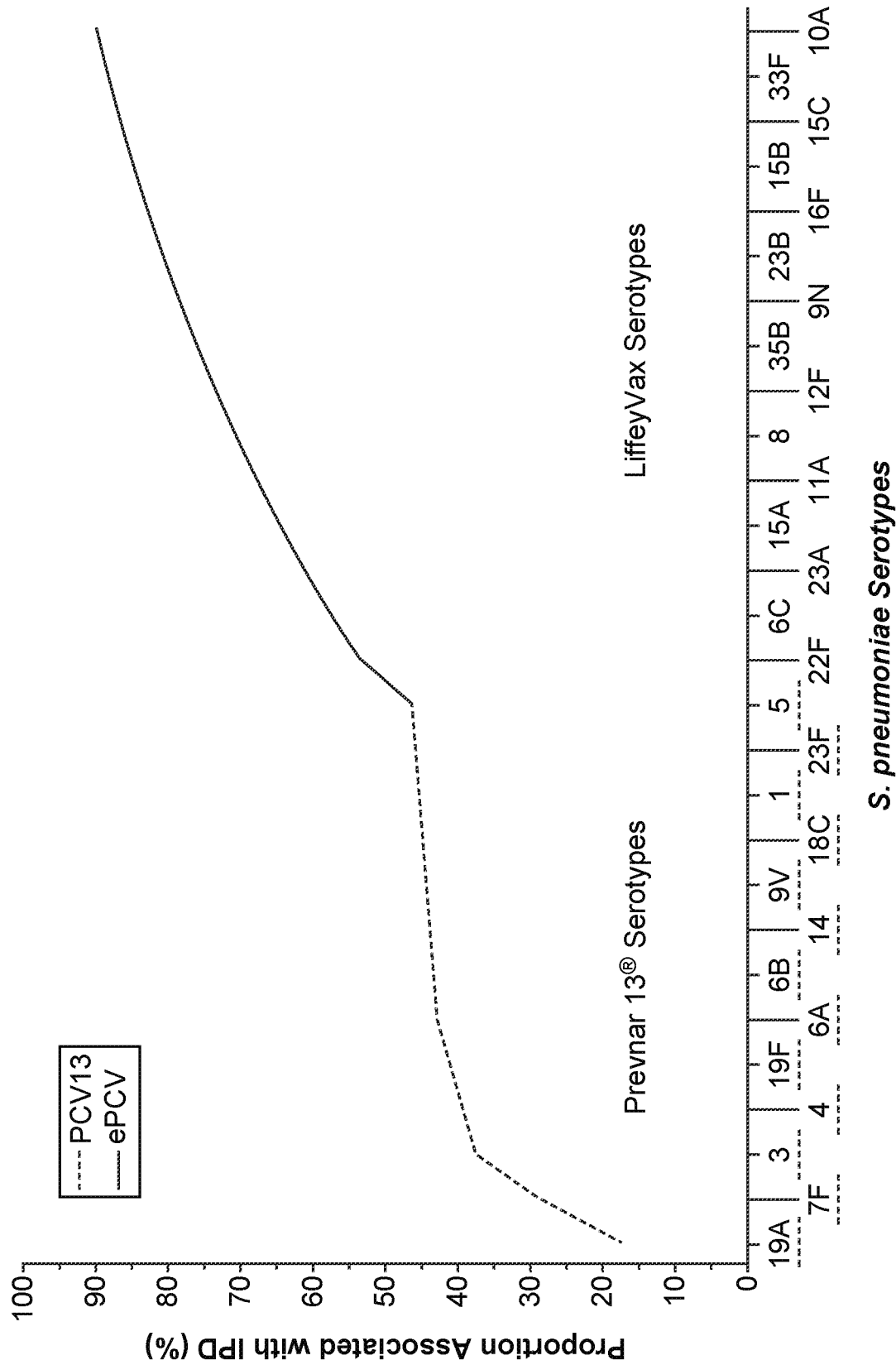
FIG. 7 illustrates the projected expanded coverage provided by a *Streptococcus pneumoniae* polypeptide conjugate vaccine comprising *Streptococcus pneumoniae* serotypes 6C, 8, 9N, 10A, 11A, 12F, 15A, 15B, 15C, 16F, 22F, 23A, 23B, 33F, and 35B (ePCV; LiffeyVax Serotypes) against invasive pneumococcal disease (IPD) in United States and Canada when this vaccine is administered in a vaccination regime with Prevnar 13 (PCV13). Prevnar 13 alone only covers about 46.1% of IPD compared to an overall coverage of 90% when administered in a vaccination regime with ePCV.
Figure 8:
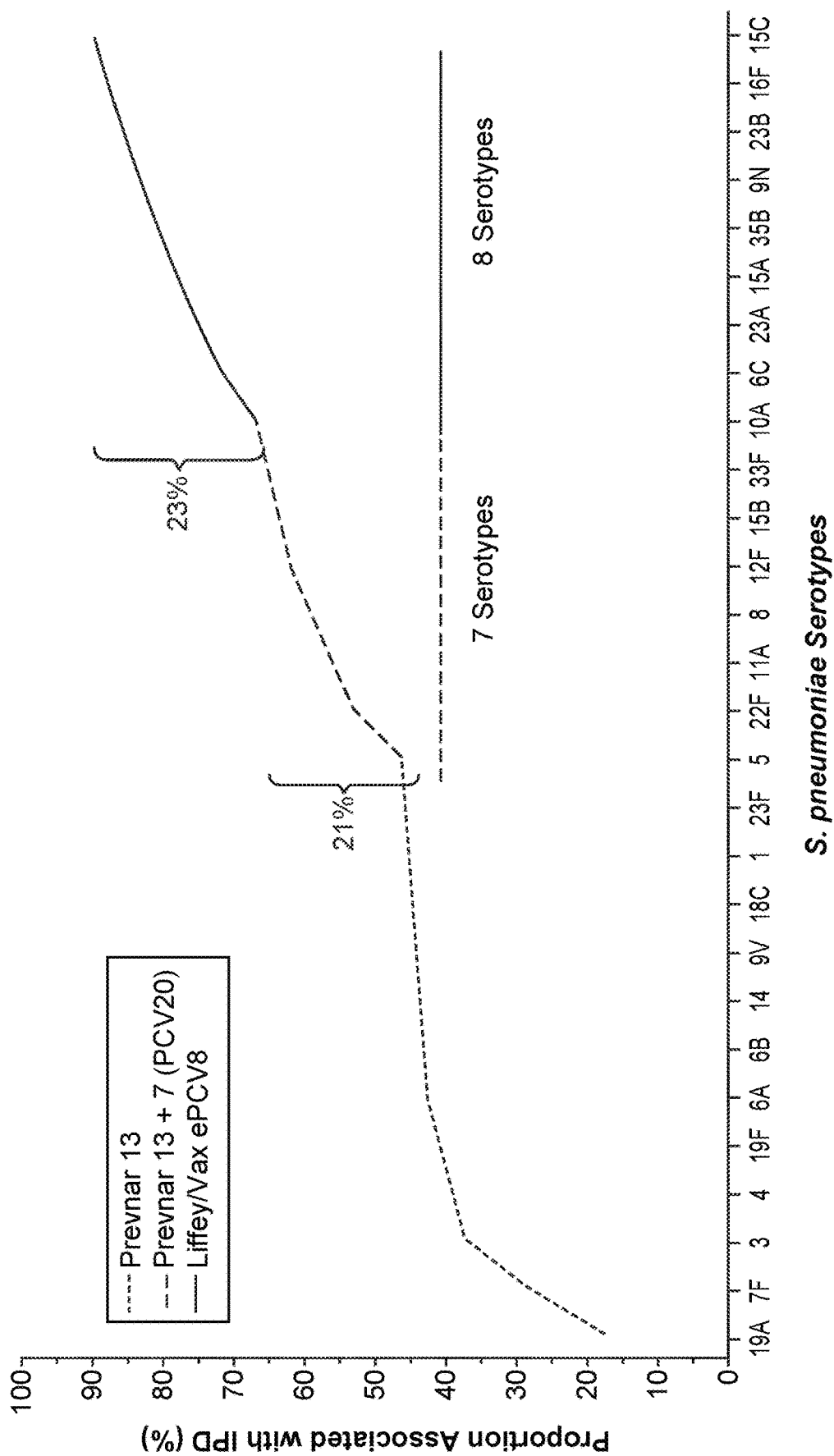
FIG. 8 illustrates the projected expanded coverage provided by a *Streptococcus pneumoniae* polypeptide conjugate vaccine comprising *Streptococcus pneumoniae* serotypes 6C, 9N, 15A, 15C, 16F, 23A, 23B, and 35B (Liffey/Vax ePCV8) against invasive pneumococcal disease (IPD) in United States and Canada when this vaccine is administered in a vaccination regime with Prevnar 13 (PCV13) or a vaccine comprising the Prevnar 13 serotypes plus seven additional serotypes (8, 10A, 11A, 12F, 15B, 22F, and 33F) (PCV20). Prevnar 13 alone only covers about 46.1% of IPD, but the addition of the seven serotypes in the PCV20 is predicted to cover about 21% more of IPD. The further addition of the eight serotypes in the Liffey/Vax ePCV8 is predicted to cover about 23% more of IPD when administered in a vaccination regime with PCV20.
Figure 9:
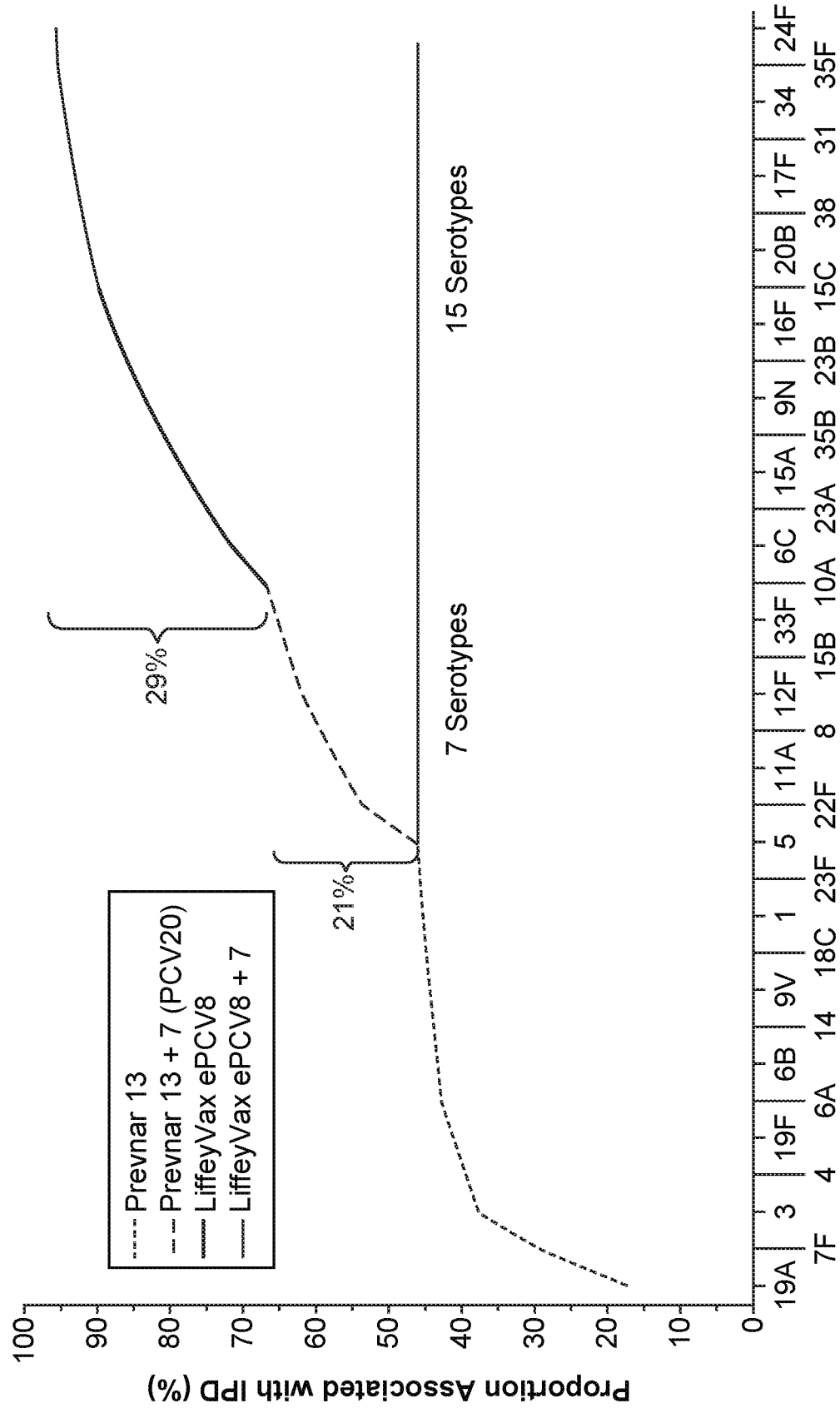
FIG. 9 illustrates the projected expanded coverage provided by a *Streptococcus pneumoniae* polypeptide conjugate vaccine comprising *Streptococcus pneumoniae* serotypes 6C, 9N, 15A, 15C, 16F, 20B, 23A, 23B, 24F, 31, 34, 35F, 35B, and 38 (ePCV8+7) against invasive pneumococcal disease (IPD) in United States and Canada when this vaccine is administered in a vaccination regime with Prevnar 13 (PCV13) or a vaccine comprising the Prevnar 13 serotypes plus seven additional serotypes (8, 10A, 11A, 12F, 15B, 22F, and 33F) (PCV20). Prevnar 13 alone only covers about 46.1% of IPD, but the addition of the seven serotypes in the PCV20 is predicted to cover about 21% more of IPD. The further addition of seven serotypes in the Liffey/Vax ePCV8 (Liffey/Vax ePCV8+7) (see FIG. 8 for ePCV8) is predicted to cover about 29% more of IPD when administered in a vaccination regime with PCV20.
Figure 10A:
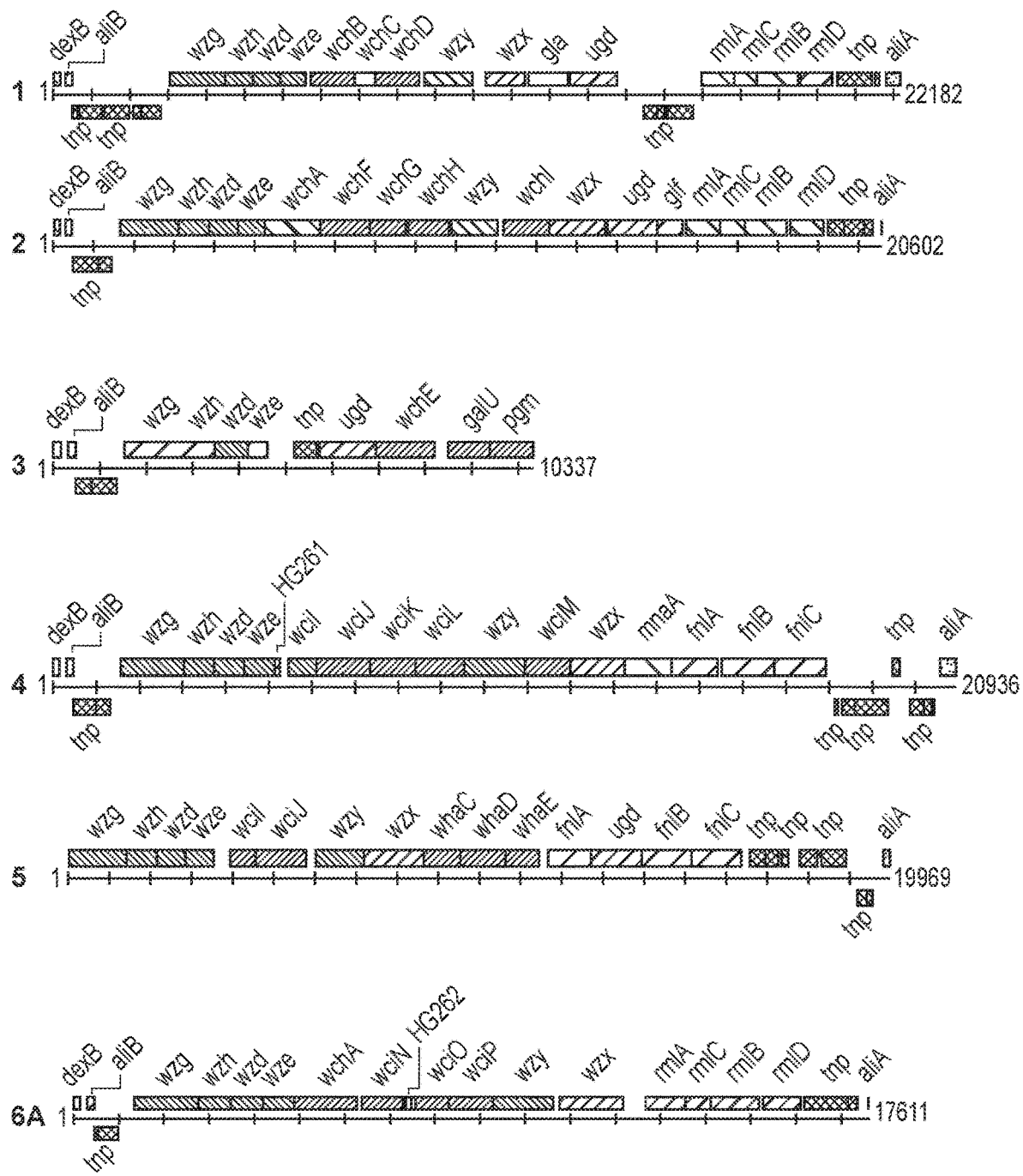
FIGS. 10A, 10B, 10C, 10D, 10E, and 10F illustrate the annotated capsular polysaccharide (cps) locus for various *S. pneumoniae* serotypes (Bentley et al., Genetic Analysis of the Capsular Biosynthetic Locus from all 90 Pneumococcal Serotypes. *PloS Genet* 2(3): 31 (2006)).
Figure 10B:
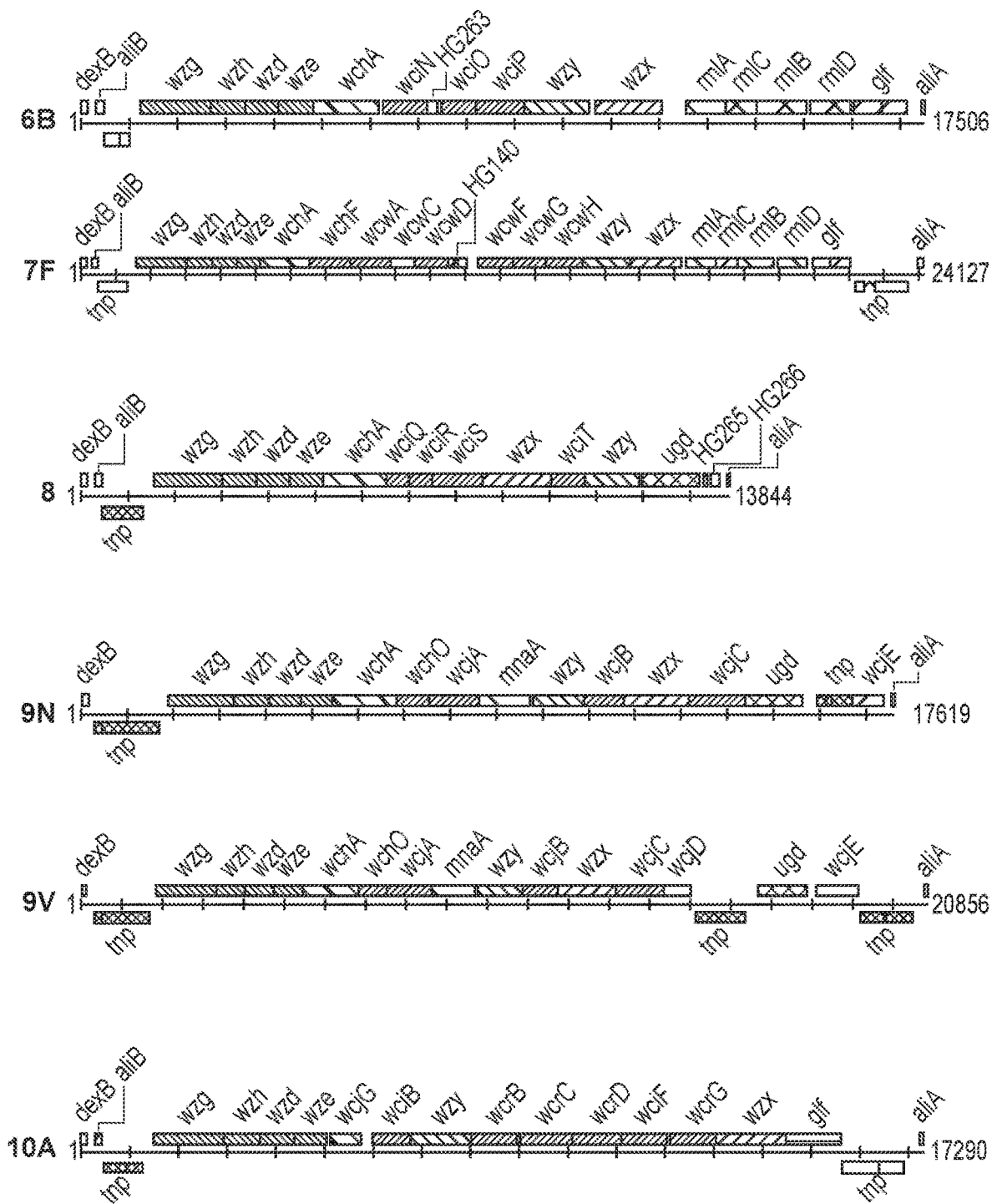
Figure 10C:
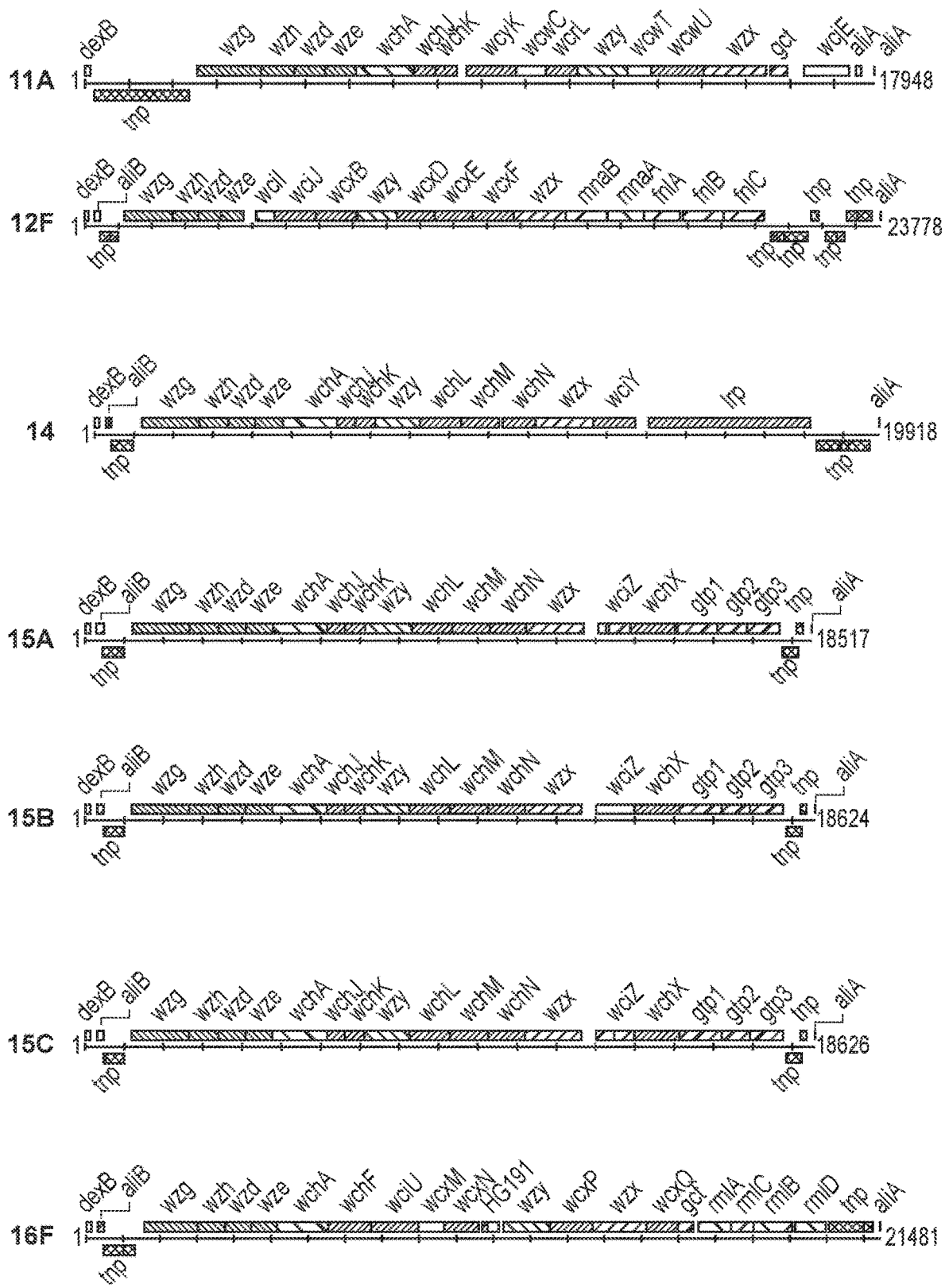
Figure 10D:
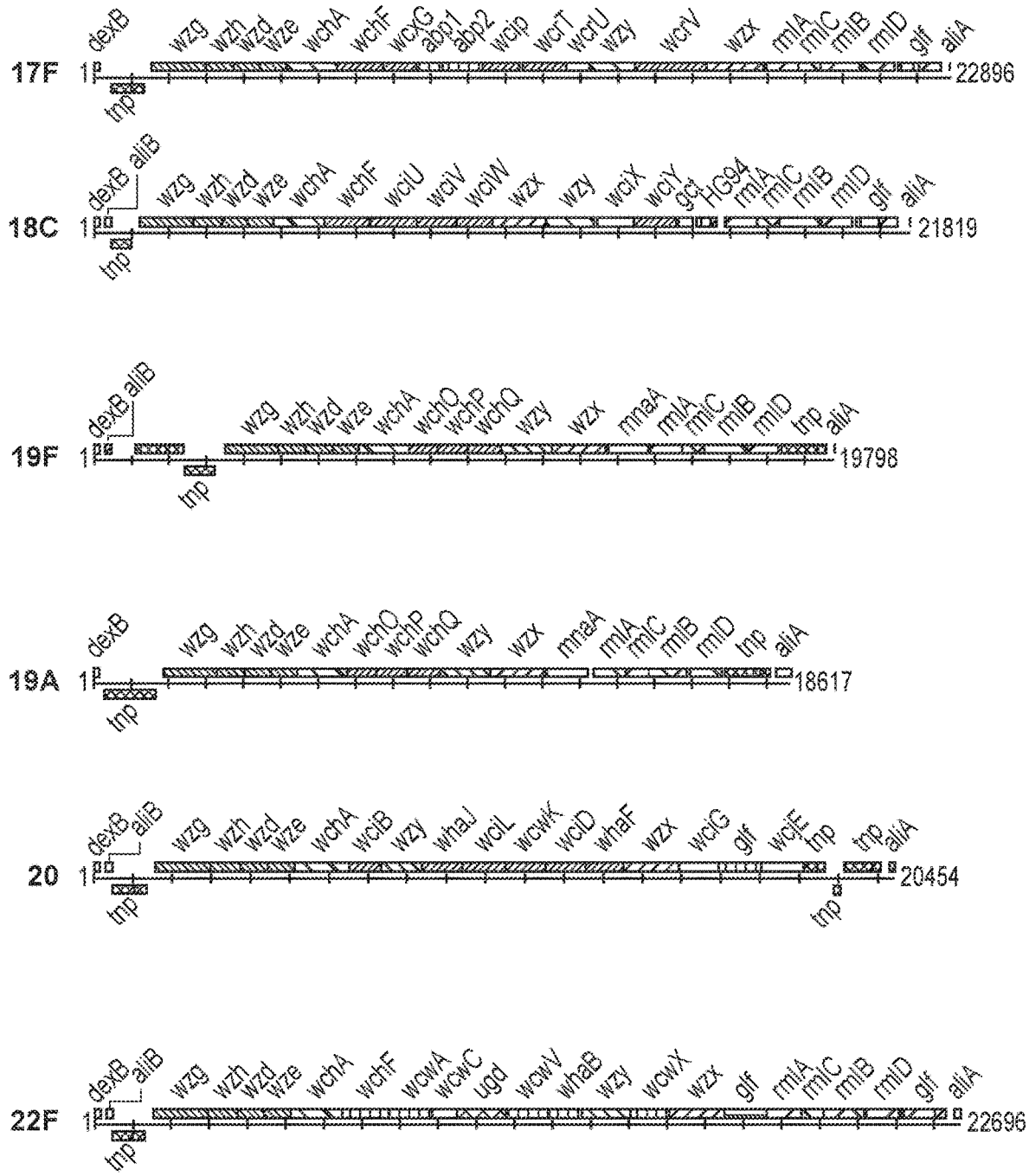
Figure 10E:
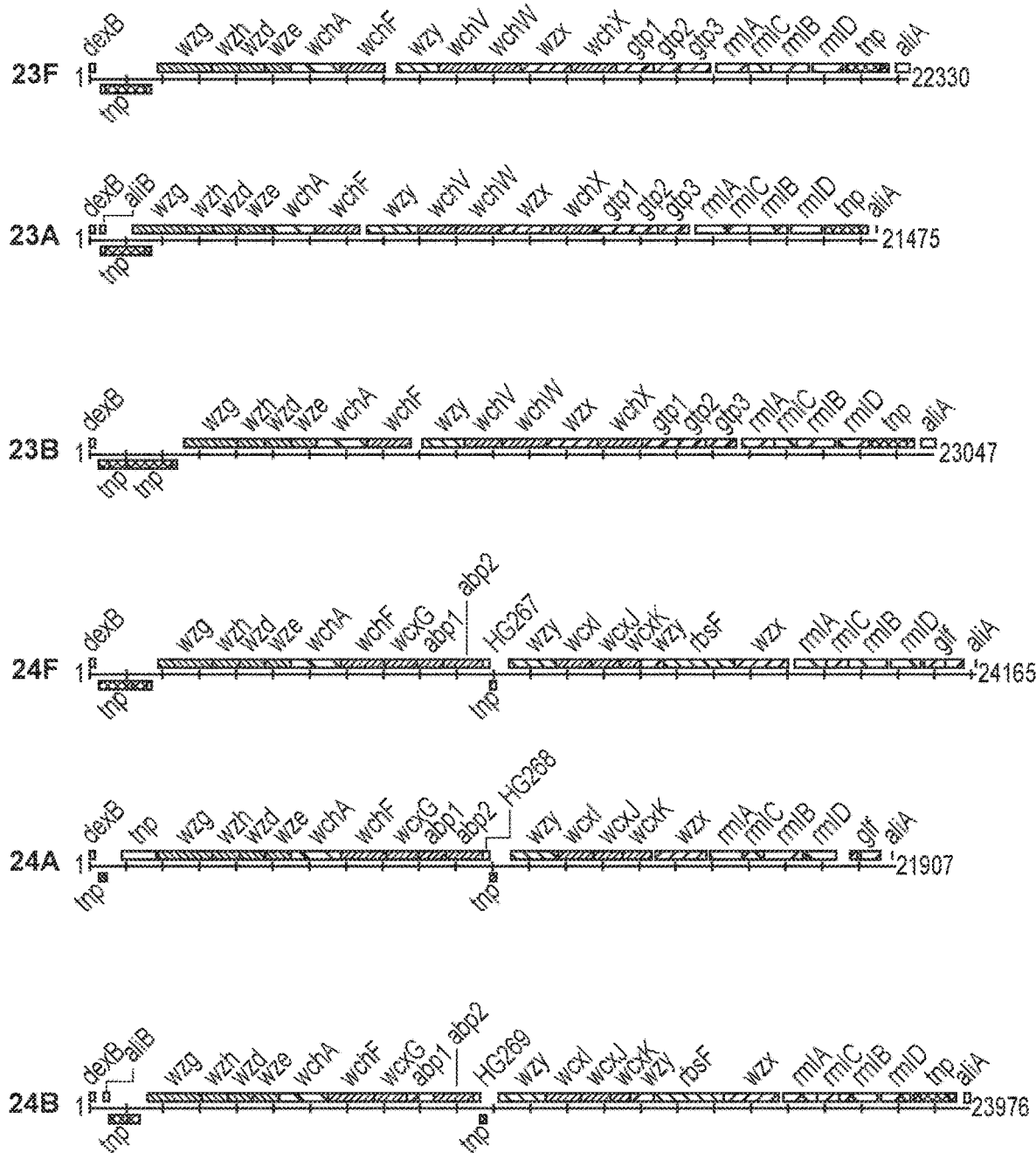
Figure 10F:
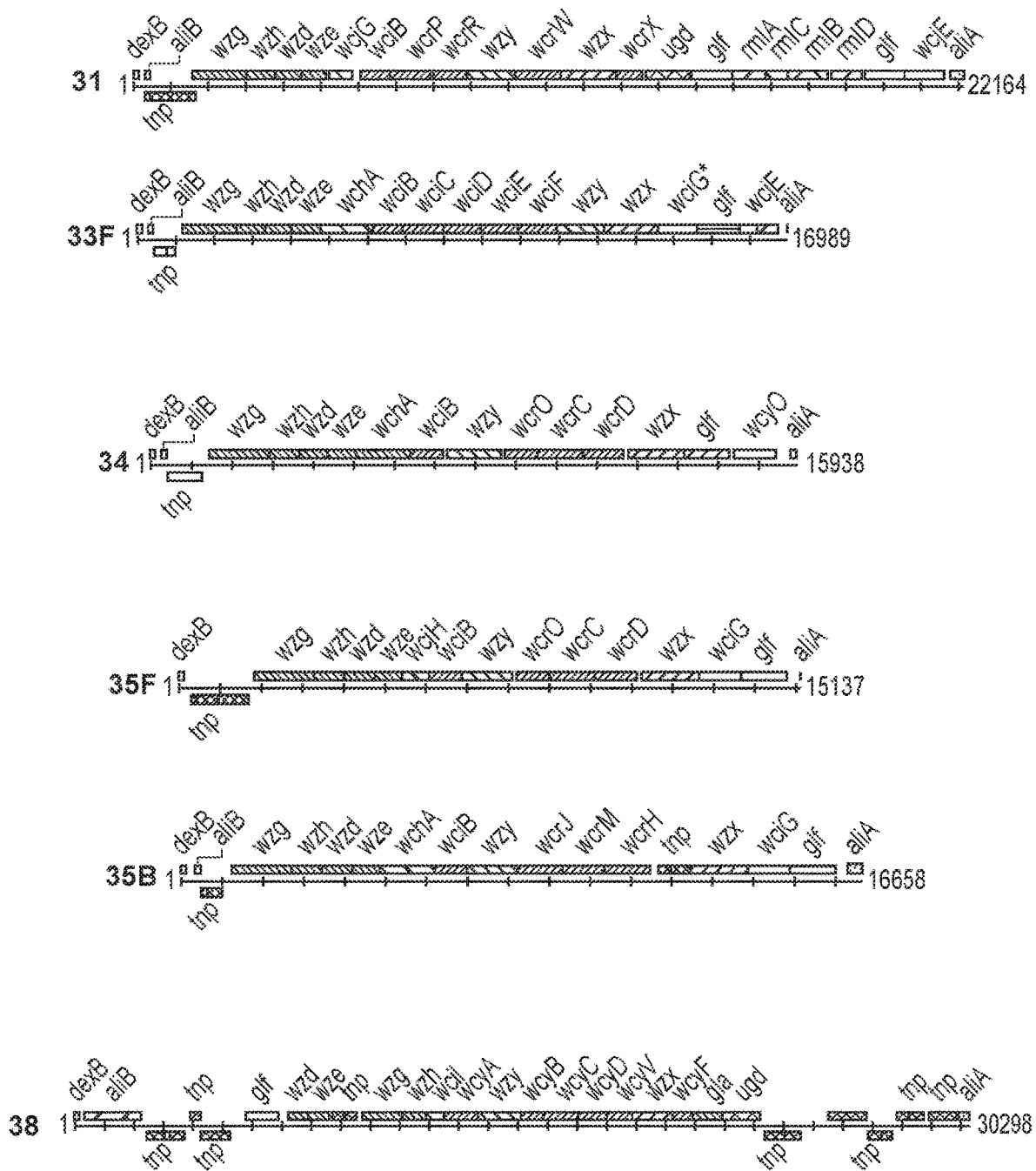

This example shows the formulating process for a polysaccharide CRM$_{197}$ conjugate vaccine. The polysaccharide CRM$_{197}$ conjugates are prepared as described in the above Examples. The formulation process is depicted in FIG. 6. 0.9% w/v sterile saline is added to a formulation container. Each type of conjugate is separately sterilized and the appropriate volume of each monovalent bulk polysaccharide-CRM$_{197}$ conjugate is added (volume is based on the polysaccharide concentration) to the formulation container one at a time. The pH is adjusted to 6.5±0.2 using 1 N HCl or 1 N NaOH. Optionally, an adjuvant is added to the polysaccharide-CRM$_{197}$ conjugate mixture, such as aluminum phosphate to 1 mg/mL final concentration. A calculated volume of sterile saline is added to reach the appropriate final concentration, and then the mixture is blended for approximately two hours. The formulate in the bulk container is then attached to the filling machine, which fills, stoppers, and seals the vials of the final vaccine product. These vial then are inspected, labeled, and packed for distribution. During this process, the pH, appearance of the vaccine, and the vaccine sterility is monitored. At the filling, stoppering, and sealing step, the appearance, pH, identity of polysaccharides, identity of $CRM_{197}$, sterility, saccharide content, total protein content, endotoxin content, pyrogen content, general safety, osmolality, and extractable volume are assessed. 1-5 microgram of polysaccharide per each serotype $CRM_{197}$ conjugate is contained in a 0.5 mL of vaccine in a vial.

Example 9

Rabbit Toxicology Safety Study

This example shows the rabbit toxicology studies that are used to assess vaccine safety. The polysaccharide polypeptide conjugate is produced according to the above EXAMPLES 1, 2, 3, and 5, and comprises the S. pneumoniae polysaccharides from the serotypes 6C, 8, 9N, 10A, 11A, 12F, 15A, 15B, 15C, 16F, 22F, 23A, 23B, 33F, and 35B, which are conjugated to $CRM_{197}$. Alternatively, the polysaccharide polypeptide conjugate is produced according to the above Examples 1, 2, 3, and 5, and comprises the S. pneumoniae polysaccharides from the serotypes 6C, 8, 9N, 10A, 11A, 12F, 15A, 15B, 15C, 16F, 20B, 22F, 23A, 23B, 33F, and 35B, which are conjugated to $CRM_{197}$. These polysaccharide-$CRM_{197}$ conjugates are used in a vaccine formulated according to EXAMPLES 6 and 7. This polysaccharide $CRM_{197}$ conjugate vaccine is administered intramuscularly on days 1, 22, 43, 64, and 85 to rabbits, 5 months of age, (10/gender) at a dose of 0.5 ml/injection into the right thigh muscle. 0.5 ml 0.9% sodium chloride is injected in the Control groups (10/gender). 0.125 mg aluminum phosphate as an adjuvant is injected in the AlP04 group (10/gender). A 4 week dose free recovery period is undertaken in five (5) animals/gender/group after the last injection. Treatment-related mortality and any other toxicologically relevant changes in relative food consumption, ophthalmoscopic parameters, heart rate, respiratory rate, gross anatomy or organ weight is assessed to support lack of systemic toxicity. Injection site are analyzed for reactions and any chronic inflammation. Specific serum antibodies to each of the polysaccharides in the polysaccharide $CRM_{197}$ conjugate vaccine is found in the test group.

The polysaccharide polypeptide conjugate is produced according to the above Examples 1, 2, 3, and 5, and comprises the S. pneumoniae polysaccharides from the serotypes 6C, 8, 9N, 10A, 11A, 12F, 15A, 15B, 15C, 16F, 22F, 23A, 23B, 33F, and 35B, which are conjugated to $CRM_{197}$. Alternatively, the polysaccharide polypeptide conjugate is produced according to the above Examples 1, 2, 3, and 5, and comprises the S. pneumoniae polysaccharides from the serotypes 6C, 8, 9N, 10A, 11A, 12F, 15A, 15B, 15C, 16F, 20B, 22F, 23A, 23B, 33F, and 35B, which are conjugated to $CRM_{197}$. These polysaccharide $CRM_{197}$ conjugates are used in a vaccine formulated according to EXAMPLES 6 and 7. This polysaccharide $CRM_{197}$ conjugate vaccine is administered intramuscularly with and without an aluminum phosphate adjuvant as a single 0.5 mL injection into the left thigh muscle of 3 male rabbits/group, 5 months of age. 0.5 ml 0.9% sodium chloride is administered to the control group (3 males). Treatment related mortality, changes in body weight, relative food consumption, or treatment related macroscopic or microscopic lesions is assessed.

Example 10

Composition and Method of Administration of a Vaccine

This example shows a vaccine composition and a method of administration of that vaccine composition. An aqueous vaccine composition is composed of an immunogenic polysaccharide polypeptide conjugate comprising capsular polysaccharides from any serotype from TABLE 1 conjugated to any one of diphtheria and tetanus toxoids, and variants thereof (e.g., DT, $CRM_{197}$, TT), cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B streptococcus, non-typable H. influenzae P4 protein, non-typable H. influenzae P6 protein, M catarrhalis uspA, keyhole limpet haemocyanin (KLH), OMPC from N. meningitidis, the purified protein derivative of tuberculin (PPD), protein D from H. influenzae, or any fragment thereof; or any combination of polysaccharide polypeptide conjugates as described in Example 6. The aqueous vaccine is formulated to contain from 1-4 microgram of each serotype of polysaccharide per polysaccharide polypeptide conjugate, aluminum phosphate (1 mg/mL), and 0.01% polysorbate 80 in a single 0.5 mL injection delivered intramuscularly to a subject. This vaccine is administered to subject, wherein the subject is a child of 4 weeks to 2 years old. This vaccine is administered to subject, wherein the subject is a child of 2 to 18 years old. This vaccine is administered to a subject, wherein the subject is an adult of at least 50 years of age.

Example 11

Vaccination for Protection Against Endemic S. pneumoniae Serotypes in the United States and Canada This example shows a vaccination of a subject that provides protection against S. pneumoniae for a subject residing in or visiting the United States and/or Canada. The aqueous vaccine composition is composed of an immunogenic saccharide-polypeptide conjugate comprising capsular polysaccharides from the S. pneumoniae serotypes 3, 4, 6A, 6C, 7F, 8, 9N, 10A, 11A, 12F, 15A, 15B, 15C, 16F, 19F, 19A, 22F, 23A, 23B, 33F, 35F, 35B, 38 and Serogroup 20 (comprising serotypes 20A and 20B), such as serotypes 6C, 8, 9N, 11A, 12F, 15A, 15B, 16F, 22F, 23A, 23B, 33F, and 35B. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against S. pneumoniae disease endemic in the United States and Canada is improved.

Example 12

Vaccination for Protection Against Endemic S. pneumoniae Serotypes in Europe, the Middle East, and North Africa This example shows a vaccine composition that provides protection against S. pneumoniae for subjects residing in or visiting Europe, the Middle East, and/or North Africa. The aqueous vaccine composition is composed of an immunogenic saccharide-polypeptide conjugate comprising capsular polysaccharides from the S. pneumoniae serotypes 1, 3, 4, 6A, 6B, 6C, 7F, 8, 9N, 10A, 11A, 12F, 14, 15A, 15B, 16F, 18C, 19F, 19A, 22F, 23F, 23A, 23B, 24F, 33F, 35F, 35B, and 38, such as serotypes 6C, 8, 9N, 10A, 11A, 12F, 15A, 22F, 23A, 23B, 24F, 33F, and 35F. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in Europe, the Middle East, and North Africa is improved.

Example 13

Vaccination for Protection Against Endemic *S. pneumoniae* Serotypes in Japan and Korea This example shows a vaccine composition that provides protection against *S. pneumoniae* for subjects residing in or visiting Japan and/or Korea. The aqueous vaccine composition is composed of an immunogenic saccharide-polypeptide conjugate comprising capsular polysaccharides from the *S. pneumoniae* serotypes 3, 4, 6A, 6B, 6C, 7F, 10A, 11A, 14, 15A, 15B, 19F, 19A, 22F, 23F, 23A, 24F, 35F, 35B, and 38, such as serotypes 6C, 10A, 11A, 15A, 15B, 15C, 22F, 23A, 24B, 33F, 35B, and 38. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in Japan and Korea is improved.

Example 14

Method of Making a 6C-CRM$_{197}$ Conjugate Pharmaceutical Composition

This example shows a method of making a saccharide-polypeptide conjugate pharmaceutical composition. A 6C serotype capsular polysaccharide is isolated from *S. pneumoniae*. The CRM$_{197}$ is produced and purified. The 6C polysaccharide is mixed with CDAP solution, which is then incubated at the appropriate temperature for 6C polysaccharide activation. A calculated amount of CRM$_{197}$ is added to the activated 6C polysaccharides. The reaction is then quenched using glycine or any other suitable quenching reagent. The conjugation reaction mixture is filtered, is diafiltered, and is concentrated for the 6C-CRM$_{197}$ conjugates. The 6C-CRM$_{197}$ conjugates are then purified by gel filtration chromatography. The fractions containing the 6C-CRM$_{197}$ conjugates are pooled, are concentrated, and then are filtered through a 0.2 µm filter. The 6C-CRM$_{197}$ conjugate is formulated for use in a vaccine and is contacted with an excipient.

Example 15

Method of Making a 20B-CRM$_{197}$ Conjugate Pharmaceutical Composition

This example shows a method of making a saccharide-polypeptide conjugate pharmaceutical composition. A 20B serotype capsular polysaccharide is isolated from *S. pneumoniae*. The CRM$_{197}$ is produced and purified. The 20B polysaccharide is mixed with CDAP solution, which is then incubated at the appropriate temperature for 20B polysaccharide activation. A calculated amount of CRM$_{197}$ is added to the activated 20B polysaccharides. The reaction is then quenched using glycine or any other suitable quenching reagent. The conjugation reaction mixture is filtered, is diafiltered, and is concentrated for the 20B-CRM$_{197}$ conjugates. The 20B-CRM$_{197}$ conjugates are then purified by gel filtration chromatography. The fractions containing the 20B-CRM$_{197}$ conjugates are pooled, are concentrated, and then are filtered through a 0.2 µm filter. The 20B-CRM$_{197}$ conjugate is formulated for use in a vaccine and is contacted with an excipient.

Example 16

Composition of a Kit with a Saccharide-Polypeptide Conjugate

This example shows the composition of a kit with a saccharide-polypeptide conjugate. A saccharide-polypeptide conjugate in a vial or a pre-filled syringe is placed in a container. The container is further associated with instructions of use.

Example 17

Vaccination Against *S. pneumoniae*

This example shows a vaccine composition and administration of the vaccine composition to a human subject. An aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 22F, 23A, 23B, 33F, and 35B. The aqueous vaccine is formulated to contain from 1-5 microgram of each serotype and aluminum phosphate as an adjuvant.

A single 0.5 mL dose of the aqueous vaccine is given by intramuscular injection to a human subject. Twenty-eight days later blood is drawn from the human subject and tested for antibodies against each serotype of polysaccharide of the immunogenic saccharide-polypeptide conjugate in the vaccine by in vitro opsonophagocytic assays. After administration of the vaccine, the human subject is found to have antibodies against each serotype of polysaccharide of the immunogenic saccharide-polypeptide conjugate in the vaccine, and therefore, human subject's immunity against these *S. pneumonaie* serotypes is improved.

Example 18

Vaccination Against *S. pneumoniae*

This example shows a vaccine composition and administration of the vaccine composition to a human subject. An aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 20B, 22F, 23A, 23B, 33F, and 35B. The aqueous vaccine is formulated to contain from 1-5 microgram of each serotype and aluminum phosphate as an adjuvant.

A single 0.5 mL dose of the aqueous vaccine is given by intramuscular injection to a human subject. Twenty-eight days later blood is drawn from the human subject and tested for antibodies against each serotype of polysaccharide of the immunogenic saccharide-polypeptide conjugate in the vaccine by in vitro opsonophagocytic assays. After administration of the vaccine, the human subject is found to have antibodies against each serotype of polysaccharide of the immunogenic saccharide-polypeptide conjugate in the vaccine, and therefore, human subject's immunity against these *S. pneumonaie* serotypes is improved.

Example 19

Vaccination Against *S. pneumoniae*

This example shows a vaccine composition and administration of the vaccine composition to a human subject. An aqueous vaccine composition is composed of an immunogenic saccharide-polypeptide conjugate containing capsular polysaccharides from the *S. pneumoniae* serotypes of any of the combinations listed in TABLE 3. The aqueous vaccine is formulated to contain from 1-5 microgram of each serotype and aluminum phosphate as an adjuvant.

A single 0.5 mL dose of the aqueous vaccine is given by intramuscular injection to a human subject. Twenty-eight days later blood is drawn from the human subject and tested for antibodies against each serotype of polysaccharide of the immunogenic saccharide-polypeptide conjugate in the vaccine by in vitro opsonophagocytic assays. After administration of the vaccine, the human subject is found to have antibodies against each serotype of polysaccharide of the immunogenic saccharide-polypeptide conjugate in the vaccine, and therefore, human subject's immunity against these *S. pneumonaie* serotypes is improved.

Example 20

Method of Vaccination

This example shows vaccine compositions and a dosing schedule for the vaccine compositions for a human subject. A first aqueous vaccine composition is composed of an immunogenic saccharide-polypeptide conjugate containing capsular polysaccharides from the *S. pneumoniae* serotypes 1, 3, 4, 5, 6A, 6B, 7F, 9V, 14, 18C, 19A, 19F, and 23F. A second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 22F, 23A, 23B, 33F, and 35B. Each aqueous vaccine is formulated to contain from 1-5 microgram of each serotype and aluminum phosphate as an adjuvant.

A single 0.5 mL dose of the first aqueous vaccine is given by intramuscular injection to a human subject. Four weeks later a single 0.5 mL dose of the second aqueous vaccine is given by intramuscular injection to the human subject. Alternatively to four weeks later, one year later a single 0.5 mL of the second aqueous vaccine is given by intramuscular injection to the human subject.

Example 21

Method of Vaccination

This example shows vaccine compositions and a dosing schedule for the vaccine compositions for a human subject. A first aqueous vaccine composition is composed of an immunogenic saccharide-polypeptide conjugate containing capsular polysaccharides from the *S. pneumoniae* serotypes 1, 3, 4, 5, 6A, 6B, 7F, 9V, 14, 18C, 19A, 19F, and 23F. A second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 20B, 22F, 23A, 23B, 33F, and 35B. Each aqueous vaccine is formulated to contain from 1-5 microgram of each serotype and aluminum phosphate as an adjuvant.

A single 0.5 mL dose of the first aqueous vaccine is given by intramuscular injection to a human subject. Four weeks later a single 0.5 mL dose of the second aqueous vaccine is given by intramuscular injection to the human subject. Alternatively to four weeks later, one year later a single 0.5 mL of the second aqueous vaccine is given by intramuscular injection to the human subject.

Example 22

Method of Vaccination for an Adult Aged 50 Years Old or Older

This example shows vaccine compositions and a dosing schedule for the vaccine compositions for an adult age 50 years old or older. A first aqueous vaccine composition is composed of an immunogenic saccharide-polypeptide conjugate containing capsular polysaccharides from the *S. pneumoniae* serotypes 1, 3, 4, 5, 6A, 6B, 7F, 9V, 14, 18C, 19A, 19F, and 23F. A second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 22F, 23A, 23B, 33F, and 35B. Alternatively, a second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 20B, 22F, 23A, 23B, 33F, and 35B. Each aqueous vaccine is formulated to contain from 1-5 microgram of each serotype and aluminum phosphate as an adjuvant.

A single 0.5 mL dose of the first aqueous vaccine is given by intramuscular injection to an adult age 50 years old or older. Four weeks later a single 0.5 mL dose of the second aqueous vaccine is given by intramuscular injection to the adult aged 50 years old or older. Alternatively to four weeks later, one year later a single 0.5 mL of the second aqueous vaccine is given by intramuscular injection to the adult aged 50 years old or older.

Example 23

Method of Vaccination for a Child Aged 2 to 18 Years Old

This example shows vaccine compositions and a dosing schedule for the vaccine compositions for a child aged 2 to 18 years old. A first aqueous vaccine composition is composed of an immunogenic saccharide-polypeptide conjugate containing capsular polysaccharides from the *S. pneumoniae* serotypes 1, 3, 4, 5, 6A, 6B, 7F, 9V, 14, 18C, 19A, 19F, and 23F. A second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 22F, 23A, 23B, 33F, and 35B. Alternatively, a second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 20B, 22F, 23A, 23B, 33F, and 35B. Each aqueous vaccine is formulated to contain from 1-5 microgram of each serotype and aluminum phosphate as an adjuvant.

A single 0.5 mL dose of the first aqueous vaccine is given by intramuscular injection to a child aged 2 to 18 years old. Four weeks later a single 0.5 mL dose of the second aqueous vaccine is given by intramuscular injection to the child aged 2 to 18 years old. Alternatively to four weeks later, one year later a single 0.5 mL of the second aqueous vaccine is given by intramuscular injection to the child aged 2 to 18 years old.

Example 24

Method of Vaccination for a Child Aged 4 Weeks to 2 Years Old

This example shows vaccine compositions and a dosing schedule for the vaccine compositions for a child aged 4 weeks to 2 years old. A first aqueous vaccine composition is composed of an immunogenic saccharide-polypeptide conjugate containing capsular polysaccharides from the *S. pneumoniae* serotypes 1, 3, 4, 5, 6A, 6B, 7F, 9V, 14, 18C, 19A, 19F, and 23F. A second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 22F, 23A, 23B, 33F, and 35B. Alternatively, a second aqueous vaccine composition is composed of an immunogenic saccharide-polypeptide conjugate containing capsular polysaccharides from the *S. pneumoniae* serotypes 6C, 8, 9N, 10A, 11A, 12F, 15A, 15B, 15C, 20B, 22F, 23A, 23B, 33F, and 35B. Each aqueous vaccine is formulated to contain from 1-5 microgram of each serotype and aluminum phosphate as an adjuvant.

A single 0.5 mL dose of the first aqueous vaccine is given by intramuscular injection to a child aged 4 weeks to 2 years old. Four weeks later a single 0.5 mL dose of the second aqueous vaccine is given by intramuscular injection to the child who is 2-18 years old. Alternatively to four weeks later, one year later a single 0.5 of the second aqueous vaccine is given by intramuscular injection to the child aged 4 weeks to 2 years old.

Example 25

Method of Vaccination for *S. pneumoniae* and *N. meningitidis*

This example shows vaccine compositions and a dosing schedule that provides protection against *S. pneumoniae* and *N. meningitidis*. A first aqueous vaccine composition is composed of an immunogenic saccharide-polypeptide conjugate containing capsular polysaccharides from the *S. pneumoniae* 6C, 8, 9N, 10A, 11A, 12F, 15A, 15B, 15C, 22F, 23A, 23B, 33F, and 35B conjugated to $CRM_{197}$. A second aqueous vaccine composition is composed of an immunogenic saccharide-polypeptide conjugate containing *N. meningitidis* group C capsular saccharide conjugated to $CRM_{197}$. Each vaccine is formulated for intramuscular injection.

A single 0.5 mL dose of the first aqueous vaccine is given by intramuscular injection to a subject. One month later a single dose of the second aqueous vaccine is given by intramuscular injection to a subject. Alternatively, the first aqueous vaccine is given by intramuscular injection one month after the second aqueous vaccine is given by intramuscular injection.

Example 26

Method of Vaccination for *S. pneumoniae* and *S. enterica*

This example shows vaccine compositions and a dosing schedule that provides protection against *S. pneumoniae* and *S. enterica*. A first aqueous vaccine composition is composed of an immunogenic saccharide-polypeptide conjugate containing capsular polysaccharides from the *S. pneumoniae* 6C, 8, 9N, 10A, 11A, 12F, 15A, 15B, 15C, 22F, 23A, 23B, 33F, and 35B conjugated to $CRM_{197}$. A second aqueous vaccine composition is composed of an immunogenic saccharide-polypeptide conjugate containing *S. enterica* subspecies *enterica* serovar *Typhi* Vi-capsular saccharide conjugated to $CRM_{197}$. Each aqueous vaccine is formulated for intramuscular injection.

A single 0.5 mL dose of the first aqueous vaccine is given by intramuscular injection to a subject. One month later a single dose of the second aqueous vaccine is given by intramuscular injection to a subject. Alternatively, the first aqueous vaccine is given by intramuscular injection one month after the second aqueous vaccine by intramuscular injection.

Example 27

Method of Vaccination for *S. pneumoniae*, *N. meningitidis*, and *H. influenzae*

This example shows vaccine compositions and a dosing schedule that provides protection against *S. pneumoniae*, *N. meningitidis*, and *H. influenzae*. A first aqueous vaccine composition is composed of an immunogenic saccharide-polypeptide conjugate containing capsular polysaccharides from the *S. pneumoniae* 6C, 8, 9N, 10A, 11A, 12F, 15A, 15B, 15C, 22F, 23A, 23B, 33F, and 35B conjugated to a tetanus toxoid carrier protein. A second aqueous vaccine composition is composed of an immunogenic saccharide-polypeptide conjugate containing *N. meningitidis* group C and group Y saccharide and *H. influenzae* type b saccharide individually conjugated a tetanus toxoid carrier protein. Each aqueous vaccine is formulated for intramuscular injection.

A single 0.5 mL dose of the first aqueous vaccine is given by intramuscular injection to a subject. One month later a single dose of the second aqueous vaccine is given by intramuscular injection to a subject. Alternatively, the first aqueous vaccine is given by intramuscular injection one month after the second aqueous vaccine by intramuscular injection.

Example 28

Serotype 23A Vaccination Against *S. pneumoniae*

This example shows a vaccine composition and administration of the vaccine composition to a human subject. An aqueous vaccine composition is comprised of immunogenic saccharide-polypeptide conjugates comprising a capsular polysaccharide from the *S. pneumoniae* serotypes 23A. The aqueous vaccine is formulated to contain from 1-5 microgram of each serotype and aluminum phosphate as an adjuvant.

A single 0.5 mL dose of the aqueous vaccine is given by intramuscular injection to a human subject. Twenty-eight days later blood is drawn from the human subject and tested for antibodies against each serotype of polysaccharide of the immunogenic saccharide-polypeptide conjugate in the vaccine by in vitro opsonophagocytic assays. After administration of the vaccine, the human subject is found to have antibodies against each serotype of polysaccharide of the immunogenic saccharide-polypeptide conjugate in the vaccine, and therefore, human subject's immunity against these *S. pneumonaie* serotypes is improved.

Example 29

Serotype 23B Vaccination Against *S. pneumoniae*

This example shows a vaccine composition and administration of the vaccine composition to a human subject. An aqueous vaccine composition is comprised of immunogenic saccharide-polypeptide conjugates comprising a capsular polysaccharide from the *S. pneumoniae* serotypes 23B. The aqueous vaccine is formulated to contain from 1-5 microgram of each serotype and aluminum phosphate as an adjuvant.

A single 0.5 mL dose of the aqueous vaccine is given by intramuscular injection to a human subject. Twenty-eight days later blood is drawn from the human subject and tested for antibodies against each serotype of polysaccharide of the immunogenic saccharide-polypeptide conjugate in the vaccine by in vitro opsonophagocytic assays. After administration of the vaccine, the human subject is found to have antibodies against each serotype of polysaccharide of the immunogenic saccharide-polypeptide conjugate in the vaccine, and therefore, human subject's immunity against these *S. pneumonaie* serotypes is improved.

Example 30

Vaccination for Protection Against Endemic *S. pneumoniae* Serotypes in the United States This example shows a vaccination of a subject that provides protection against *S. pneumoniae* for a subject residing in or visiting the United States. The aqueous vaccine composition is composed of an immunogenic saccharide-polypeptide conjugate comprising capsular polysaccharides from the *S. pneumoniae* serotypes 3, 6C, 7C, 8, 9N, 11A, 12F, 15A, 16F, 19A, 19F, 22F, 23A, 23B, 31, 33F, 35B, 35F, 38, and Serogroup 20 (comprising serotypes 20A and 20B). The immunogenic saccharide-polypeptide conjugates are made using the methods as described herein. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in the United States is improved.

Example 31

Vaccination for Protection Against Endemic *S. pneumoniae* Serotypes in the United States This example shows a vaccination of a subject that provides protection against *S. pneumoniae* for a subject residing in or visiting the United States. The aqueous vaccine composition is composed of an immunogenic saccharide-polypeptide conjugate comprising capsular polysaccharides from the *S. pneumoniae* serotypes 3, 6C, 8, 9N, 11A, 12F, 15A, 15B, 16F, 19A, 19F, 22F, 23A, 23B, 31, 33F, 35B, 35F, 38, and Serogroup 20 (comprising serotypes 20A and 20B). The immunogenic saccharide-polypeptide conjugates are made using the methods as described herein. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in the United States is improved.

Example 32

Vaccination for Protection Against Endemic *S. pneumoniae* Serotypes in the United Kingdom This example shows a vaccination of a subject that provides protection against *S. pneumoniae* for a subject residing in or visiting the United Kingdom. The aqueous vaccine composition is composed of an immunogenic saccharide-polypeptide conjugate comprising capsular polysaccharides from the *S. pneumoniae* serotypes 3, 6C, 7F, 8, 9N, 10A, 11A, 12F, 15A, 15B, 15C, 16F, 19A, 22F, 23A, 23B, 24F, 33F, 35B, and 38. The immunogenic saccharide-polypeptide conjugates are made using the methods as described herein. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in the United Kingdom is improved.

Example 33

Vaccination for Protection Against Endemic *S. pneumoniae* Serotypes in Germany

This example shows a vaccination of a subject that provides protection against *S. pneumoniae* for a subject residing in or visiting Germany. The aqueous vaccine composition is composed of an immunogenic saccharide-polypeptide conjugate comprising capsular polysaccharides from the *S. pneumoniae* serotypes 3, 4, 6C, 7F, 8, 9N, 10A, 11A, 12F, 15A, 15B, 15C, 16F, 19A, 22F, 23A, 23B, 24F, 31, 33F, 35B, 35F, 38, and Serogroup 20 (comprising serotypes 20A and 20B). The immunogenic saccharide-polypeptide conjugates are made using the methods as described herein. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in Germany is improved.

Example 34

Vaccination for Protection Against Endemic *S. pneumoniae* Serotypes in Germany

This example shows a vaccination of a subject that provides protection against *S. pneumoniae* for a subject residing in or visiting Germany. The aqueous vaccine composition is composed of an immunogenic saccharide-polypeptide conjugate comprising capsular polysaccharides from the *S. pneumoniae* serotypes 3, 6C, 8, 9N, 11A, 12F, 15A, 15B, 16F, 19A, 22F, 23A, 23B, 31, 33F, 35B, 35F, 38, and Serogroup 20 (comprising serotypes 20A and 20B). The immunogenic saccharide-polypeptide conjugates are made using the methods as described herein. The aqueous vaccine is formulated to contain from 1-5 microgram of each serotype and aluminum phosphate as an adjuvant. A single 0.5 mL dose of the aqueous vaccine is given by intramuscular injection to the subject. After administration, immunity of the subject against *S. pneumoniae* disease endemic in Germany is improved.

While preferred embodiments of the present invention have been shown and described herein, it will be apparent to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A pharmaceutical composition comprising a plurality of immunogenic saccharide-polypeptide conjugates, each comprising individually a capsular polysaccharide, fragment thereof, or combination thereof conjugated to a polypeptide, wherein each of the capsular polysaccharides, fragments thereof, or combinations thereof is from a *Streptococcus pneumoniae* serotype; wherein the *Streptococcus pneumoniae* serotypes in the plurality of immunogenic saccharide-polypeptide conjugates comprise at least serotypes 6C, 8, 9N, 10A, 11A, 12F, 15A, 20B, 22F, 23A, 23B, 24F, 33F, and 35B; and
   wherein the fragment or fragments of the capsular polysaccharide is a monosaccharide, a disaccharide, a trisaccharide, a tetrasaccharide, a pentasaccharide, a hexasaccharide, or an oligosaccharide.

2. The pharmaceutical composition of claim 1 further comprising at least one additional immunogenic saccharide-polypeptide conjugate from *Streptococcus pneumoniae* serotype 1, 2, 3, 4, 5, 6A, 6B, 7C, 7F, 9V, 14, 15B, 15C, 16F, 17F, 18C, 19A, 19F, 20A, 23F, 24B, 31, 33B, 34, or 38.

3. The pharmaceutical composition of claim 1, wherein at least one of the immunogenic saccharide-polypeptide conjugates comprises a bacterial toxin or bacterial toxin-derived polypeptide to which the capsular polysaccharide, fragment thereof, or combination thereof is conjugated.

4. The pharmaceutical composition of claim 3, wherein the bacterial toxin or bacterial toxin-derived polypeptide comprises tetanus toxoid, diphtheria toxoid, cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B *Streptococcus*, non-typable *Haemophilus influenzae* P4 protein, non-typable *H. influenzae* P6 protein, *Moraxella catarrhalis* uspA, keyhole limpet haemocyanin (KLH), outer membrane protein complex (OMPC) from *Neisseria meningitidis*, purified protein derivative of tuberculin (PPD), protein D from *H. influenzae*, PspA, or a fragment or combination thereof.

5. The pharmaceutical composition of claim 3, wherein the bacterial toxin or bacterial toxin-derived polypeptide comprises cross-reacting material 197 ($CRM_{197}$) or a fragment thereof.

6. The pharmaceutical composition of claim 1, wherein each of the immunogenic saccharide-polypeptide conjugates comprises:
  (i) the capsular polysaccharide, fragments thereof, or combinations thereof at least partially embedded in the polypeptide,
  (ii) the capsular polysaccharide, fragments thereof, or combinations thereof chemically cross-linked to the polypeptide, and/or
  (iii) the capsular polysaccharide, fragments thereof, or combinations thereof at least partially chemically cross-linked to the polypeptide.

7. The pharmaceutical composition of claim 1, wherein at least one of the immunogenic saccharide-polypeptide conjugates comprises an immunogenic saccharide-cross-reacting material 197 ($CRM_{197}$) conjugate.

8. The pharmaceutical composition of claim 1, wherein the pharmaceutical composition is in the form of an intramuscularly injectable composition, intradermally injectable composition, subcutaneously injectable composition, or intranasally administrable composition.

9. A vaccine comprising the pharmaceutical composition of claim 1.

10. A method comprising administering to a subject in need thereof the pharmaceutical composition of claim 1.

11. A pharmaceutical composition comprising a plurality of immunogenic saccharide-polypeptide conjugates, each comprising individually a capsular polysaccharide, fragment thereof, or combination thereof conjugated to a polypeptide, wherein each of the capsular polysaccharides, fragments thereof, or combinations thereof is from a *Streptococcus pneumoniae* serotype, wherein the *Streptococcus pneumoniae* serotypes in the plurality of immunogenic saccharide-polypeptide conjugates comprise:
  (i) at least serotypes 6C, 8, 9N, 10A, 11A, 12F, 15A, 15B, 20B, 22F, 23A, 23B, 33F, and 35B;
  (ii) at least serotypes 6C, 8, 9N, 11A, 12F, 15A, 15B, 16F, 20B, 22F, 23A, 23B, 24F, 33F, and 35B;
  (iii) at least serotypes 6C, 10A, 11A, 15A, 15B, 15C, 20B, 22F, 23A, 24B, 33F, 35B, and 38;
  (iv) at least serotypes 6C, 8, 9N, 10A, 12F, 15A, 15B, 15C, 16F, 20B, 22F, 23A, 23B, 33F, and 35B;
  (v) at least serotypes 6C, 8, 9N, 11A, 12F, 15A, 15B, 16F, 20B, 22F, 23A, 23B, 33F, and 35B; or
  (vi) at least serotypes 6C, 15A, 15C, 16F, 20B, 23A, 23B, 24F, 31, 33F, 34, 35B, and 35F.

12. The pharmaceutical composition of claim 11, wherein at least one of the immunogenic saccharide-polypeptide conjugates comprises a bacterial toxin or bacterial toxin-derived polypeptide to which the capsular polysaccharide, fragment thereof, or combination thereof is conjugated.

13. The pharmaceutical composition of claim 12, wherein the bacterial toxin or bacterial toxin-derived polypeptide comprises tetanus toxoid, diphtheria toxoid, cholera toxoid, pertussis toxoid, inactivated or mutant pneumococcal pneumolysin, pneumococcal surface protein A, pneumococcal adhesion protein A, pneumococcal lipoprotein PsaA, C5a peptidase group A or group B *Streptococcus*, non-typable *Haemophilus influenzae* P4 protein, non-typable *H. influenzae* P6 protein, *Moraxella catarrhalis* uspA, keyhole limpet haemocyanin (KLH), outer membrane protein complex (OMPC) from *Neisseria meningitidis*, purified protein derivative of tuberculin (PPD), protein D from *H. influenzae*, PspA, or a fragment or combination thereof.

14. The pharmaceutical composition of claim 12, wherein the bacterial toxin or bacterial toxin-derived polypeptide comprises cross-reacting material 197 ($CRM_{197}$) or a fragment thereof.

15. The pharmaceutical composition of claim 11, wherein each of the immunogenic saccharide-polypeptide conjugates comprises:
  (i) the capsular polysaccharide, fragments thereof, or combinations thereof at least partially embedded in the polypeptide,
  (ii) the capsular polysaccharide, fragments thereof, or combinations thereof chemically cross-linked to the polypeptide, and/or
  (iii) the capsular polysaccharide, fragments thereof, or combinations thereof at least partially chemically cross-linked to the polypeptide.

16. The pharmaceutical composition of claim 11, wherein at least one of the immunogenic saccharide-polypeptide conjugates comprises an immunogenic saccharide-cross-reacting material 197 ($CRM_{197}$) conjugate.

17. The pharmaceutical composition of claim 11, wherein the pharmaceutical composition is in the form of an intramuscularly injectable composition, intradermally injectable composition, subcutaneously injectable composition, or intranasally administrable composition.

18. A vaccine comprising the pharmaceutical composition of claim 11.

19. A method comprising administering to a subject in need thereof the pharmaceutical composition of claim 11.

20. The pharmaceutical composition of claim 11 further comprising at least one additional immunogenic saccharide-polypeptide conjugate from *Streptococcus pneumoniae* serotype 1, 2, 3, 4, 5, 6A, 6B, 7C, 7F, 9V, 14, 15B, 15C, 16F, 17F, 18C, 19A, 19F, 20A, 23F, 24B, 31, 33B, 34, or 38.

* * * * *